US011304633B2

(12) United States Patent
Koya et al.

(10) Patent No.: US 11,304,633 B2
(45) Date of Patent: Apr. 19, 2022

(54) SYSTEM AND METHOD FOR PROVIDING GLUCOSE CONTROL THERAPY

(71) Applicant: Boston Scientific Scimed, Inc., Maple Grove, MN (US)

(72) Inventors: Vijay Koya, Blaine, MN (US); Bryan Allen Clark, Forest Lake, MN (US); Kyle Harish Srivastava, Saint Paul, MN (US); Michael X. Govea, Castaic, CA (US); Elizabeth Mary Annoni, White Bear Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 132 days.

(21) Appl. No.: 16/178,872

(22) Filed: Nov. 2, 2018

(65) Prior Publication Data

US 2019/0125227 A1 May 2, 2019

Related U.S. Application Data

(60) Provisional application No. 62/580,723, filed on Nov. 2, 2017.

(51) Int. Cl.
*A61N 1/36* (2006.01)
*A61N 1/05* (2006.01)
(Continued)

(52) U.S. Cl.
CPC ...... *A61B 5/14532* (2013.01); *A61B 5/14865* (2013.01); *A61B 5/4839* (2013.01);
(Continued)

(58) Field of Classification Search
USPC ................................. 607/40, 89
See application file for complete search history.

(56) References Cited

U.S. PATENT DOCUMENTS 6,558,351 B1 5/2003 Steil et al.
6,832,114 B1 12/2004 Whitehurst et al.
(Continued)

FOREIGN PATENT DOCUMENTS

WO WO-2006124716 A2 11/2006
WO WO-2014197625 A1 12/2014
(Continued)

OTHER PUBLICATIONS

Ferrannini, Ele, "The Target of Metformin in Type 2 Diabetes", New England Journal of Medicine, 371:16, (Oct. 16, 2014), 1547-1548.
(Continued)

*Primary Examiner* — Jon Eric C Morales
(74) *Attorney, Agent, or Firm* — Schwegman Lundberg & Woessner, P.A.

(57) ABSTRACT

A system may include an implantable structure with a plurality of electrodes attached thereto, where the implantable structure is configured to be implanted proximate to a nerve that innervates and is proximate to an organ involved with glucose control. The system may further include a controller configured for use to control which of the plurality of electrodes are modulation electrodes and which of the plurality of electrodes are sense electrodes, a modulation energy generator configured to deliver modulation energy using one or more of the modulation electrodes, and a nerve traffic sensor configured to sense nerve traffic in the nerve using one or more of the sense electrodes. The controller may be configured to determine if the delivered modulation energy captures the nerves based on the sensed neural activity.

18 Claims, 29 Drawing Sheets

(51) Int. Cl.
  *A61B 5/145*    (2006.01)
  *A61B 5/1486*   (2006.01)
  *A61M 5/172*    (2006.01)
  *A61M 5/142*    (2006.01)
  *A61B 5/00*     (2006.01)
  *A61B 5/1495*   (2006.01)

(52) U.S. Cl.
  CPC ...... *A61M 5/14248* (2013.01); *A61M 5/1723* (2013.01); *A61N 1/3606* (2013.01); *A61N 1/36017* (2013.01); *A61N 1/36135* (2013.01); *A61B 5/0093* (2013.01); *A61B 5/1495* (2013.01); *A61M 2005/14208* (2013.01); *A61M 2230/201* (2013.01)

(56) References Cited

U.S. PATENT DOCUMENTS

| | | | |
|---|---|---|---|
| 8,412,345 | B2 | 4/2013 | Moffitt |
| 8,467,972 | B2 | 6/2013 | Rush |
| 8,583,229 | B2 | 11/2013 | Rezai et al. |
| 8,909,350 | B2 | 12/2014 | Lee |
| 8,934,975 | B2 | 1/2015 | Yaniv et al. |
| 9,149,329 | B2 | 10/2015 | Azamian et al. |
| 2003/0195404 | A1 | 10/2003 | Knobbe et al. |
| 2006/0085045 | A1 | 4/2006 | Harel et al. |
| 2008/0004672 | A1 | 1/2008 | Dalal et al. |
| 2008/0039904 | A1 | 2/2008 | Bulkes et al. |
| 2009/0131993 | A1 | 5/2009 | Rousso et al. |
| 2011/0313483 | A1 | 12/2011 | Ordonez et al. |
| 2013/0317573 | A1* | 11/2013 | Zhu .................. A61N 1/0529 607/89 |
| 2015/0202446 | A1 | 7/2015 | Franke et al. |
| 2016/0256683 | A1* | 9/2016 | Butera ............... A61N 1/36139 |
| 2017/0173340 | A1 | 6/2017 | Gupte et al. |
| 2017/0361101 | A1* | 12/2017 | Single .............. A61N 1/36071 |
| 2018/0125689 | A1 | 5/2018 | Perez et al. |
| 2019/0125226 | A1* | 5/2019 | Koya ............... A61B 5/14532 |

FOREIGN PATENT DOCUMENTS

| | | |
|---|---|---|
| WO | WO-2016090436 A1 | 6/2016 |
| WO | WO-2016141184 A1 | 9/2016 |
| WO | WO-2019090009 A1 | 5/2019 |
| WO | WO-2019090016 A1 | 5/2019 |

OTHER PUBLICATIONS

Garcia-Perez, Luis-Emili, et al., "Adherence to Therapies in Patients with Type 2 Diabetes", Diabetes Therapy, 4, (2013), 175-194.
MacLean, Charles D., et al., "Limitations of diabetes pharmacotherapy: results from the Vermont Diabetes Information System study", BMC Family Practice, 7:50, (Aug. 2006), 6 pgs.
Vaddiraju, Santhisagar, et al., "Technologies for Continuous Glucose Monitoring: Current Problems and Future Promises", Journal of Diabetes Science and Technology vol. 4, Issue 6, Nov. 2010, © Diabetes Technology Society, pp. 1540-1562.
Zhuo, Xiaohui, et al., "Lifetime Direct Medical Costs of Treating Type 2 Lifetime Direct Medical Costs of Treating Type 2", Am J Prev Med 2013;45(3):253-261.
"International Application Serial No. PCT/US2018/058827, International Preliminary Report on Patentability dated May 14, 2020", 9 pgs.
"International Application Serial No. PCT/US2018/058827, International Search Report dated Feb. 1, 2019", 5 pgs.
"International Application Serial No. PCT/US2018/058827, Written Opinion dated Feb. 1, 2019", 7 pgs.
"International Application Serial No. PCT/US2018/058839, International Preliminary Report on Patentability dated May 14, 2020", 10 pgs.
"International Application Serial No. PCT/US2018/058839, International Search Report dated Feb. 4, 2019", 5 pgs.
"International Application Serial No. PCT/US2018/058839, Written Opinion dated Feb. 4, 2019", 8 pgs.
"U.S. Appl. No. 16/178,777, Non Final Office Action dated Aug. 12, 2020", 12 pgs.
"U.S. Appl. No. 16/178,777, Response filed Nov. 11, 2020 to Non Final Office Action dated Aug. 12, 2020", 9 pgs.
"European Application Serial No. 18815063.5, Response to Communication Pursuant to Rules 161 and 162 filed Dec. 9, 2020", 24 pgs.
"U.S. Appl. No. 16/178,777, Advisory Action dated Apr. 2, 2021", 3 pgs.
"U.S. Appl. No. 16/178,777, Final Office Action dated Jan. 21, 2021", 13 pgs.
"U.S. Appl. No. 16/178,777, Response filed Mar. 22, 2021 to Final Office Action dated Jan. 21, 2021", 11 pgs.
"European Application Serial No. 18804840.9, Response filed Jan. 14, 2021 to Communication pursuant to Rules 161(1) and 162 EPC dated Jun. 23, 2020", 22 pgs.

* cited by examiner

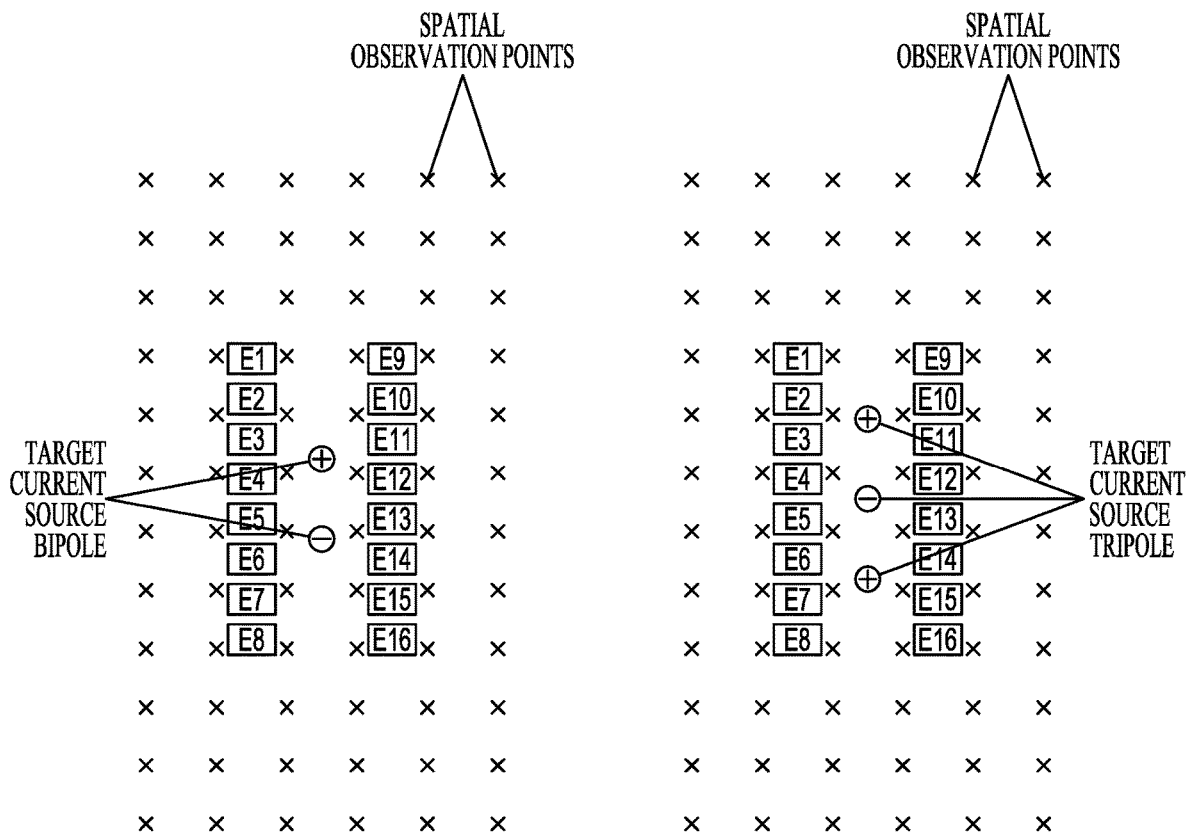
*FIG. 22A*  *FIG. 22B*
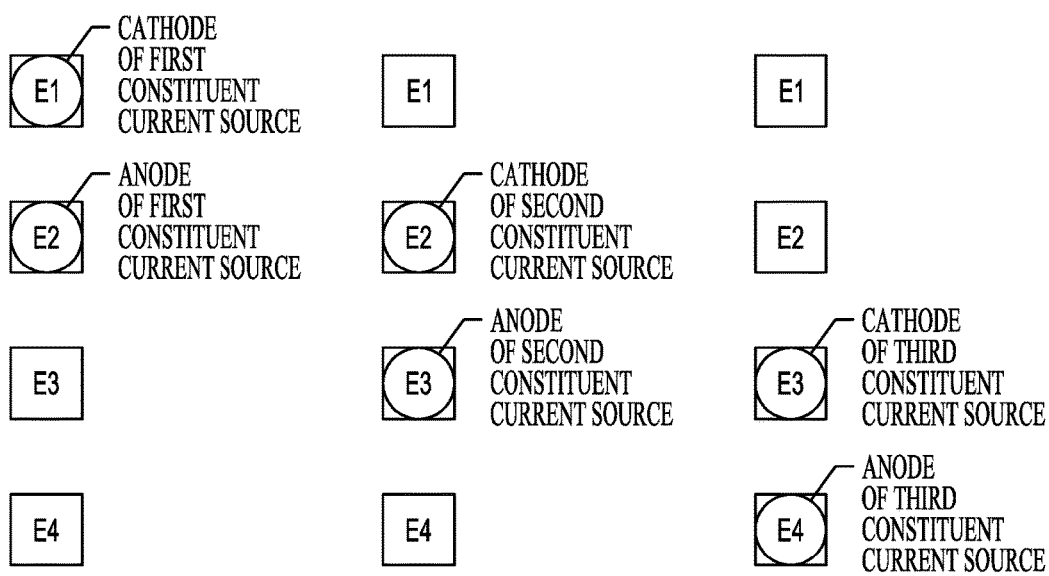
*FIG. 23A*  *FIG. 23B*  *FIG. 23C*

TRANSFER MATRIX A (m x n)

$$\begin{bmatrix} m \text{ field potential values due to constituent source \#1} & m \text{ field potential values due to constituent source \#2} & m \text{ field potential values due to constituent source \#3} & \cdots & m \text{ field potential values due to constituent source \#n} \end{bmatrix}$$

*FIG. 24*

SYSTEM AND METHOD FOR PROVIDING GLUCOSE CONTROL THERAPY

CLAIM OF PRIORITY

This application claims the benefit of priority under 35 U.S.C. § 119(e) of U.S. Provisional Patent Application Ser. No. 62/580,723, filed on Nov. 2, 2017, which is herein incorporated by reference in its entirety.

TECHNICAL FIELD

This document relates generally to medical devices, and more particularly, to systems, devices and methods used to provide glucose control.

BACKGROUND

Diabetes is a metabolic disease that is prevalent throughout the world. Diabetes is commonly treated pharmacologically. However, the pharmacological approach currently lacks precision in glucose control and has significant side effects such as hypoglycemia, gastrointestinal problems, peripheral edema, body weight increase etc. Furthermore, the patient compliance to the pharmacological treatment plan is relatively low, such that many patients do not reach their glycemic goals, which can negatively impact the patient's health and health care cost. Therefore, there is a need for better glycemic control.

SUMMARY

An example (e.g. "Example 1") of a system may include an implantable structure with a plurality of electrodes attached thereto, where the implantable structure is configured to be implanted proximate to a nerve that innervates and is proximate to an organ involved with glucose control. The system may further include a controller configured for use to control which of the plurality of electrodes are modulation electrodes and which of the plurality of electrodes are sense electrodes, a modulation energy generator configured to deliver modulation energy using one or more of the modulation electrodes, and a nerve traffic sensor configured to sense nerve traffic in the nerve using one or more of the sense electrodes. The controller may be configured to determine if the delivered modulation energy captures the nerves based on the sensed neural activity.

In Example 2, the subject matter of Example 1 may optionally be configured such that the structure is configured to be implanted proximate to a hepatic nerve proximate to a liver, a pancreatic nerve proximate a pancreas, or a celiac ganglia that has postganglionic axons that innervate the liver.

In Example 3, the subject matter of any one or any combination of Examples 1-2 may optionally be configured such that the structure includes at least one patch on a distal end of a lead.

In Example 4, the subject matter of any one or any combination of Examples 1-3 may optionally be configured such that the plurality of electrodes are arranged in an array of at least two columns and at least two rows on the at least one patch.

In Example 5, the subject matter of any one or any combination of Examples 1-4 may optionally be configured such that the at least one patch is configured to at least partially wrap around tissue that includes the nerve.

In Example 6, the subject matter of any one or any combination of Examples 1-5 may optionally be configured such that the structure further includes an implantable pulse generator integrated with the plurality of electrodes.

In Example 7, the subject matter of Example 1 may optionally be configured such that the system further includes a lead, where the structure includes a distal end of the lead, and the lead is configured to be intravascularly fed through an aorta into a hepatic artery.

In Example 8, the subject matter of Example 7 may optionally be configured such that the distal end of the lead is configured to expand to move the plurality of electrodes into contact with the hepatic artery.

In Example 9, the subject matter of Example 7 may optionally be configured such that the distal end of the lead is configured to puncture through a wall of the hepatic artery and at least partially wrap around the hepatic artery.

In Example 10, the subject matter of any one or any combination of Examples 1-2 may optionally be configured such that the structure is configured to be laparoscopically delivered for implantation proximate to the nerve.

In Example 11, the subject matter of any one or any combination of Examples 1-2 may optionally be configured such that the structure is configured to be percutaneously delivered for implantation proximate to the nerve.

In Example 12, the subject matter of any one or any combination of Examples 1-5 and 10-11 may optionally be configured such that the structure is an implanted passive structure, and an external waveform generator is configured to provide power for the implanted passive structure to generate modulation energy.

In Example 13, the subject matter of any one or any combination of Examples 1-12 may optionally be configured such that the diabetic therapy delivery system is configured to deliver neuromodulation for graded glucose control, and the neuromodulation includes a neural block or neural stimulation.

In Example 14, the subject matter of Example 13 may optionally be configured such that the neuromodulation includes a depletion block.

In Example 15, the subject matter of any one or any combination of Examples 1-14 may optionally be configured such that the diabetic therapy delivery system includes multiple independent current sources to independently deliver current to two or more of the modulation electrodes, where each of the multiple independent current sources is configured to source or sink current, and each of the multiple independent current sources including a PDAC (digital-to-analog converter circuitry with P-type transistors) configured for use to source current and an NDAC (digital-to-analog converter circuitry with N-type transistors) configured for use to sink current.

An example (e.g. "Example 16") of a method may provide a glucose control therapy using a lead with multiple electrodes operably positioned proximate to nerves that innervate and are proximate to an organ involved with glucose control. The method may include selecting one or more modulation electrodes from the multiple electrodes for use to deliver modulation energy and selecting one or more sense electrodes from the multiple electrode for use to sense neural activity in the nerves, delivering modulation energy using the selected one or more modulation electrodes, sensing neural activity in the nerves using the selected one or more sense electrodes, and determining if the delivered modulation energy captures the nerves based on the sensed neural activity.

In Example 17, the subject matter of Example 16 may optionally be configured such that the nerves include a hepatic nerve that innervates and is proximate to a liver.

In Example 18, the subject matter of any one or any combination of Examples 16-17 may optionally be configured such that the nerves include a pancreatic nerve that innervates and is proximate to a pancreas.

In Example 19, the subject matter of any one or any combination of Examples 16-18 may optionally be configured such that the lead includes at least one distal patch configured to wrap at least partially around tissue including the nerves, the multiple electrodes being on the at least one distal patch.

In Example 20, the subject matter of Example 19 may optionally be configured such that the method includes wrapping the at least one distal patch around a hepatic vessel and hepatic nerves.

In Example 21, the subject matter of Example 19 may optionally be configured such that the lead includes two or more patches.

In Example 22, the subject matter of Example 19 may optionally be configured such that the multiple electrodes on the at least one patch are arranged in an electrode array of at least two rows of electrodes and at least two columns of electrodes.

In Example 23, the subject matter of Example 19 may optionally be configured such that the lead is configured to be intravascularly fed into position proximate to the nerves.

In Example 24, the subject matter of Example 23 may optionally be configured such that the lead is configured to be intravascularly fed through an aorta into a hepatic artery to position the lead proximate to a hepatic nerves.

In Example 25, the subject matter of Example 23 may optionally be configured such that a distal portion of the intravascularly-fed lead is configured to puncture through the hepatic artery and at least partially wrap around the hepatic artery.

In Example 26, the subject matter of Example 23 may optionally be configured such that a distal portion of the intravascularly-fed lead is configured to expand to abut against a wall of the hepatic artery.

In Example 27, the subject matter of Example 23 may optionally be configured such that the method includes laparoscopically, percutaneously, or surgically positioning the lead proximate to the nerve.

In Example 28, the subject matter of Example 23 may optionally be configured such that the method includes using multiple independent current sources to independently deliver current to two or more of the modulation electrodes.

In Example 29, the subject matter of Example 28 may optionally be configured such that each of the multiple independent current sources is configured to source or sink current, each of the multiple independent current sources including a PDAC configured for use to source current and an NDAC configured for use to sink current.

In Example 30, the subject matter of Example 29 may optionally be configured such that the method further includes controlling current contributions of each of the modulation electrodes to form at least one target pole within a tissue region that includes the nerves, and implementing a mapping process. The mapping process may include modifying the current contributions from each of the modulation electrodes to move the at least one target pole through different positions in the tissue region, sensing neural activity in the nerves using the one or more sensed electrodes when the at least one target pole is in each of the different positions, and determining if the delivered modulation energy using the at least one target pole at each of the different positions captures the nerves based on the sensed activity in the nerves.

In Example 31, the subject matter of Example 29 may optionally be configured such that the mapping process further includes sensing a physiological response, and using the sensed physiological response to determine if the modulation energy is capturing a sympathetic nerve or a parasympathetic nerve.

In Example 32, the subject matter of Example 2.9 may optionally be configured such that the mapping process further includes implementing a capture threshold detection process when the at least one target pole is in each of the different positions, the capture threshold detection process including testing different values for a modulation parameter and sensing neural activity for each of the different values to determine a threshold modulation parameter value for causing neural activity in the nerves.

In Example 33, the subject matter of Example 32 may optionally be configured such that the method further includes using the threshold modulation parameter value to set a modulation parameter value for a graded neuromodulation therapy.

In Example 34, the subject matter of Example 32 may optionally be configured such that the threshold modulation parameter value controls current contribution amplitudes of the modulation electrodes.

In Example 35, the subject matter of Example 29 may optionally be configured such that the mapping process further includes sensing a physiological response, and using the sensed physiological response to determine if the modulation energy is capturing a sympathetic nerve or a parasympathetic nerve, implementing a capture threshold detection process when the target pole is in each of the different positions, the capture threshold detection process including testing different values for a modulation parameter and sensing neural activity for each of the different values to determine a threshold modulation parameter value for causing neural activity in the nerves, and recording, for each of the different positions of the target pole, whether the modulation energy is capturing the sympathetic nerve or the parasympathetic nerve, and the threshold modulation parameter value.

An example (e.g. "Example 36") may include a non-transitory machine-readable medium including instructions, which when executed by a machine operably connected to electrodes, cause the machine to perform any of the methods recited in Examples 16-35.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 14A and 4B illustrate, by way of example, lead embodiments configured to wrap around blood vessels and/or nerves.

FIGS. 22A-22B illustrate a target electrical field mapped to the electrode array by estimating the field potential values (or some other linear electrical parameter, such as an activating function, current density, etc.) of the target field at a plurality of spatial observation points.

FIGS. 23A-23C illustrate, by way of example, constituent current sources at the locations of the electrodes.

FIG. 24 illustrates an m×n transfer matrix for estimating contributions of the constituent current sources from estimated field potentials.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. Further, the use of "and/or" may refer to "at least one of", such that A and/or B refers to at least one of A or B, which may also be described as "A", "B", or "A and B". The following detailed description is, therefore, not to be taken in a limiting sense, and the scope is defined only by the appended claims, along with the full scope of legal equivalents to which such claims are entitled.

Various embodiments described herein involve treatments that can provide tailored, patient-specific glycemic control. For example, various embodiments may address patient compliance challenges as the treatment does not rely on a patient taking pharmaceuticals. The tailored, patient-specific glycemic control may avoid common complications such as hypoglycemia.

Physiologic glucose levels in diabetic patients may be maintained by manipulating the hepatic glucose production and/or by manipulating pancreatic secretions. Various embodiments described herein may modulate neural targets that innervate the liver and/or neural targets that innervate the pancreas. Modulation of neural targets may include eliciting action potentials or inhibiting action potentials in the neural targets. Under normal physiological conditions, hepatic glucose production is controlled by sympathetic and parasympathetic branches of the hepatic nerve. Hepatic glucose production may be decreased by stimulating the hepatic parasympathetic nerves and/or inhibiting the hepatic sympathetic nerves; and hepatic glucose production may be increased by inhibiting the hepatic parasympathetic nerves and/or stimulating the hepatic sympathetic nerves.

Figure 1:
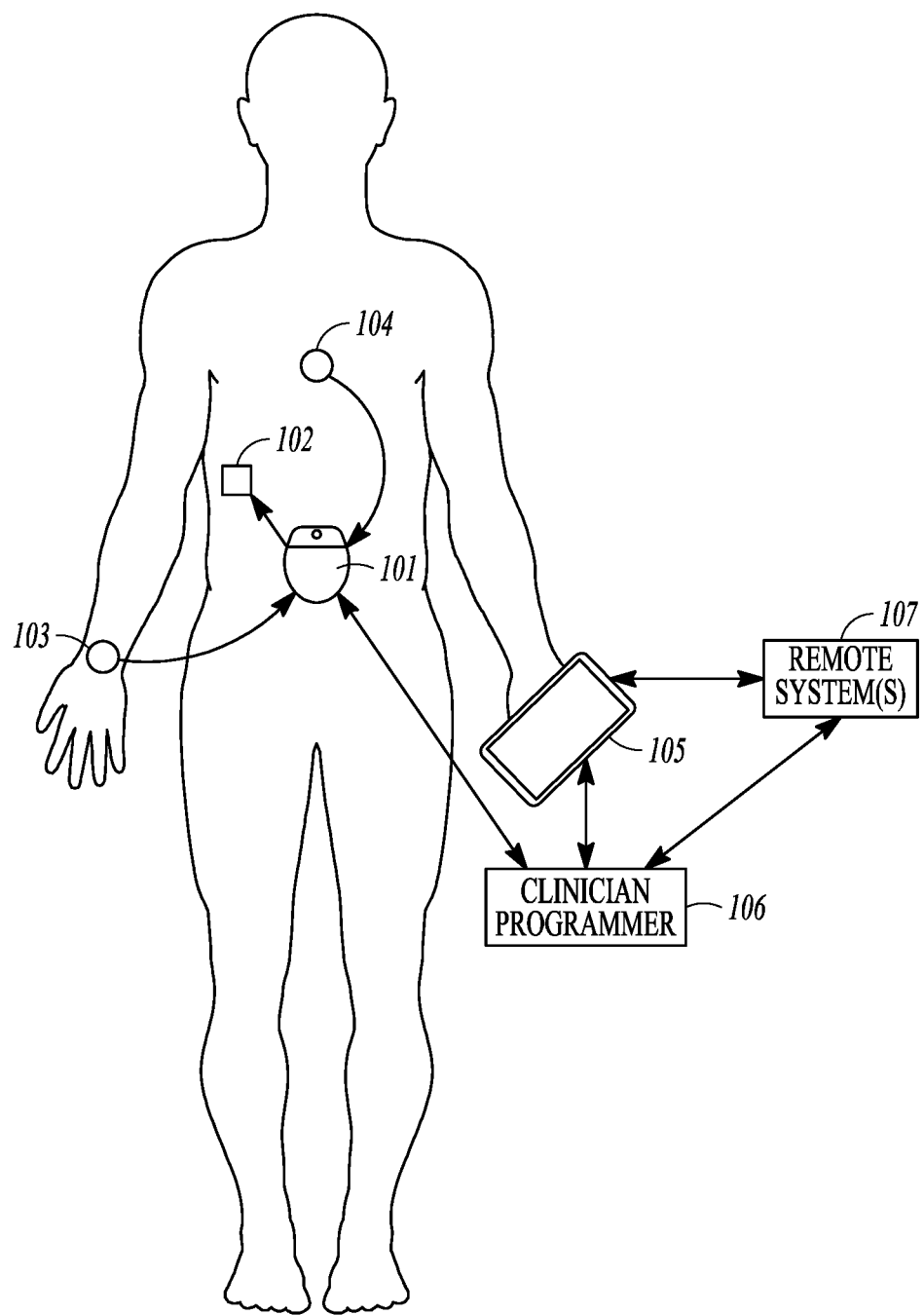
FIG. 1 illustrates, by way of example, an embodiment of a neuromodulation system to provide glycemic control.

FIG. 1 illustrates, by way of example, an embodiment of a neuromodulation system to provide glycemic control. The illustrated system 100 includes a neuromodulator 101 configured to be implanted to deliver neuromodulation energy to the neural target 102.

Various neuromodulation therapies may stimulate action potentials using electrical stimulation at frequencies generally less than 50 Hz, with pulse widths generally in the range of 50 to 1000 μs, and amplitudes less than 10 mA. Various neuromodulation therapies may reversibly block action potentials using a depletion block. The depletion block may be implemented using electrical stimulation frequencies generally within the range of 100-1,000 Hz (e.g. 100-700 Hz, or 100-500 Hz), with pulse widths generally between 50 and 500 μs, and amplitudes less than 10 mA for depletion block. The depletion block causes depletion of the neurotransmitter by eliciting action potentials faster than the nerve can respond. Various neuromodulation therapies may reversibly block action potentials using a conduction block. The conduction block may be implemented using electrical stimulation frequency in the range of 1 kHz to 50 kHz (e.g. 1-10 kHz, 2-10 kHz, or 5-10 kHz) with pulse widths generally between 10 and 100 μs and amplitudes less than 50 mA for conduction block. Additionally or alternatively, substantially higher frequencies, greater than 50 kHz, such as 480 kHz used by pulsed radiofrequency ablation systems, may be delivered to the target nerves for longer-lasting clinical effects (i.e. effects that are reversible after a prolonged period of time, e.g. after 1 day, 3 days, 7 days, or longer, up to several months). Various neuromodulation therapies may stimulate action potentials using electrical stimulation at frequencies generally less than 50 Hz, with pulse widths generally in the range of 50 to 1000 us, and amplitudes less than 10 mA.

Neural targets for the neuromodulation therapy may include the hepatic branch of the vagus nerve, the vagus nerve, the splanchnic nerve, the sympathetic branch of the hepatic nerve. Electrodes may be laparoscopically or intravascularly delivered into position for use to modulate the neural targets. For example, electrodes may be operably placed proximate to or inside of the common hepatic artery, hepatic artery proper, right hepatic artery and/or left hepatic artery.

The system 100 may include sensor(s), such as but not limited to an activity sensor 103 or a physiological sensor 104 such as glucose sensor. A number of sensors may be used, as disclosed throughout this disclosure. One or more sensors (implantable or non-invasive) may be integrated with or otherwise in communication with the neuromodulator. Examples of sensors may include blood glucose sensor, interstitial fluid glucose sensors, and insulin sensors. These sensors may be used for closed-loop control. Other sensors may be used, such as sensors to detect amino acid concentration, glucagon, cortisol, progesterone/estrogen, norepinephrine/epinephrine, leptin, fatty acids/triglycerides, GLP-1, CCK, K+, Ca2+, Na+, Cl−, blood pH, interstitial fluid pH, activity levels (e.g. accelerometer data), respiratory rate, heart rate, blood pressure or a surrogate of blood pressure that may be used to quantify stress, which increases hormone levels), hydration levels from blood flow via photoplethysmography or electrical bioimpedance, neural activity or evoked compound action potentials such as may be detected on parasympathetic or sympathetic nerve fibers.

Figure 2A:
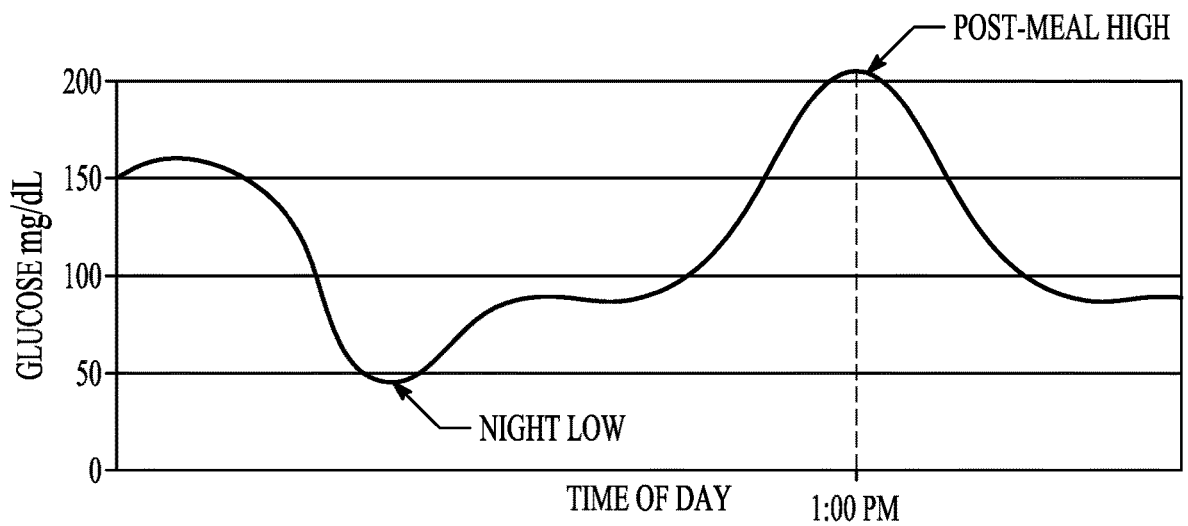
FIG. 2A illustrates, by way of example, an uncontrolled glucose level.
Figure 2B:
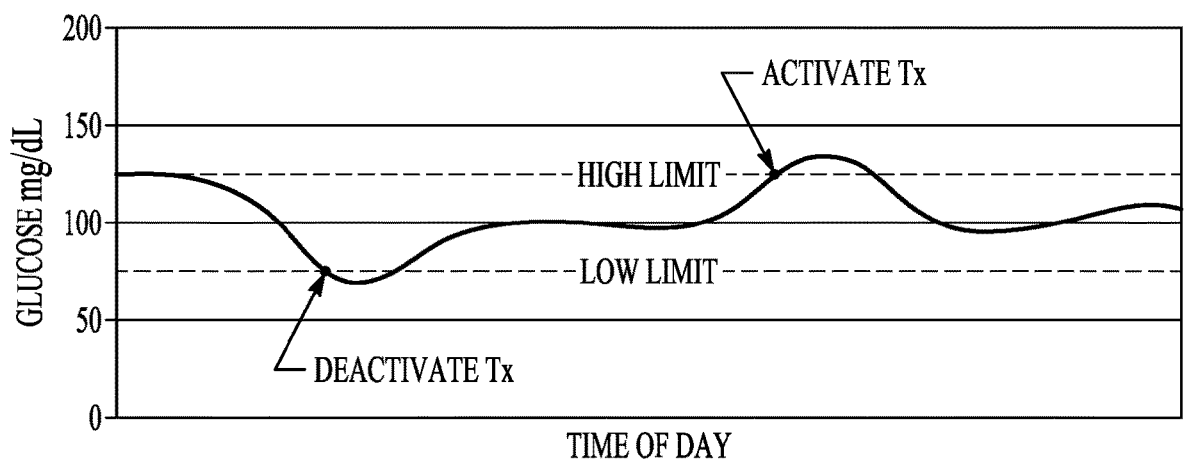
FIG. 2B illustrates, by way of example, a controlled glucose level using a neuromodulation therapy.

The system may be used to transform uncontrolled glucose levels into controlled glucose levels. FIG. 2A illustrates, by way of example, an uncontrolled glucose level; and FIG. 2B illustrates, by way of example, a controlled glucose level using a neuromodulation therapy. The uncontrolled glucose level illustrated in FIG. 2A may be characterized by hypoglycemic episodes such as night-time lows, and hyperglycemic episodes such as post-meal highs. By way of example and not limitation, the system illustrated in FIG. 1 may activate a neuromodulation therapy or change to a different mode of therapy delivery when the glucose level crosses an upper threshold. The system may deactivate a neuromodulation therapy or change to a different mode of therapy delivery if when the glucose level crosses a lower threshold. As will be evident to one of ordinary skill in the art upon reading and comprehending this disclosure, the therapy control may be based on an absolute value of a measured parameter (e.g. blood glucose of 130 mg/dl), may be based on a rate of change in the measured parameter, or a combination of the value and the rate of change. As will also be evident to one of ordinary skill in the art upon reading and comprehending this disclosure, the therapy control may be based, at least in part, on other inputs such as activity, diet, etc.

As illustrated in FIG. 1, the system may include one or more external devices, such as a patient device 105, a clinician programmer 106 and/or remote system(s) 107. The patient device 105 may function as a monitor, a remote control to control the therapy initiation, therapy termination, or therapy scheduling as discussed in more detail below. The patient device may also include a patient-facing interface for use by the patient to input data such as glucose levels, activity, or other information. The patient-facing interface may be used by a patient to provide inputs such as meal start time and carbohydrates in meal. Other inputs may include exercise time, sleep time, medication intake and time, alcohol intake, or menstruation information. A processor may use one or more of these input signals as an input to control stimulation parameters. The processor may use the time of day to determine normal daily patient trends as an input to control stimulation parameters.

The clinician programmer 106 may be used within a clinical setting to program modulation parameters in the neuromodulator to cause the electrical energy to modulate the neural target. Also, the clinician programmer 106 may communicate with the patient device 105. In some embodiments, the patient device may be programmed by the clinician programmer. The patient device 105 and/or the clinician programmer 106 may communicate with remote systems(s) 107 that may be used to store or analyze patient-specific data or patient population data. Machine learning (also referred to as Artificial Intelligence or AI) may be implemented on patient-specific and/or patient population data to refine and improve upon the therapeutic response to various inputs. For example, AI may learn from the patient's typical daily activities over the course of days, weeks or months, and may use the patient's typical glucose levels, and/or dietary intake patterns as inputs for the automatically applied therapy. External system(s) may be used to program or update application(s) on the patient device 105 or clinician programmer 106.

The neuromodulation therapy system may operate in a manual mode, may operate in an automatic mode, and/or may operate in a semi-automatic mode. When the system is operating in a manual mode, the patient may be able to control the therapy using an external patient device 105 such as a handheld device. When the system is operating in an automatic mode, the system may deliver closed-loop therapy based on sensor data. By way of example, the neuromodulation therapy may be activated, deactivated, or delivered in a graded manner. Sensed glucose levels may be used as a therapy input. For example, the target mean glucose level (e.g. 120 mg/dL) may be used as an input. However, a range of glucose levels between a low glucose threshold and a high glucose threshold may be acceptable. Example of low glucose thresholds may be within a range between 50 and 100 mg/dL. Examples of high glucose thresholds may be within a range between 140 and 170 mg/dL. A graded therapy may use patient activity as an input for the neuromodulation therapy. The patient activity may be input by a person such as the patient or other user, or may be sensed by an activity sensor. Examples of activity sensors 103 may include an accelerometer, a gyroscope, a GPS sensor, a cardiovascular activity sensor, a respiratory sensor, or any other activity tracker or combination thereof. When the system is operating in a semi-automatic mode, an alert may be delivered to an external device (e.g. patient device 105 or clinician programmer 106), and the user (e.g. patient or clinician) may choose whether to take action on the alert.

Various embodiments may provide therapy titration by enabling the system to determine which electrodes to use for sympathetic and/or parasympathetic modulation. For example, some electrodes may be used to modulate a neural target, and other electrodes may be used to sense for neural activity in another neural target. Thus, for example, some embodiments sense for action potential in a neural target to determine if the neuromodulation using other electrodes are causing a complete or graded block, which can then be used to adjust the setting of the neuromodulation. For example, where the neuromodulation therapy involves inhibiting sympathetic fibers, the sensing electrodes may be used to monitor naturally-occurring action potentials to determine how well the neuromodulation is inhibiting those action potentials. Where the neuromodulation therapy involves activating action potentials in the parasympathetic fibers, the sensing electrodes could be used to detect and in some embodiments measure the number of action potentials that are generated downstream. The sensing electrodes may be useful to determine appropriate settings (amplitude or timing/duty cycle) for obtaining a more graded therapy. Where the modulation is delivered to an efferent neural pathway, the sensing may occur on the efferent or afferent neural pathway. Similarly, where the modulation is delivered to an afferent neural pathway, the sensing may occur on the efferent or afferent neural pathways.

Various embodiments may include a closed-loop implantable neuromodulation system to regulate hepatic glucose production that activates or deactivates neural activity and/or provides a graded level of therapy based on patient-specific data or input. Closed-loop control may be delivered, for example, via communication between the implantable neuromodulation system and a glucose monitoring system. Further, various embodiments of the system may include a controller with software applications operating on thereon, and an interface that shows real-time patient data and therapy settings. In various embodiments, the neuromodulation therapy includes blocking sympathetic fibers of the hepatic nerves to inhibit glycogenolysis. In various embodiments, the neuromodulation therapy includes stimulating parasympathetic nerve to stimulate glucose uptake and hepatic glycogen deposition.

Figure 3:
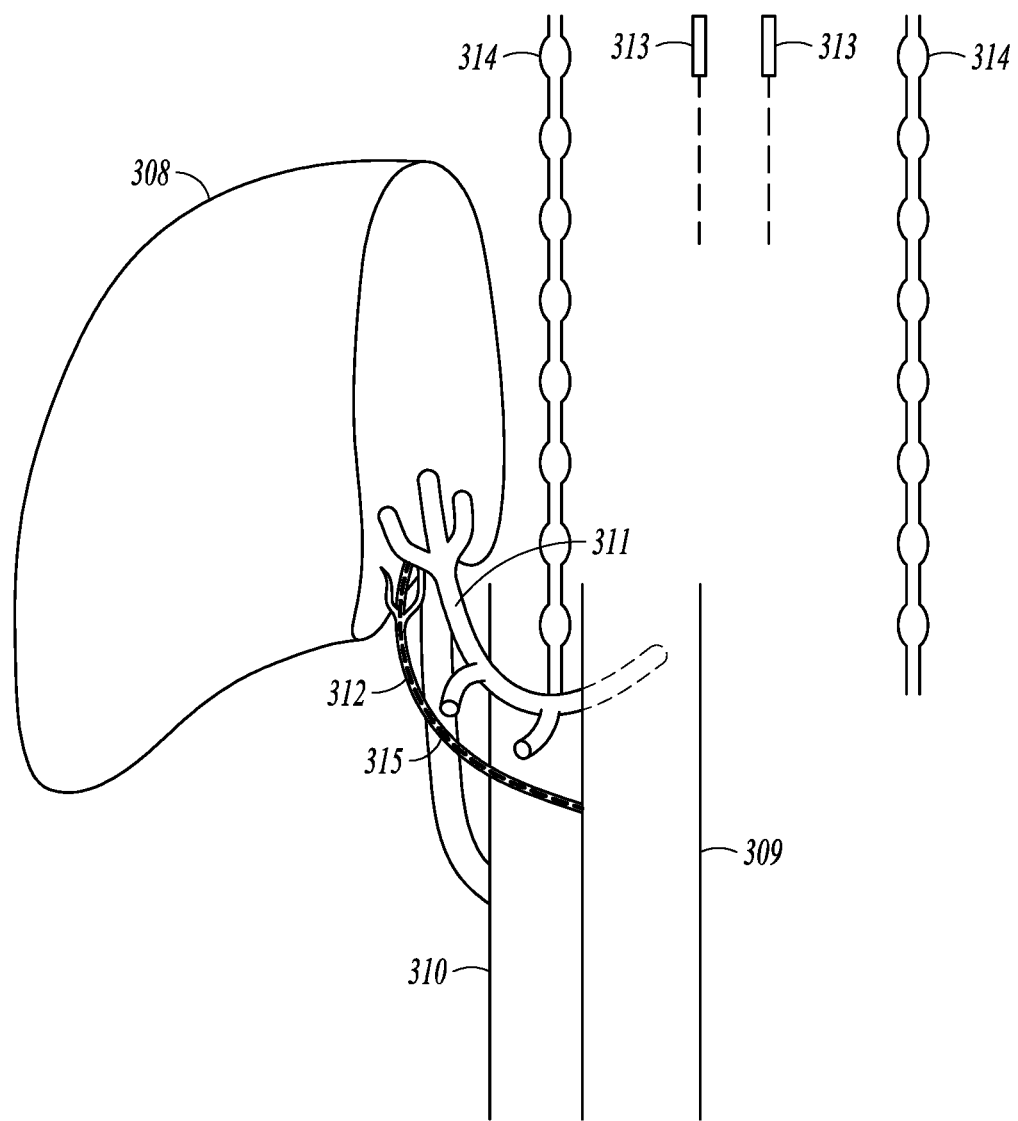
FIG. 3 illustrates, by way of example, some hepatic neural targets for a neuromodulation therapy.

FIG. 3 illustrates, by way of example, some hepatic neural targets for a neuromodulation therapy. The illustration shows a portion of the liver 308, aorta 309 and inferior vena cava 310. A hepatic artery 311 extends from the aorta 309 to the liver 308, and a port vein 312 extends from the liver 308 to the inferior vena cava 310. Vagus nerves 313 and sympathetic nerve trunks 314 are also illustrated. The hepatic region includes a hepatic branch 315 of the vagus nerve, and further includes hepatic nerves around the hepatic artery 311. The hepatic nerves may include a region of mixed sympathetic and parasympathetic nerves, and another region of predominately sympathetic nerves.

A multi-electrode lead and/or more than one lead, or an implantable neuromodulator with integrated electrodes, may be delivered to region of parasympathetic and/or sympathetic innervation to the liver. Both parasympathetic and sympathetic nerves may be independently stimulated and/or inhibited. Therapy may be delivered concurrently to parasympathetic and sympathetic nerves according to some embodiments. Multi-electrode leads and multiple independent current control may be used to precisely deliver electrical current to specifically target the nerve fibers around the vessels. This may be particularly beneficial as both parasympathetic and sympathetic nerves are present around the hepatic artery and may be proximate and intermixed with each other. Some embodiments may measure the output (e.g. glucose levels) and systemically stimulate and inhibit between various electrode pairs until the optimal therapy parameters are identified. Closed-loop machine learning algorithms may be utilized to continue therapy titration over time (chronically). Various embodiments may modulate distal neural targets (e.g. neural targets relatively near the liver or pancreas), and may modulate more proximal targets further away from the liver or pancreas. Sympathetic targets may include at least one of the following targets: celiac ganglia, celiac plexus, sympathetic chain between T10 and L2, dorsal root ganglia between T10 to L2, mesenteric ganglia, pancreatic plexus, hepatic plexus, or splanchnic nerve. Parasympathetic targets may include at least one of the following targets: vagus nerve, hepatic branch of the vagus nerve, or pancreatic branch of the vagus nerve.

Various embodiments may titrate the neuromodulation therapy using physiological markers that correlate with autonomic (parasympathetic/sympathetic) tone. For example, different modulation vectors (e.g. current between a different combinations of electrodes) may be tested by monitoring physiological markers when each of the combinations is tested. The duration of each test may be five or more minutes. Various markers of autonomic tone may be used as the monitored physiological marker(s). Examples of such markers include, but are not limited to, heart rate, heart rate variability (HRV), galvanic skin response (GSR), photoplethysmography (PPG), pulse rate variability, blood pressure, pulse transit time and pulse wave amplitude as alternative measures for blood pressure, respiration rate, pupil diameter, respiratory sinus arrhythmia, baroreceptor sensitivity, and normalized pulse volume (NPV). Chemical markers may be used to titrate the therapy. Examples of such chemical markers include but are not limited to norepinephrine and acetylcholine. Various embodiments may use electrode impedance measurements to optimize electrode selection and monitor tissue.

The medical device may be an implantable neuromodulator configured to stimulate and/or block the parasympathetic and/or sympathetic portions of the hepatic nerve to control hepatic glucose production. The medical device may be used to deliver a therapy for any condition requiring the regulation of blood glucose levels. For example, the therapy may treat diabetes. Other conditions that may be treated may include insulin resistance, genetic metabolic disease, hyperglycemia, obesity, hyperlipidemia, hypertension, endocrine diseases and/or inflammatory disorders.

The stimulation and/or blocking therapy may be delivered in the form of electrical energy, magnetic energy, sound energy (e.g. ultrasound), light energy (e.g. laser energy, infrared energy, etc. including photodynamic therapy) and/or heat energy, amongst other modalities.

The stimulation may be in a form of stimulation pulses that are characterized by pulse amplitude, pulse width, stimulation frequency, duration, on-off cycle, pulse shape or waveform, temporal pattern of the stimulation, among other stimulation parameters. Examples of the stimulation pattern may include burst stimulation with substantially identical inter-pulse intervals, or ramp stimulation with incremental inter-pulse intervals or with decremental inter-pulse intervals. In some examples, the frequency or the pulse width may change from pulse to pulse.

Figure 4A:
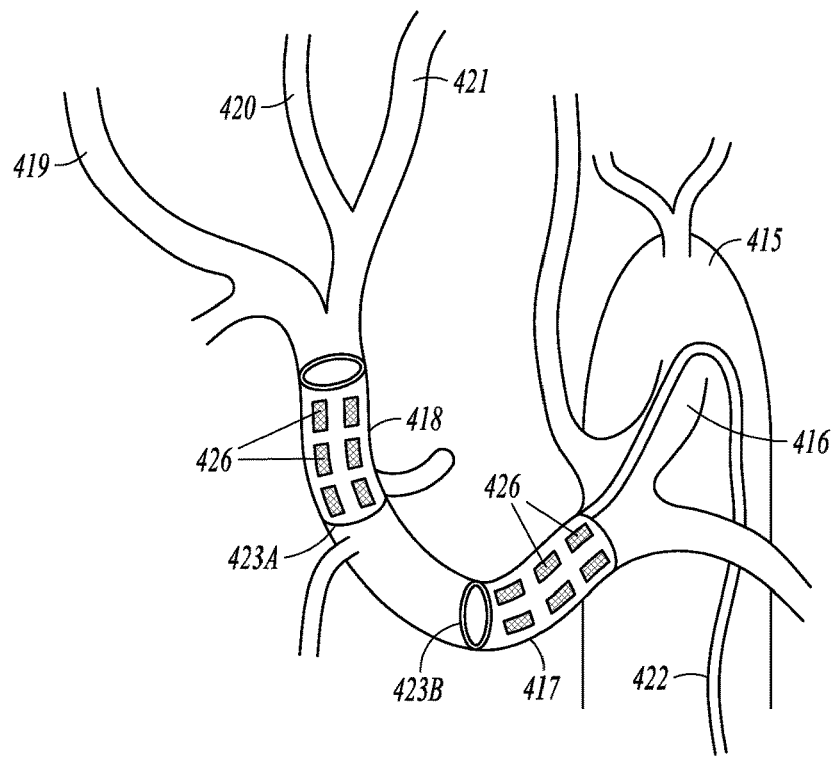
FIGS. 4A-4B illustrate, by way of example, intravascularly-delivered leads used to provide neuromodulation to hepatic neural targets.
Figure 4B:
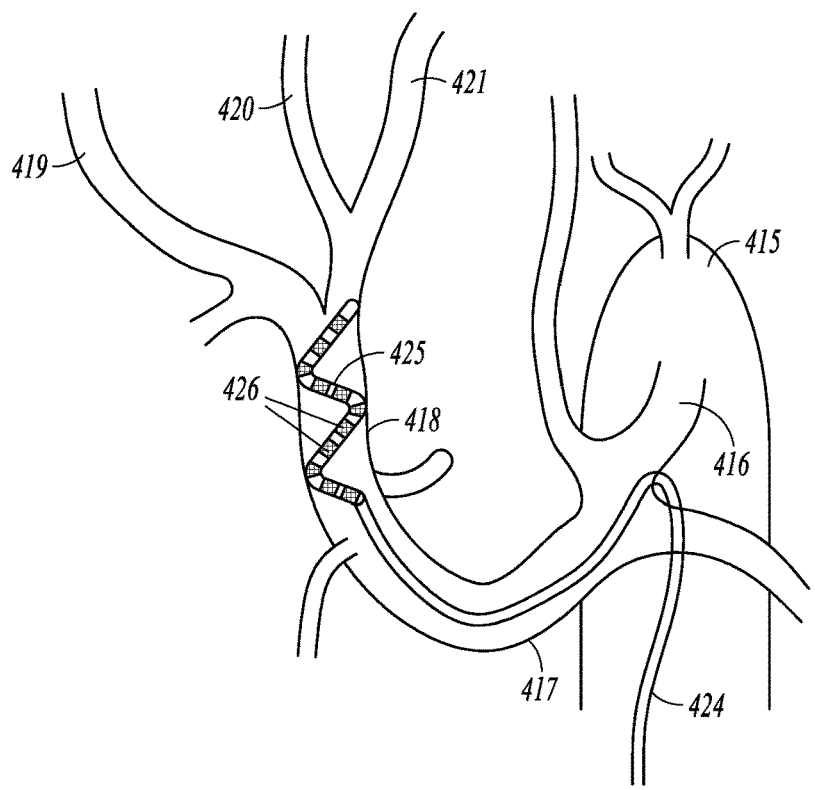

FIGS. 4A-4B illustrate, by way of example, intravascularly-delivered leads used to provide neuromodulation to hepatic neural targets. Those of ordinary skill in the art will understand that similar intravascular leads may be used to target pancreatic nerves. The illustrated vasculature includes an aorta 415, a celiac trunk 416, a common hepatic artery 417, and a proper hepatic artery 418 which branches off into the right 419, middle 420 and left 421 hepatic arteries. FIG. 4A illustrates an intravascularly delivered multi-electrode lead 422 with an expandable electrode portion 423A that can be expanded in the proper hepatic artery 418 to target mixed parasympathetic and sympathetic neural targets proximate to the proper hepatic artery and another expandable electrode portion 423B that can be expanded in the common hepatic artery 417 to target predominately sympathetic neural targets that are proximate to the common hepatic artery. The lead 422 may be fed through the aorta 415 and celiac trunk 416 into the common hepatic artery 417 and proper hepatic artery 418. FIG. 4B also illustrates an intravascularly delivered multi-electrode lead 424 that may be fed through the aorta 415 and celiac trunk 416 into the common hepatic artery 417 and proper hepatic artery 418. The distal end of the lead 424 includes a coiled electrode portion 425 with a shape memory configured to expand against the inner arterial walls when the guide catheter is withdrawn. As illustrated, both leads may include multiple electrodes 426 to provide a desired modulation field to modulate targeted nerves.

Figure 5:
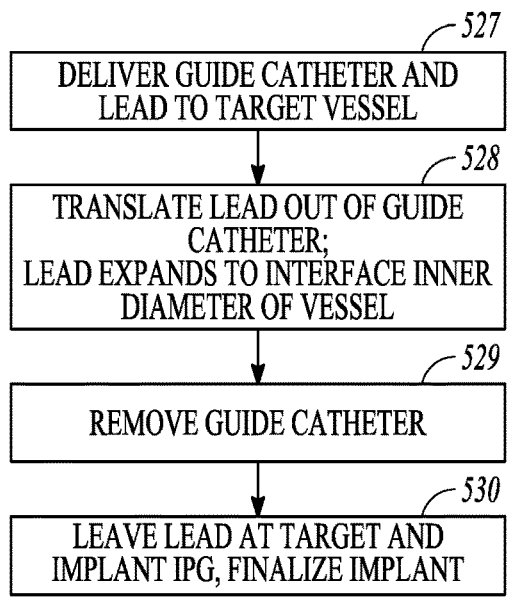
FIG. 5 illustrates, by way of example, a process for using a guide catheter and expandable lead to intravascularly deliver a neuromodulation lead.
Figure 6A:
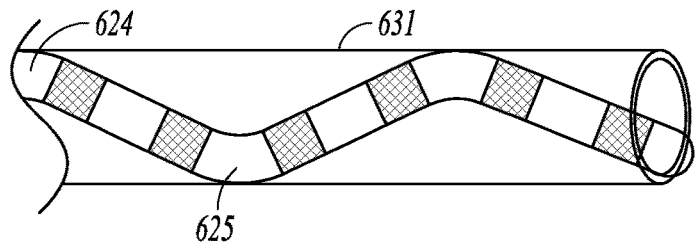
FIGS. 6A-6B illustrate, by way of example, implantation of the neuromodulation lead using the process illustrated in FIG. 5.
Figure 6B:
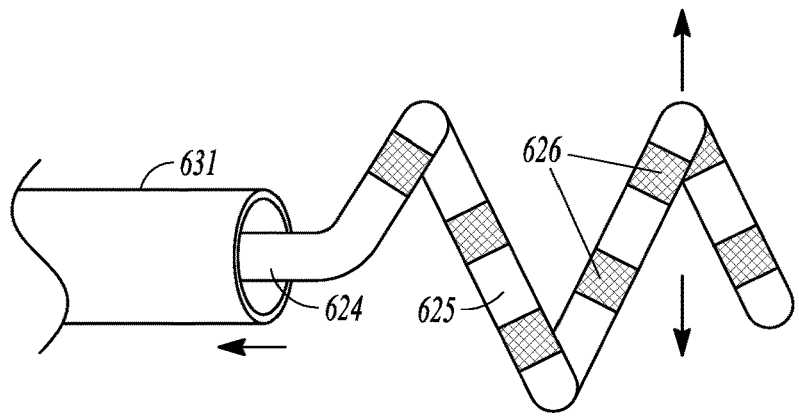

FIG. 5 illustrates, by way of example, a process for using a guide catheter and expandable lead to intravascularly deliver a neuromodulation lead with expandable stent-like electrode portions; and FIGS. 6A-6B illustrate, by way of example, implantation of the neuromodulation lead using the process illustrated in FIG. 5. The illustrated method includes, at 527, delivering a guide catheter 631 and lead 624 (see FIG. 6A) into the vascular proximate to the targeted neural tissue. At 528, the lead 624 is translated out of the guide catheter 631 to allow a coiled electrode portion 625 to expand to interface the inner diameter of the blood vessel (e.g. proper hepatic artery or common hepatic artery). The guide catheter is removed at 529 leaving the lead 624 in position for use to modulate the neural target using electrodes 626 on the coiled electrode portion 625 as illustrated at 530 and in FIG. 6B. The method illustrated in FIGS. 5, 6A and 6B may be used to deploy the lead illustrated in FIG. 4B.

Figure 7:
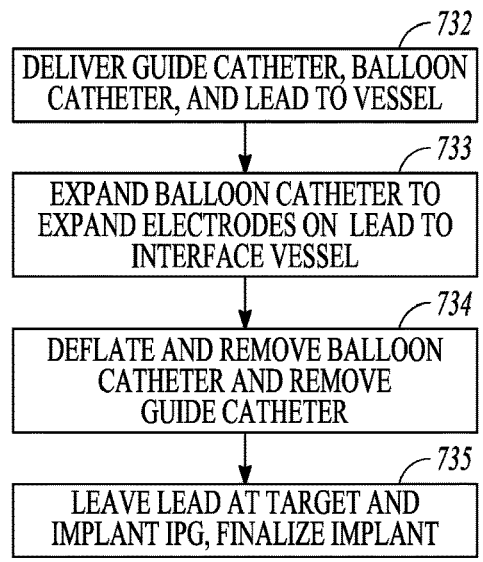
FIG. 7 illustrates, by way of example, a process for using a balloon catheter to intravascularly deliver a neuromodulation lead.
Figure 8A:
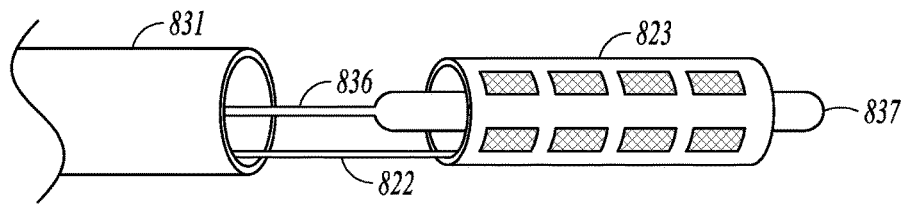
FIGS. 8A-8C illustrate, by way of example, implantation of the neuromodulation lead using the process illustrated in FIG. 7.
Figure 8B:
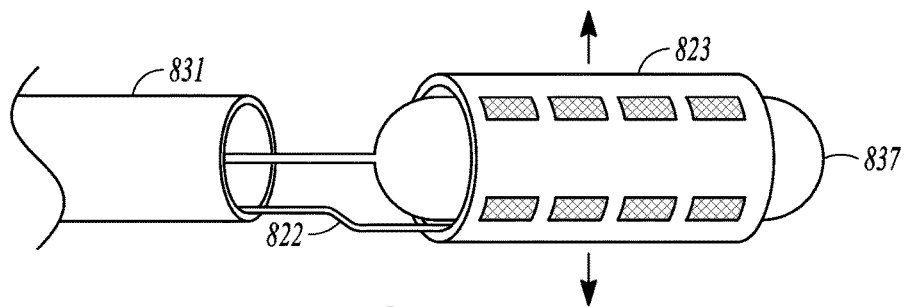
Figure 8C:
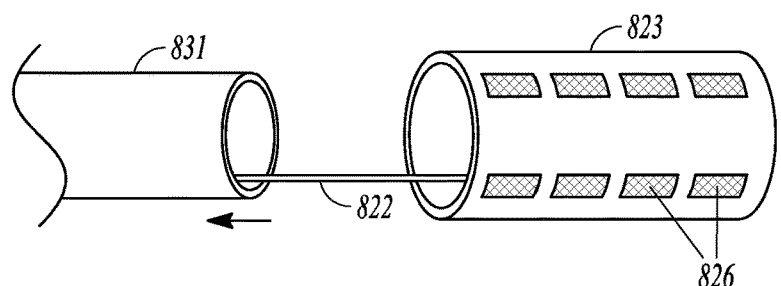

FIG. 7 illustrates, by way of example, a process for using a balloon catheter to intravascularly deliver a neuromodulation lead; and FIGS. 8A-8C illustrate, by way of example, implantation of the neuromodulation lead using the process illustrated in FIG. 7. The illustrated method includes, at 732, delivering a guide catheter 831, a balloon catheter 836 and lead 822 (see FIG. 8A) into the vascular proximate to the targeted neural tissue. A distal portion of the balloon catheter 836 has an inflatable balloon portion 837 that fits within the expandable electrode portion 82.3 at the distal end of the lead 822. When the expandable electrode portion 823 is at a desired implant location for use to modulate targeted nerves, the balloon portion 837 of the balloon catheter is inflated to expand the electrode portion 823, as illustrated at 733 and in FIG. 8B. As illustrated at 734 and 735 and FIG. 8C, the balloon portion 837 may be deflated, and both the guide catheter 831 and balloon catheter removed, leaving the lead at the desired implant location for use to modulate targeted nerves using electrodes 826 on the expandable electrode portion 823. The method illustrated in FIGS. 7,8A, 8B and 8C may be used to deploy the lead illustrated in FIG. 7.

Figure 9:
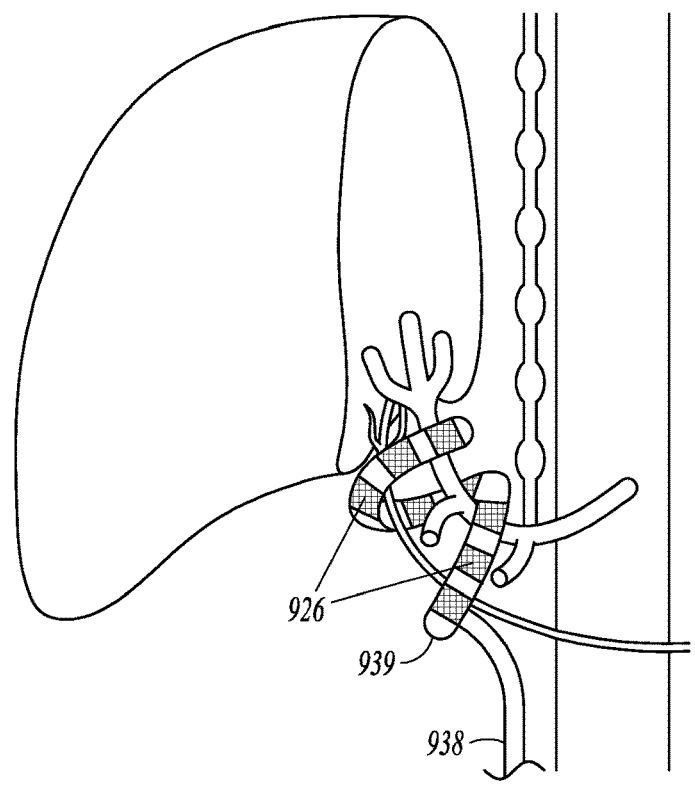
FIG. 9 illustrates, by way of example, a lead with a distal electrode portion wrapped around hepatic neural targets where the lead may be delivered laparoscopically, percutaneously or surgically.
Figure 10:
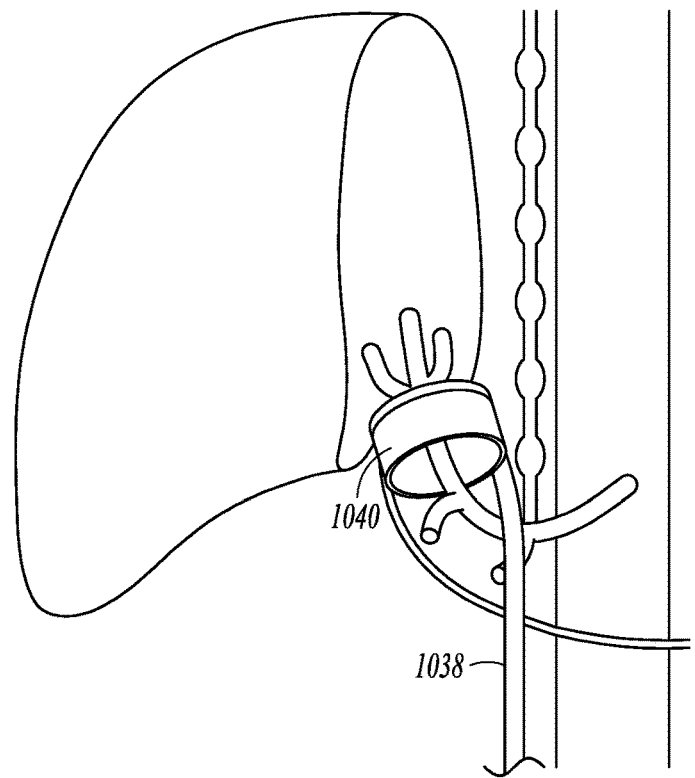
FIG. 10 illustrates, by way of example, a lead with a distal cuff wrapped around hepatic neural targets where the lead may be delivered laparoscopically, percutaneously or surgically.

FIG. 9 illustrates, by way of example, a lead with a distal electrode portion wrapped around hepatic neural targets where the lead may be delivered laparoscopically, percutaneously or surgically. The lead 938 has a coiled distal portion 939 configured to be wrapped at least partially around hepatic vasculature and/or neural targets in the hepatic region. The illustrated coiled distal portion is configure to wrap more than 360 degrees (e.g. about 540 degrees) around the neural targets. The neural targets may include a hepatic branch of the vagus nerve, and/or hepatic nerves around the hepatic artery. The coiled distal portion 939 includes electrodes 926 that may be used to deliver modulation energy to the neural target(s), FIG. 10 illustrates and example of a lead 1038 with a distal electrode cuff 1040 configured to be wrapped at least partially around hepatic vasculature and/or neural targets in the hepatic region. A plurality of electrodes may be inwardly facing from the cuff toward the targeted neural tissue. According to some embodiments, current delivered from each of the electrodes may be independently controlled. The lead may be delivered laparoscopically, percutaneously or surgically. A percutaneous procedure refers to a process for pacing the lead through skin and other tissue into position near the targeted neural tissue.

Figure 11:
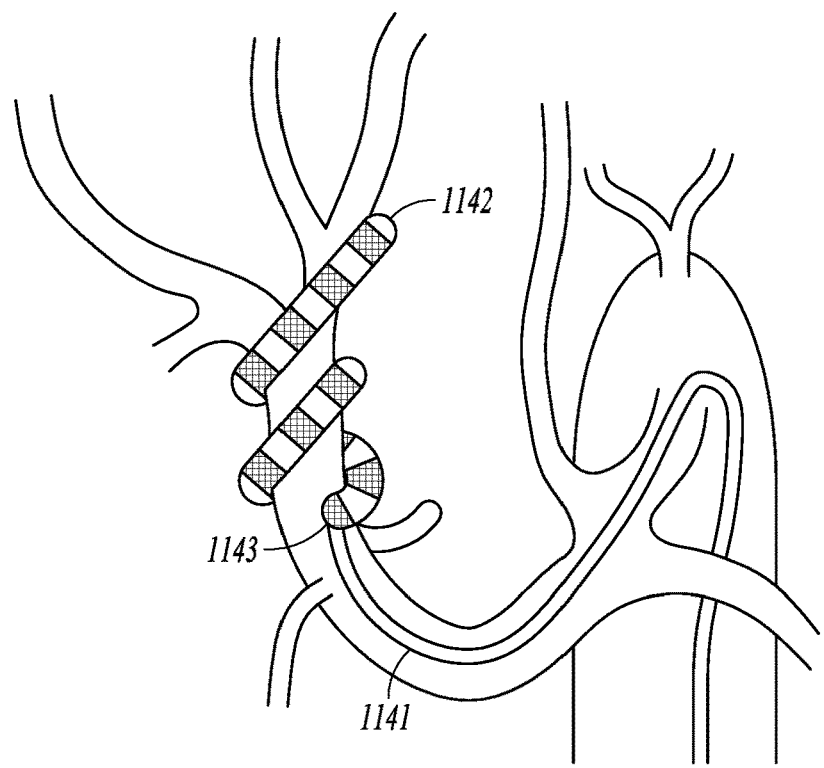
FIG. 11 illustrates, by way of example, an intravascularly-delivered lead with a distal portion that is configured to puncture through a wall of the vessel and extravascularly interface with hepatic neural targets.
Figure 12:
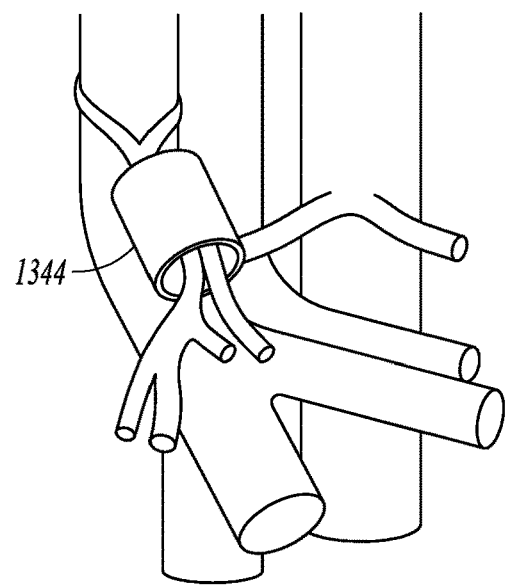
FIGS. 12 and 13 illustrate, by way of example, an implantable neuromodulator integrated with electrodes for implantation at a hepatic neural target.
Figure 13:
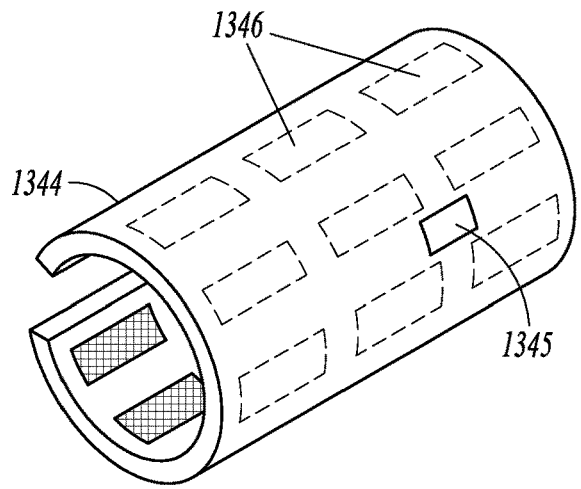

FIG. 11 illustrates, by way of example, an intravascularly-delivered lead 1141 with a distal portion 1142 that is configured to puncture through a wall of the vessel and extravascularly interface with hepatic neural targets. Thus, when exiting the guide catheter, the lead can be steered and advanced to exit the vascular at a puncture site 1143 and then at least partially surround the targeted neural tissue. FIGS. 12 and 13 illustrate, by way of example, a cuff 1344 that includes an implantable neuromodulator 1345 integrated with electrodes 1346 for implantation at a hepatic neural target. According to some embodiments, current delivered from each of the electrodes may be independently controlled.

Figure 14A:
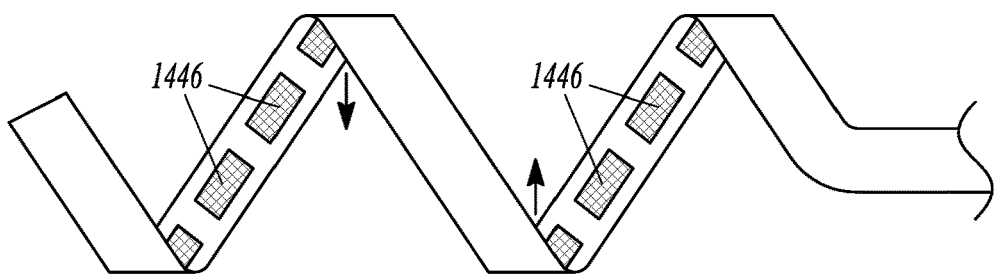
Figure 14B:
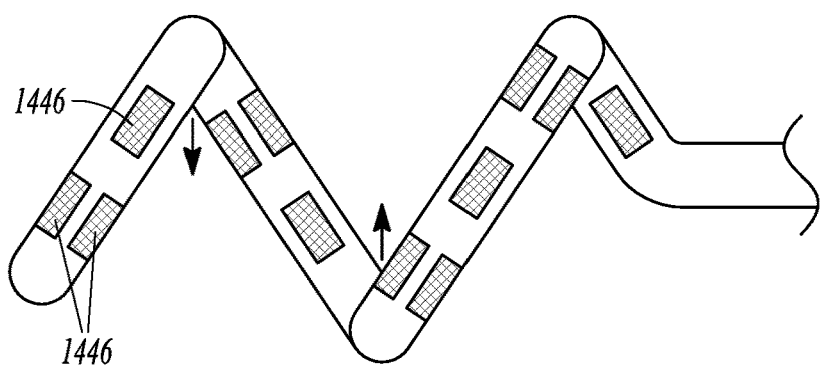

FIGS. 14A and 14B illustrate, by way of example, lead embodiments configured to wrap around blood vessels and/or nerves. FIG. 14A, for example, illustrates a coiled distal portion configured to be wrapped around nerve(s) and or vessel(s) with inwardly-facing electrodes 1446 (e.g. no outwardly-facing electrode) to focus electrical modulation energy toward the neural targets. FIG. 14B, for example, also illustrates a coiled distal portion configured to be wrapped around nerve(s) and or vessel(s), but have both inwardly and outwardly facing electrodes. Furthermore, the electrodes may be staggered. For example, a row of electrodes at one location along the lead may be at 0 and 180 degrees about a circumference of the lead, and the next row of electrodes along the lead may be at 90 and 270 degrees about the circumference. Thus, there are electrodes available for use to create a neuromodulation field shape to modulate targeted neural tissue. These distally-coiled electrodes may be configured with a shape memory to provide a slight compression around the nerve(s) and of vessels to maintain a good interface with the neural tissue but not damage the tissue. According to some embodiments, current delivered from each of the electrodes may be independently controlled.

Figure 15:
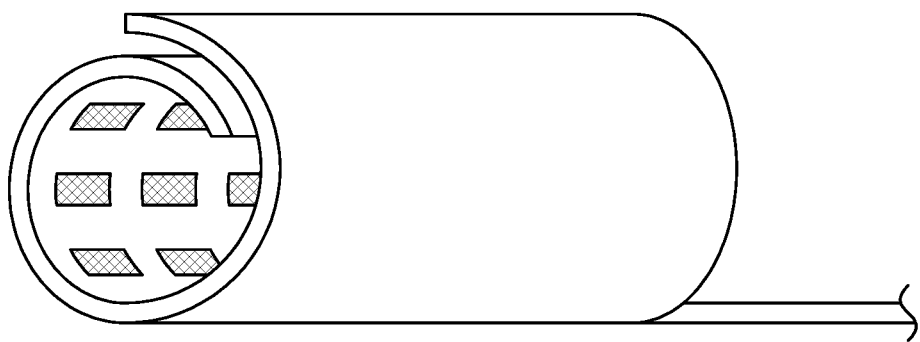
FIGS. 15-17 illustrate, by way of example, various lead embodiments with cuff(s) configured to wrap around blood vessels and/or nerves.
Figure 16:
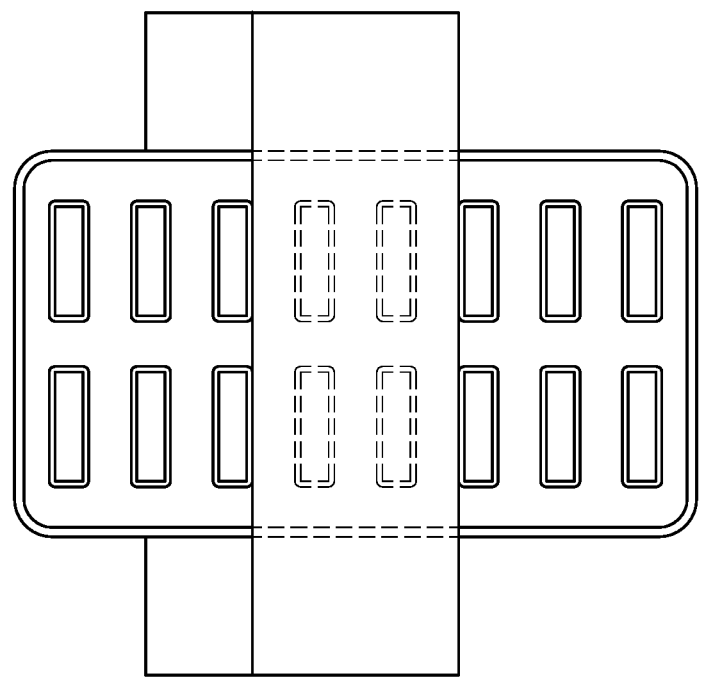
Figure 17:
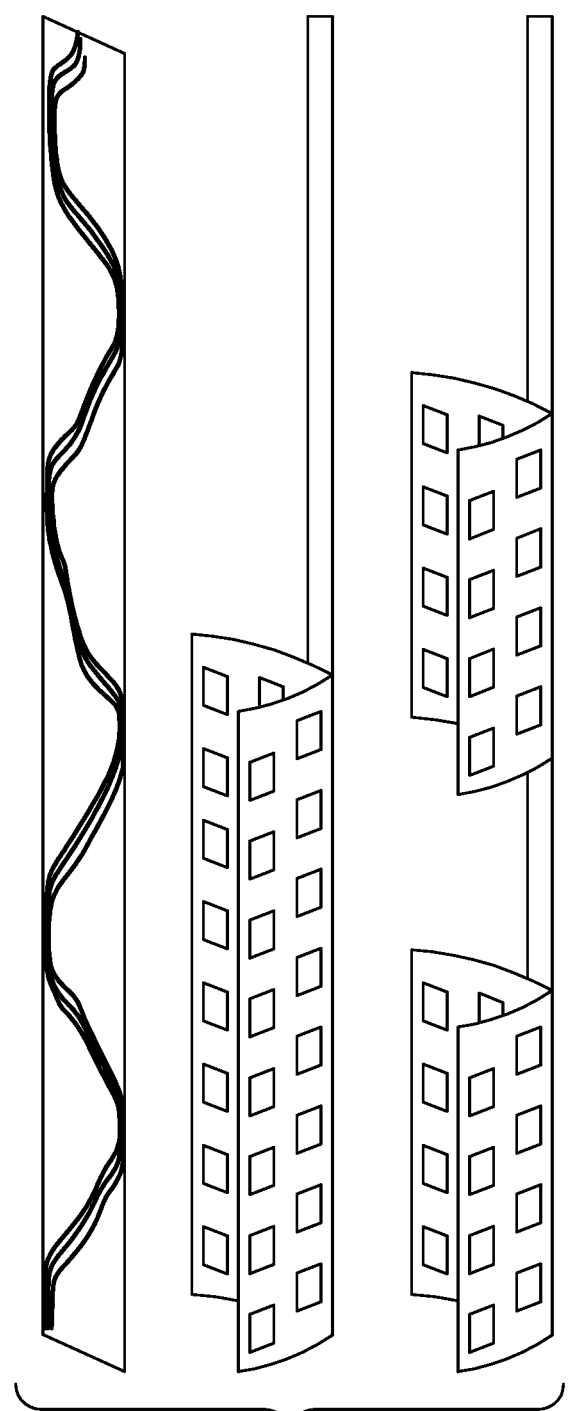

FIGS. 15-17 illustrate, by way of example, various lead embodiments with cuff(s) configured to wrap around blood vessels and/or nerves. These cuffs may include rows and columns of electrodes on one or more electrode patches. For example, some embodiments may include 8, 16 or 32 electrodes. According to some embodiments, current delivered from each of the electrodes may be independently controlled. FIG. 15 illustrates inwardly-facing electrodes integrated into the cuff. FIG. 16 illustrates a 16-electrode cuff design configured to be wrapped around a vessel. FIG. 17 illustrates cuff designs with one larger patch, or more than one patch such as may be used be used to wrap around targeted hepatic neural targets. For example, some embodiments may be configured to position one patch along the proper hepatic artery, and position another patch along the common hepatic artery similar to the positions illustrated in FIG. 4A.

As discussed above, various embodiments include multiple electrodes. Various embodiments are able to independently control the contributions of individual ones of the electrodes, such as using multiple independent current control (MICC).

Figure 18:
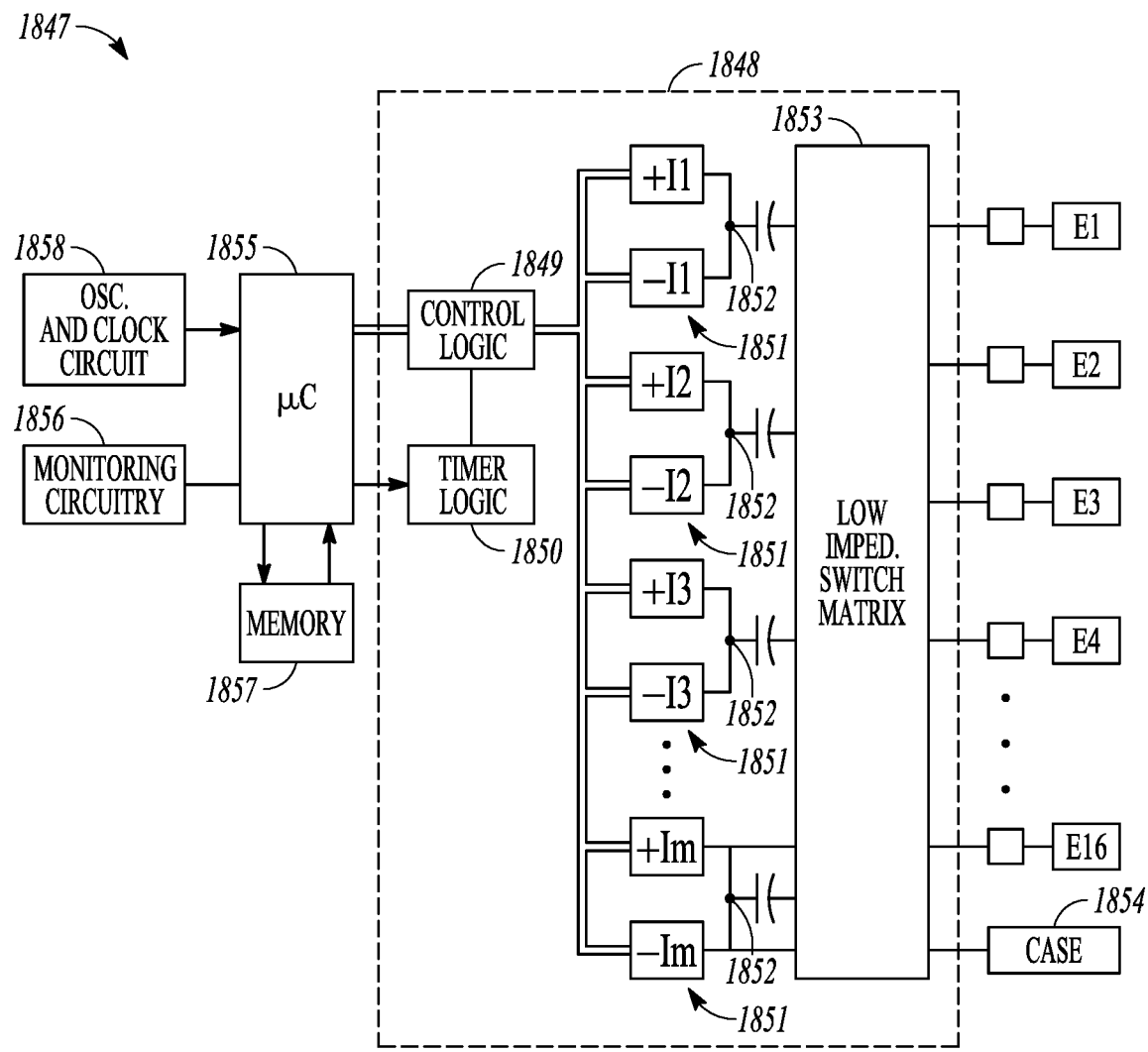
FIG. 18 illustrates, by way of example, an embodiment of a neuromodulator with multiple independent current generators.

FIG. 18 illustrates, by way of example, an embodiment of a neuromodulator with multiple independent current generators. The neuromodulator 1847 may include modulation output circuitry 1848 configured for generating electrical stimulation energy in accordance with a defined pulsed waveform having a specified pulse amplitude, pulse rate, pulse width, and pulse shape under control of control logic 1849 over a data bus. Control of the pulse rate and pulse width of the electrical waveform may be facilitated by timer logic circuitry 1850, which may have a suitable resolution, e.g., 10 µs. The modulation energy generated by the modulation output circuitry 1848 may be output to electrical terminals corresponding to electrodes E1-E16.

The output circuitry 1848 may include digital or analog circuitry, and may include one or more independently controlled electrical sources, which take the form of current sources and/or current sinks, for providing stimulation pulses of a specified and known amperage to or from the electrodes, or voltage sources and/or voltage sinks for providing stimulation pulses of a specified and known voltage at the electrodes. For example, the output circuitry 1848 may include a plurality of independent current source pairs 1851 capable of supplying stimulation energy to the electrical terminals at a specified and known amperage. One current source of each pair functions as a positive (+) or anodic current source, while the other current source of each pair functions as a negative (−) or cathodic current source. The positive current source may be referenced to as PDACs reflecting that the positive current source may be formed using a digital-to-analog converter (DAC) with P-type transistors (e.g. stages of P-type current mirrors) to source current, while the negative current source may be referenced as NDACs reflecting that the negative current source may be formed using a DAC with N-type transistors (e.g. stages of N-type current mirrors) to sink current. Those of ordinary skill in the art will understand DAC circuitry. DAC circuitry is configured to provide an output current based on an input current and input bits which may control the amplification provided to create the output current. The outputs of the anodic current source and the cathodic current source of each pair are connected to a common node 1852. In essence, each current source pair takes the form of a reconfigurable current source whose polarity can be switched. That is, by activating the anodic current source and deactivating the cathodic current source, the current source pair can be configured as an anodic current source, and by deactivating the anodic current source and activating the cathodic current source, the current source pair can be configured as a cathodic current source. Alternatively, instead of having s current source pairs, each of which includes an anodic current source and a cathodic current source, the reconfigurable current source can have a current source that can be switched between the positive terminal and the negative terminal of an energy source to selectively reconfigure the current source between an anodic current source and a cathodic current source. For example, the reconfigurable current source is coupled between an electrode and an energy source. Switches may be coupled between the respective positive and negative terminals of the energy source and the side of the current source opposite to the electrode.

The output circuitry may further include a low impedance switching matrix 1853 through which the common node of each current source pair is connected to any of the electrical terminals, and a capacitor coupled between the common node of each current source pair and the switching matrix. The switching matrix may be used to form source/electrode couplings (i.e., which active current sources and active electrode(s) are to be coupled together) that include more activated electrodes than activated current sources, thereby minimizing the number of current sources needed.

Thus, each of the programmable electrical terminals can be programmed to have a positive (sourcing current), a negative (sinking current), or off (no current) polarity. Further, the amplitude of the current pulse being sourced or sunk to or from a given electrode may be programmed to control output stage(s) of the DACs to provide any one of several discrete current levels, e.g., between 0 to 10 mA in steps of 100 μA, within the output voltage/current requirements of the neuromodulator. Also, the pulse width of the current pulses is preferably adjustable in convenient increments, e.g., from 0 to 1 milliseconds (ms) in increments of 10 microseconds (μs). Similarly, the pulse rate may be preferably adjustable within acceptable limits, e.g., from 0 to 1000 pulses per second (pps). Other programmable features can include slow start/end ramping, burst stimulation cycling (on for X time, off for Y time), interphase (i.e., the duration between first and second phases of biphasic energy), and open or closed loop sensing modes. Moreover, it is seen that each of the electrical terminals can operate in a multipolar mode, e.g., where two or more electrical terminals are grouped to source/sink current at the same time. Alternatively, each of the electrical terminals can operate in a monopolar mode. For example, the electrical terminals may be configured as cathodes (negative), and a case 1854 of the implantable neuromodulator may be configured as an anode (positive).

An electrical terminal may be assigned an amplitude and included with any of up to k possible groups, where k is an integer corresponding to the number of channels, and in one embodiment, is equal to 4, and with each channel k having a defined pulse amplitude, pulse width, pulse rate, and pulse shape. Other channels may be realized in a similar manner. Thus, each channel identifies which electrical terminals (and thus electrodes) are selected to synchronously source or sink current, the pulse amplitude at each of these electrical terminals, and the pulse width, pulse rate, and pulse shape. Amplitudes and polarities of electrodes on a channel may vary, e.g., as controlled by an external device. External programming software in the external device may typically be used to set modulation parameters including electrode polarity, amplitude, pulse rate and pulse width for the electrodes of a given channel, among other possible programmable features.

The illustrated neuromodulator 1847 further comprises processing circuitry in the form of a microcontroller (μC) 1855 that controls the control logic 1849 over data bus. In some embodiments, the microcontroller may receive status data from monitoring circuitry 1856. The neuromodulator may additionally control the timer logic 1850 and switching matrix 1853. The neuromodulator may further include memory 1857 and oscillator and clock circuitry 1858 coupled to the microcontroller. The microcontroller, in combination with the memory and oscillator and clock circuit, thus comprise a microprocessor system that carries out a program function in accordance with a suitable program stored in the memory. Alternatively, for some applications, the function provided by the microprocessor system may be carried out by a suitable state machine.

Thus, the microcontroller 1855 generates the necessary control and status signals, which allow the microcontroller 1855 to control the operation of the neuromodulator 1847 in accordance with a selected operating program and stimulation parameters. In controlling the operation of the neuromodulator 1847, the microcontroller 1855 is able to individually generate a train of stimulus pulses at the electrodes using the output circuitry 1848, in combination with the control logic 1849 and timer logic 1850, thereby activating selected ones of the electrodes, including the monopolar case electrode. In accordance with stimulation parameters stored within the memory, the microcontroller may control the polarity, amplitude, rate, pulse width and channel through which the current stimulus pulses are provided. The microcontroller also facilitates the storage of electrical parameter data (or other parameter data) measured by the monitoring circuitry within memory, and also provides any computational capability needed to analyze the raw electrical parameter data obtained from the monitoring circuitry and compute numerical values from such raw electrical parameter data.

The diagram for the illustrated neuromodulator is functional only, and is not intended to be limiting. Those of skill in the art, given the descriptions presented herein, should be able to readily fashion numerous types of neuromodulator circuits, or equivalent circuits, that carry out the functions indicated and described, which functions include not only producing a stimulus current or voltage on selected groups of electrodes, but also the ability to measure electrical parameter data at an activated or non-activated electrode.

Various embodiments of the present subject matter may use "target multipole(s)" to provide modulation field using the multi-electrode lead(s). These target multipole(s) may be referred to as "ideal" or "virtual" multipole(s). The target pole(s) can be estimated by controlling which of the electrodes are active, and which of the active electrodes are contributing toward the anodic current and which of the active electrodes are contributing toward the cathodic current. Each target pole of a target multipole may correspond to one physical electrode, but may also correspond to a space that does not correspond to one electrode, and may be emulated using electrode fractionalization. By way of examples, U.S. Pat. Nos. 8,412,345 and 8,909,350 describe target multipoles. U.S. Pat. Nos. 8,412,345 and 8,909,350 are hereby incorporated by reference in their entirety. Target multipoles are briefly described herein. A stimulation target in the form of a target poles (e.g., a target multipole such as a target bipole or target tripole or a target multipole with more than three target poles) may be defined and the stimulation parameters, including the fractionalized current values on each of the electrodes, may be computationally determined in a manner that emulates these target poles. Current steering may be implemented by moving the target poles about the leads, such that the appropriate fractionalized current values for the electrodes are computed for each of the various positions of the target pole.

Figure 19:
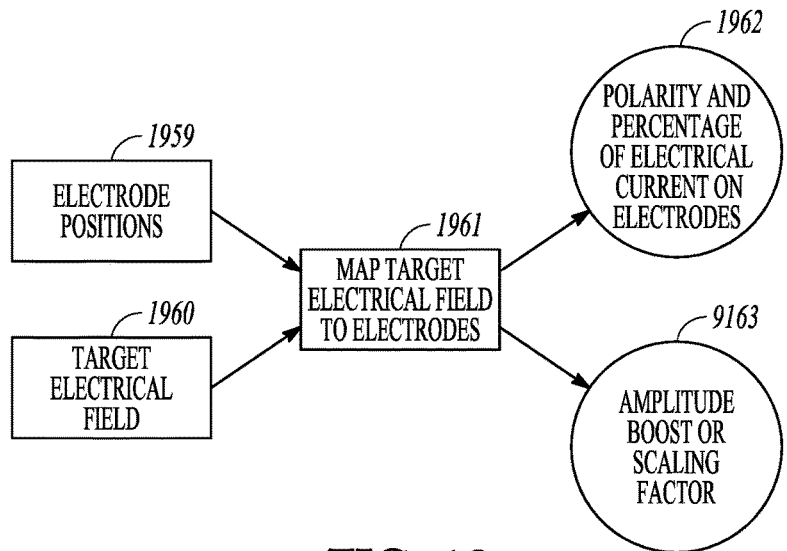
FIG. 19 illustrates, by way of example, a process that may be implemented to map a target field to electrodes being used to deliver the neuromodulation.

FIG. 19 illustrates, by way of example, a process that may be implemented to map a target field to electrodes being used to deliver the neuromodulation. The clinician programmer may be configured to accept relative electrode positions 1959 and a representation of an target electrical field 1960 and map the target electrical field to the electrodes 1961, thereby yielding the polarities and percentages of electrical current to be associated with the electrodes 1962, as well as a boost or scaling factor 1963 for globally adjusting the magnitude of the total current supplied to the electrodes to maintain a perceived intensity level of the electrical stimulation. Electrode locations and information about the desired electrical field may be independently inputted into the algorithm.

Figure 20:
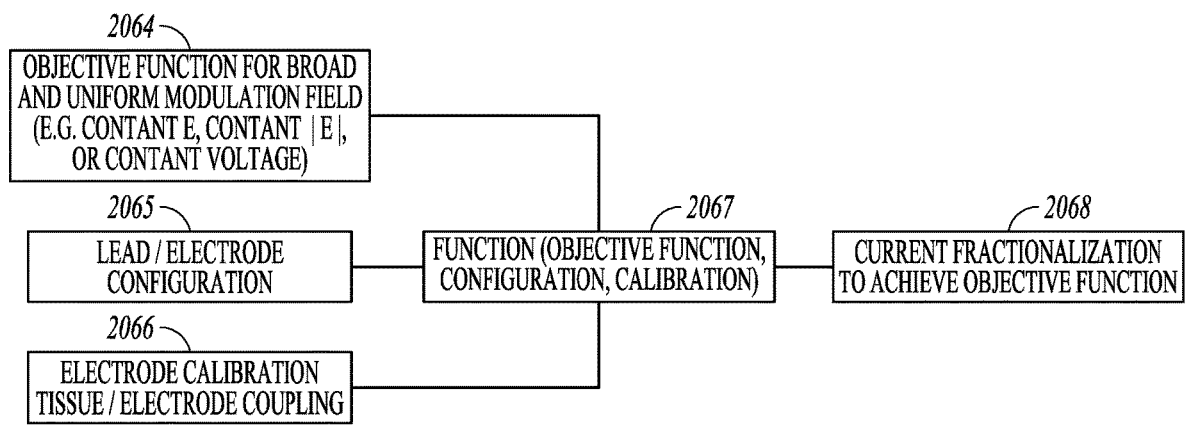
FIG. 20 illustrates, by way of example, an embodiment for determining fractionalization to achieve an objective function, where an objective function refers to a function with desirable characteristics for modulating the targeted tissue.

FIG. 20 illustrates, by way of example, an embodiment for determining fractionalization to achieve an objective function, where an objective function refers to a function with desirable characteristics for modulating the targeted tissue.

The objective function may also be referred to as an objective target function. For example, some embodiments may use objective function 2064 to provide a broad and uniform modulation field is identified for a given volume of tissue. Examples of an objective function includes a constant E (electric field), a constant |E| (electric field magnitude), and a constant voltage. The lead and electrode configuration 2065 are also identified, as well as calibration for electrode tissue coupling 2066. A function 2067 is performed that is dependent on the objective function, the lead and electrode configuration and the calibration. The result of the function is the fractionalization of modulation energy (e.g. current) 2068 for each electrode to achieve the objective function.

Some embodiments are configured to determine a modulation parameter set to create a field shape to provide a broad and uniform modulation field to enhance modulation of targeted neural tissue. Some embodiments are configured to determine a modulation parameter set to create a field shape to reduce or minimize modulation of non-targeted tissue. Various embodiments disclosed herein are directed to shaping the modulation field to enhance modulation of some neural structures and diminish modulation at other neural structures. The modulation field may be shaped by using MICC or multiple independent voltage control to guide the estimate of current fractionalization among multiple electrodes and estimate a total amplitude that provide a desired strength. For example, the modulation field may be shaped to enhance the modulation of targeted neural tissue (e.g. sympathetic and/or parasympathetic) and minimize modulation of non-targeted tissue. A benefit of MICC is that MICC accounts for variations in electrode-tissue coupling efficiency and perception threshold at each individual contact, so that "hot-spot" stimulation is eliminated.

Due to the linearity of field superposition, a transfer function can be formed to estimate the VDC(x,y,z) at selected direction induced by unit current from a single electrode located at (x0, y0, z0), the total V field is the linear combination of the V field induced by currents from each active electrode weighted by the current fractionalization.

Figure 21:
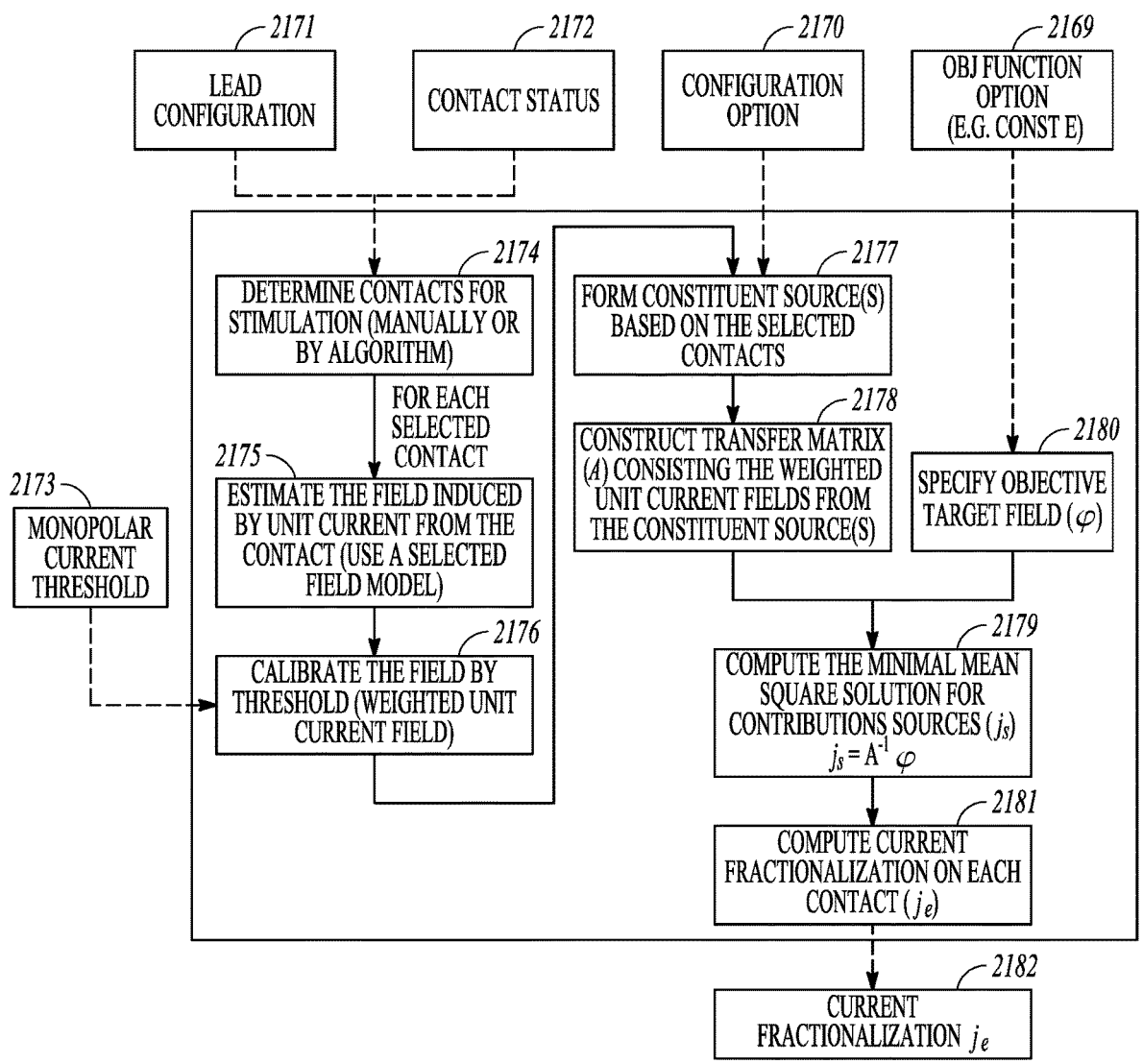
FIG. 21 illustrates, by way of example, an embodiment for determining fractionalization to achieve an objective function with more detail.

FIG. 21 illustrates, by way of example, an embodiment for determining fractionalization to achieve an objective function with more detail. An objective target function 2169 (e.g. constant E) is provided as an input to a process. Other inputs to the process include a configuration option 2170, a lead configuration 2171 and electrode contact status 2072, and a threshold 2073 such as a current threshold like a monopolar current threshold. The lead configuration 2171 and contact status 2072 identify an electrode arrangement, identifying a position of each electrode to determine the field. The overall field is a superimposed field from each electrode. The configuration option 2170 refers to monopolar (same polarity for all activated electrodes) and multipolar options (combined anode and cathodes in field). The threshold is used to compensate for electrode/tissue coupling differences.

The contacts for stimulation may be determined automatically or manually 2074 from the lead configuration and contact status. A selected field model may be used to estimate the field induced by unit current from the contact 2075. The field is calibrated using the threshold 2076. For example, the unit current field may be weighted. Constituent forces are formed based on the selected contacts 2077, and a transfer matrix 2078 is constructed to use to compute the minimal mean square solution 2079 using contributions from the constituent sources and using a specified target field 2080. The solution can be used to compute the current fractionalization on each contact 2082.

FIGS. 22A-22B illustrate a target electrical field mapped to the electrode array by estimating the field potential values (or some other linear electrical parameter, such as an activating function, current density, etc.) of the target field at a plurality of spatial observation points. The clinician programmer may map a target electrical field to the electrode array by estimating the field potential values (or some other linear electrical parameter, such as an activating function, current density, etc.) of the target field at a plurality of spatial observation points. The clinician programmer may accomplish this by determining the desired locations of target current source poles relative to the electrode array, and modeling an electrical field generated by the target current source poles to determine desired field potential values at the spatial observation points (e.g., using analytical and/or numerical models). The target pole(s) may be referred to as target multipoles, or as "ideal" or "virtual" pole(s).

FIGS. 23A-23C illustrate, by way of example, constituent current sources at the locations of the electrodes. Although target current source poles are one way to represent a "target electrical field", other representations of target fields may be used. The locations of the target current source poles may be determined in a manner that places the resulting electrical field over an identified region of the patient to be stimulated. The spatial observation points may be spaced in a manner that would, at the least, cover the entire tissue region to be stimulated and/or a tissue region that should not be stimulated. The locations of the target current source poles may be defined by the user, and may be displayed to the user along with the electrode locations, which as briefly discussed above, may be determined based on electrical measurements taken at the electrodes. The clinician programmer may select, or allow a user to select, a plurality of constituent current sources at the locations of the electrodes. The locations of the electrodes may be determined based on measurements taken at the electrodes in response to sub-threshold electrical signals transmitted between the electrodes. In the illustrated target bipole a first constituent current source can be defined at the locations of electrodes E1 and E2 as −100% and +100%, respectively (FIG. 23A), a second constituent current source can be defined at the locations of electrodes E2 and E3 as −100% and +100%, respectively (FIG. 23B); a third constituent current source can be defined at the locations of electrodes E3 and E4 as −100% and +100%, respectively (FIG. 23C); and so on. The location of each of the electrodes is included within at least one of the constituent sources. Thus, the minimum number of constituent sources may be equal to the number of contacts less one, or may equal the number of contacts (e. g., if a monopole is used as the constituent source).

Once the constituent sources are selected, the clinician programmer may determine the relative strengths of the constituent current sources that, when combined, result in estimated electrical field potential values at the spatial observation points that best matches the desired field potential values at the spatial observation points. In particular, the clinician programmer may model the constituent current sources (e.g., using analytical and/or numerical models) and estimate the field potential values per unit current (V/mA) generated by each of the constituent current sources at the spatial observation points, and may generate an m×n transfer matrix (shown in FIG. 24) from the estimated field potential values per unit current, with m equaling the number of spatial observation points and n equaling the number of constituent sources. The relative strengths of the constituent current sources may be determined using an optimization function that includes the transfer matrix A and the desired field potential values.

The optimization function may be a least-squares (over-determined) function expressed as: $|\varphi - A\hat{j}|^2$, where $\varphi$ is an m-element vector of the desired field potential values, A is the transfer matrix, and $\hat{j}$ is an n-element vector of the strengths of the constituent current sources. The constituent current source strengths $\hat{j}$ may be solved such that the optimization function $|\varphi - A\hat{j}|^2$ is minimized. The square difference is minimized if $\varphi = A\hat{j}$. One approach for solving this problem may be to invert the transfer matrix A and pre-multiply, such that $A^{-1} = \varphi A^{-1} A\hat{j}$, which yields the solution $\hat{j} = A^{-1}\varphi$. Once the strengths of the constituent current sources are determined, the clinician programmer may convert these strengths to current distributions on the electrodes in the form of a polarity and percentage.

Figure 25:
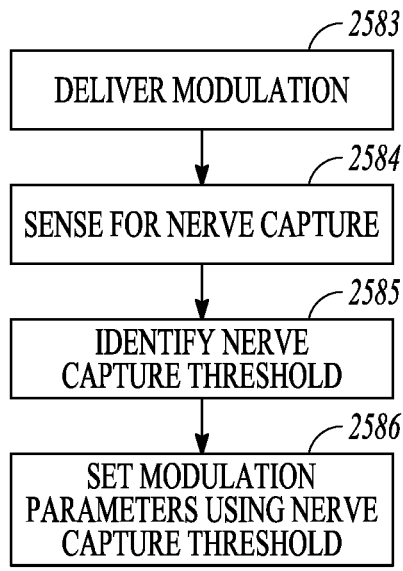
FIG. 25 illustrates, by way of example, a method for setting modulation parameters using an identified nerve capture threshold.

FIG. 25 illustrates, by way of example, a method for setting modulation parameters using an identified nerve capture threshold. It is noted that, as previously discussed with respect to FIG. 20 (e.g. 2073), the threshold may be use to calibrate each of the electrodes. Neuromodulation may be delivered through the electrode at 2583. The neuromodulation may be delivered using monopolar stimulation. At 2584, the process senses for nerve capture in response to the delivered neuromodulation. For example, an up-titration or down titration process may be used to gradually increase or decrease the delivered modulation until the threshold between no capture and capture is detected. At 2583, the modulation parameter(s) maybe set using the identified nerve capture threshold (see, by way of example, FIG. 21).

Figure 26:
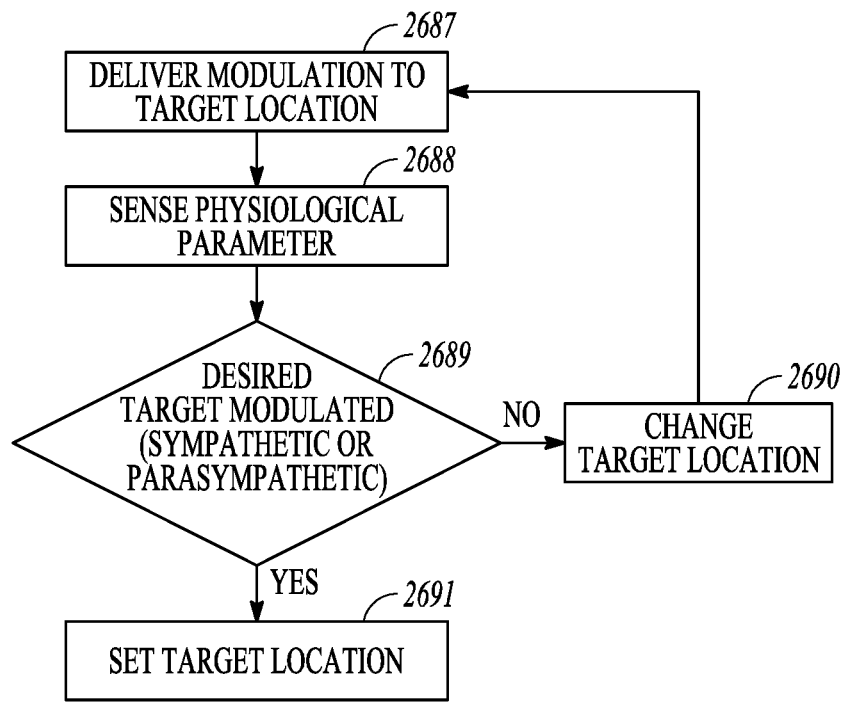
FIG. 26 illustrates, by way of example, a method for setting modulation parameters to modulate a target neuromodulation location.

FIG. 26 illustrates, by way of example, a method for setting modulation parameters to modulate a target neuromodulation location. At 2687, neuromodulation may be attempted to be delivered to a target location, and a physiological parameter may be sensed at 2688. More than one parameter may be sensed. The physiological parameter(s) may include a parameter that is expected to be affected when the target location is modulated. Additionally or alternatively, the physiological parameter(s) may include a parameter that is expected to be affected when a non-targeted location is modulated. At 2689, the sensed physiological parameter(s) are used to determine if the desired target (e.g. parasympathetic and/or sympathetic) has been modulated. If the desired target has not been modulated, the process changes where the neural tissue is stimulated, and returns to 2687 to again attempt to deliver neurostimulation to a targeted location. If the desired target has been modulated, the process may use that information to set the targeted location. Further refinements may be made. For example, the system may determine that different modulation parameter set(s) all are capable of being used to modulate the targeted location. The process may implement other feedback (e.g. patient or sensor feedback) to determine the efficacy of the modulation for a therapy, any side effects to the modulation, or energy use for the modulation. This information may be used to determine the desired modulation parameters to modulate the targeted location.

Figure 27:
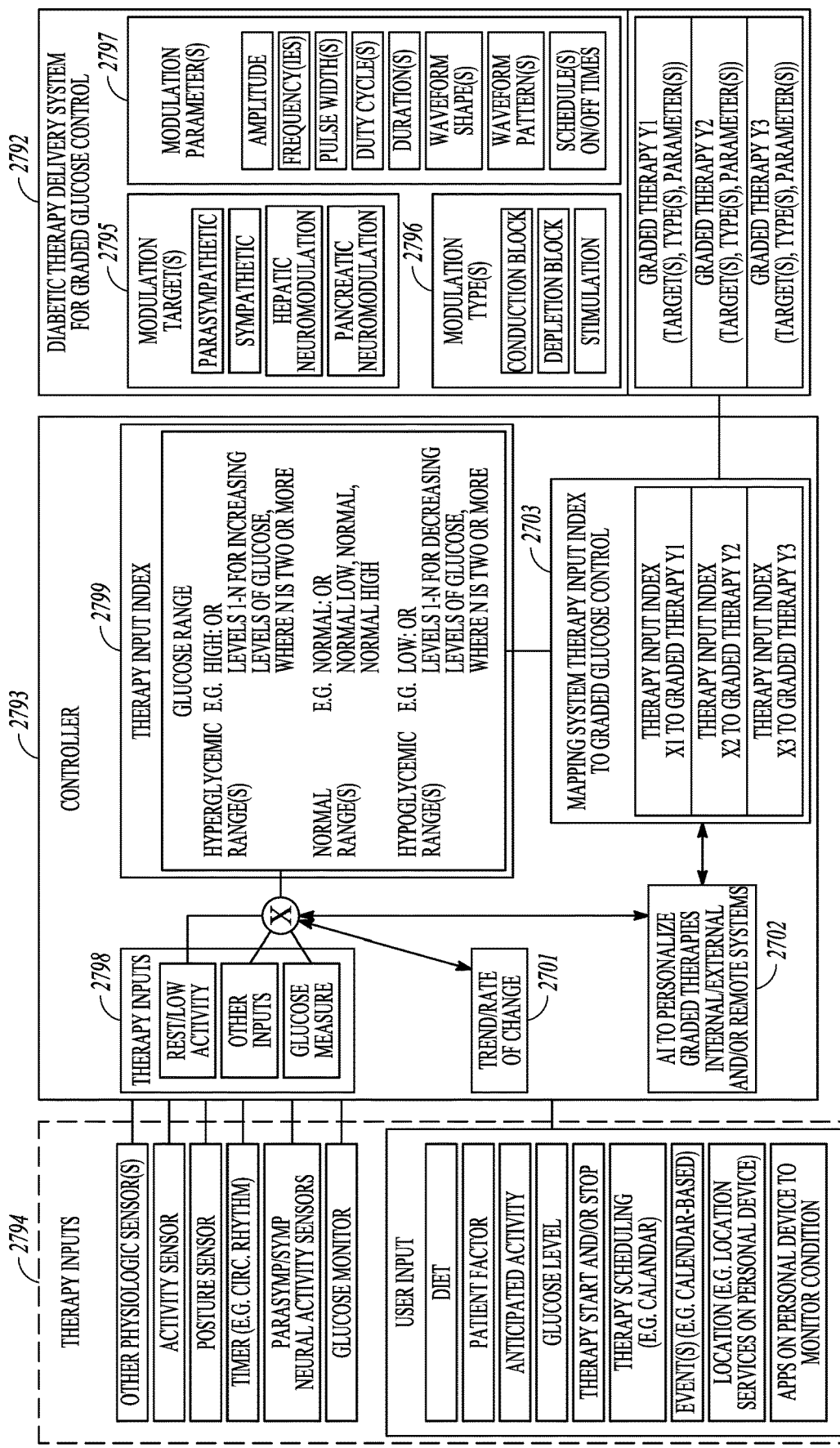
FIGS. 27-28 illustrate, by way of example, a system and process for delivering graded glucose control.
Figure 28:
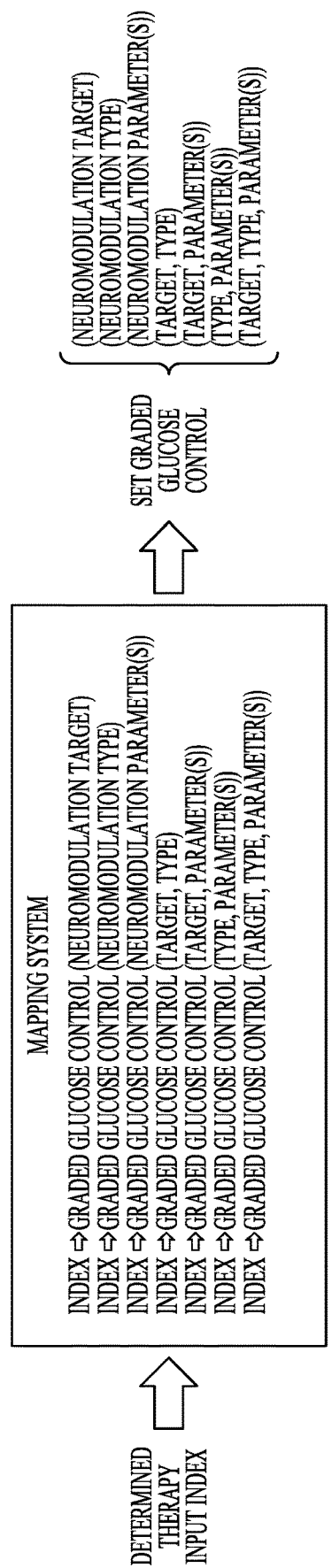

FIGS. 27-28 illustrate, by way of example, a system and process for delivering graded glucose control. It is expressly noted that various embodiments may include less than all of the features illustrated in this figures, various embodiments may include some of the illustrated features along with feature that are not illustrated, and various embodiments may include all of the illustrated features in addition to other features that are not illustrated.

The system illustrated in FIG. 27 includes a diabetic therapy delivery system 2792 for graded glucose control, a control system 2793 configured for controlling the diabetic therapy delivery system, and therapy inputs 2794 to the control system 2793 used by the control system 2793 to control the diabetic therapy delivery system 2792. In some embodiments, the diabetic therapy delivery system 2792 is configured to control the modulation target 2795 (e.g. whether the targeted neural tissue is a parasympathetic target and/or a sympathetic target and/or whether the modulation target is a hepatic neuromodulation target or a pancreatic neuromodulation target). In some embodiments, the diabetic therapy delivery system 2792 is configured to control the type of modulation 2796 that is delivered to the modulation target. For example, the type of modulation may be a conduction block, a depletion block, and/or a stimulation. These modulation types are described in more detail below. In some embodiments, the diabetic therapy delivery system 2792 is configured to control the modulation parameter(s) 2797 delivered to the modulation target. For example, the diabetic therapy delivery system 2792 may be configured to adjust one or more parameters selected from amplitude(s), frequency(ies), pulse width(s), duty cycle(s), schedule(s) (e.g. on/off times), duration(s), waveform shape(s), or waveform pattern(s). The therapy inputs 2794 may include a glucose monitor, a neural activity sensor (e.g. a sensor to detect neural activity on the parasympathetic or detect neural activity on the sympathetic nerves), a timer such as may be used to determine a time of day for a circadian rhythm, a posture sensor, an activity sensor, or another physiological sensor. Therapy inputs may include user inputs, such as diet, patient factor (e.g. patient specific parameters such as pregnancy status, lactation, comorbidities, use of other medications capable of altering glucose levels, dietary intake, time elapsed after eating, or other), anticipated activity, glucose levels, therapy start and/or stop, therapy scheduling (e.g. calendar-based scheduling), event (e.g. calendar-based events), location (e.g. location services on personal device, or apps on person device to monitor patient condition). Various embodiments may deliver a graded neuromodulation therapy by controlling a duty cycle of the modulation.

The controller is configured to receive therapy inputs at 2798 such as a glucose measure, an activity measure or other input(s) and generate a therapy input index 2799 using the received therapy inputs. Some embodiments may monitor a trend or rate of change 2701 of the therapy input(s) as an additional input for determining the therapy input index, 2799. Thus, for example, an instantaneous glucose measure may be analyzed with a trend of the glucose levels to determine a grade of therapy. For example, a moderately high glucose level that is trending downward may result in a lower grade of therapy than the same moderately high glucose level that is steady or trending upward. Some embodiments may use artificial intelligence (AI) to analyze the input(s) and the applied therapies to further personalize the graded therapies using internal systems, external systems, and/or remote systems. By way of example and not limitation, the AI may determine the rate of glucose change for certain types of foods and adjust the therapy accordingly. The therapy input index 2799 may determine the glucose range based on the input(s). For example, the controller 2793 may determine a therapy index for use to categorize whether the patient condition is in one or more hyperglycemic ranges, whether the patient condition is in one or more normal ranges, and whether the patient condition is in one or more hypoglycemic ranges. The multi-level ranges may be based on the instantaneous glucose measure with or without trending information. The level(s) may include levels that are at least partially based on the direction of the trend (e.g. increasing or decreasing glucose) and/or at least partially based on a rate of the change of the input(s) (e.g. change of glucose measures). The controller 2793 may include a mapping system 2703 configured to map various therapy indices to graded therapies. For example, a therapy input index X1 may be mapped to a graded therapy Y1, a therapy input index X2 may be mapped to a graded therapy Y2, and a therapy input index X3 may be mapped to a graded therapy Y3, etc. The diabetic therapy delivery system may be configured to provide the graded therapy, which was mapped from a therapy input index, by appropriately adjusting or selecting modulation target(s), modulation type(s) and/or parameter(s). FIG. 28 illustrates that a determined therapy index may be mapped to a therapy to a particular neural target, or a therapy using a particular neuromodulation type (e.g. stimulation, depletion block, conduction block), or to a particular modulation parameter set, or to combinations of two or more of the neural target, neuromodulation type and modulation parameter set.

Thus, for example, a therapy ON/therapy OFF ratio may be used for the graded therapy in this manner. A 25% duty cycle may correspond to 5 minutes during which the neuromodulation is ON and 15 minutes during which the neuromodulation is OFF. The duration of the ON times and OFF times may be controlled to provide a desired duty cycle. Various embodiments may deliver a graded neuromodulation therapy by controlling amplitude, frequency and pulse width of the neuromodulation therapy. For example, frequency may be adjusted to change among delivering stimulation, a partial depletion block, a full depletion block, or a full conduction block. Various embodiments may deliver a graded neuromodulation therapy using a combination therapy that includes both sympathetic modulation and parasympathetic modulation. For example, the parasympathetic and sympathetic nerves may be modulated either concurrently or intermittently. The graded therapy may include different combinations of blocking and/or stimulating the parasympathetic and/or sympathetic nerves.

Nerve fibers, also referred to as axons, are projections from nerve cells. A nerve fiber connects a nerve cell to another nerve cell or to muscle or to gland cells at synapses. Synapses are structures that permit nerve cells to pass an electrical or chemical signal to other cells. Nerve fibers includes A fibers, B fibers, and C fibers. A fibers are the largest and, generally, the first captured as stimulation amplitude increases. A fibers can be sensory fibers (afferent) or motor fibers (efferent) that innervate muscle tissue. B fibers are smaller and next to be captured when increasing current amplitude. These are typically efferent parasympathetic and sympathetic fibers. These B fibers may be a target for an autonomic neural stimulation therapy. C fibers are the smallest and associated with pain and other sensory information.

Thicker nerve fibers are generally activated before thinner nerve fibers. Thick nerve fibers have longer sections of myelin sheaths between the nodes of Ranvier where the depolarization occurs and thus the change in electric field they experience is greater. In general terms for a neural target that includes A, B and C fibers, the neural stimulation of the neural target may first capture A motor and large sensory nerves fibers, then small sensory and B parasympathetic nerve fibers. This order is a general order because fibers that are closer to the electrodes experience a stronger electric field and are activated before fibers that are further away, and further these fiber types overlap in their size. Then smaller B fibers (e.g. smaller myelinated fibers) and unmyelinated C fibers may be captured.

A neural block may be accomplished via frequencies greater than 100 Hz. For example, 100-900 Hz may be used for depletion block by activating the nerve continuously and depleting the neurotransmitter. Other frequency ranges may be used including but not limited to 100-1,000 Hz, 100-700 Hz, 100-500 Hz). The range may depend on the particular neural target and the neurotransmitter that is being depleted. Activation and block thresholds may be identified via neural recordings from an electrode. For example, current could be delivered between two electrodes that are proximal to a distal sensing electrode. The distal sensing electrode may measure intrinsic nerve activity or evoked action potentials, to quantify effectiveness of block or neural activation. Further, in the case of reversible nerve block, one or more electrodes may be positioned proximal to the electrodes used for reversible block, where those electrodes are used to evoke action potentials. Then, when reversible nerve block therapy is applied, if effective, the sensing electrode will be able to detect diminished evoked action potentials.

Block thresholds may be identified, where block threshold is identified as a minimum current or voltage required for full neural block. For partial block, for example, the amplitude at 100-900 Hz frequency could range from 10%-95% of that block threshold. Alternatively, an amplitude at 100% or greater of the block threshold could be used but delivered using a duty cycle of X minutes on and Y minutes off. For example, a therapy may be delivered using 5 minutes ON, 5 minutes OFF. The ON/OFT times may be adjusted to grade the therapy. The same applies to other modes of modulation with regard to using a duty cycle for graded therapy, such as kHz-frequency (e.g. 1 kHz to 50 kHz) or non-thermal pulsed radiofrequency block parameters such as 480 kHz, also already disclosed, or for low-frequency stimulation parameters intended to activate nerves (e.g. <50 Hz).

Yet a further mode of graded therapy is use of a combination of sympathetic and parasympathetic modulation, for example, concurrently down-regulate sympathetic activity and parasympathetic activity which are theorized to have partially counter-acting results (e.g. to achieve a smaller glucose-reducing effect than down-regulating sympathetic activity only). Likewise, for an additive effect, sympathetic activity can be down-regulated concurrently with parasympathetic activity being up-regulated for a larger glucose-reducing effect than down-regulating sympathetic activity alone.

For embodiments that combine neuromodulation of both sympathetic and parasympathetic targets, a weighting factor may be used for different electrical modulation frequencies. For example, ++ is equivalent to 2× increase.

TABLE 1

| Parameter Range | Glucose-Modulating Effect | | | |
|---|---|---|---|---|
| | Parasympathetic | | Sympathetic | |
| | Effect/Strength | Response Time | Effect/Strength | Response Time |
| Conduction Block (kHz) | Up-Regulate ++ | Slow | Down-Regulate ----- | Slow |
| Depletion Block (100-900 Hz) | Up-Regulate + | Slow | Down-Regulate --- | Slow |
| Stimulation (<50 Hz) | Down-Regulate - | Fast | Up-Regulate ++ | Fast |

It is currently believed that a stimulation effect (either parasympathetic or sympathetic) may be faster-acting than a blocking effect. A combination of parasympathetic and sympathetic modulation may be used as follows. To down-regulate glucose, particularly when glucose is significantly high (e.g. >170 mg/dL) and/or a fast response is desired (e.g. during acute hyperglycemia such as right after a meal, pregnancy, etc.), initiate parasympathetic modulation at a glucose Down-Regulating therapy setting (e.g. <50 Hz) before or concurrent with Sympathetic modulation at parameters sufficient to block neural activity (e.g. >100 Hz, glucose down-regulating therapy). In this example, the parasympathetic modulation will generate a fast response to begin the process of glucose reduction, and the Sympathetic modulation, while perhaps a slower response time, is expected to produce a stronger and more robust response. After glucose levels have begun trending down and are in a safer range (e.g. closer to 140 mg/dL), then parasympathetic modulation can be de-activated and Sympathetic modulation can continue. Other combinations thereof may be used with the % of parasympathetic and % of sympathetic modulation depending upon patient-specific responses, which can be characterized and learned over time, to better fine-tune and 'individualize' therapy. It should be noted that in some cases a fast response may not be needed, such as during exercise mode with moderate exercise, when the body is actively using the glucose.

The parasympathetic and/or sympathetic modulation parameters may be a function of not only activity level (sedentary, moderate exercise, high athletic activity, etc.), but also other patient parameters such as pregnancy status, lactation, comorbidities, use of other medications capable of altering glucose levels, dietary intake, time elapsed after eating (the longer it is, the more glucose is needed), or other patient-specific parameters. In Example 1 below, it is depicted that for a sympathetic modulation (e.g. hepatic modulation only) therapy, the duty cycle may be a function of a patient's response to therapy as well as their activity level. Because each patient will respond differently to therapy, the parameters (e.g. duty cycle) may vary from individual to individual. Dynamic weighting factors may be used to accommodate these variations. These dynamic weighting factors may be learned over time as patient's response to various therapies is measured, to continue to titrate and fine-tune therapy to the individual.

TABLE 2

| Glucose Level | Activity Level | Patient Factor | Freq, Pulse Width | Duty Cycle |
|---|---|---|---|---|
| <50 mg/dL | A | P | 10 Hz, 1000 us | f(A, P) × 100% |
| 50-100 mg/dL | A | P | 10 Hz, 1000 us | f(A, P) × 50% |
| 100-140 mg/dL | A | P | OFF | OFF |
| 140-170 mg/dL | A | P | 5 kHz, 70 us | f(A, P) × 70% |
| >170 mg/dL | A | P | 5 kHz, 70 us | f(A, P) × 100% |

Further, separate weighting factors may be applied to parasympathetic and sympathetic modulation therapies, as depicted in Table 2. The weighting factors for parasympathetic and sympathetic modulation may vary depending upon the glucose level (e.g. perhaps parasympathetic will have a more favorable weighting factor for up-regulating glucose than it will for down-regulating glucose in a particular patient, for example). In this example, Patient Factor P encompasses other factors that can affect a patient's response to therapy or need for therapy not included in the parasympathetic or sympathetic weight factors, such as those mentioned above.

TABLE 3

| Glucose Level | Activity Level | Patient Factor | Parasymp. Weight Factor* | Symp. Weight Factor* | Symp. Parameter (freq, PW) | Symp. Duty Cycle | Parasymp. Parameter (freq, PW) | Parasymp. Duty Cycle |
|---|---|---|---|---|---|---|---|---|
| <50 mg/dL | A | P | PW1 (0-2) | SW1 (1-5) | 10 Hz, 1000 us | f(SW1, A, P) × 100% | 5 kHz, 70 us | f(PW1, A, P) × 100% |
| 50-100 mg/dL | A | P | PW1 (0-2) | SW1 (1-5) | 10 Hz, 1000 us | f(SW1, A, P) × 50% | 5 kHz, 70 us | f(PW1, A, P) × 50% |
| 100-140 mg/dL | A | P | PW1 (0-2) | SW1 (1-5) | OFF | OFF | OFF | OFF |
| 140-170 mg/dL | A | P | PW2 (0-2) | SW2 (1-5) | 5 kHz, 70 us | f(SW2, A, P) × 70% | 10 Hz, 1000 us | f(PW2, A, P) × 70% |
| >170 mg/dL | A | P | PW2 (0-2) | SW2 (1-5) | 5 kHz, 70 us | f(SW2, A, P) × 100% | 10 Hz, 1000 us | f(PW2, A, P) × 100% |

*In parentheses is shown exemplary range for weighting factors

US Pat. Pub. No. 20150202446, published Jul. 23, 2015, filed by Franke et al. and entitled Selective Nerve Stimulation Using Presynaptic Terminal Depletion Block, provides a discussion regarding stimulation, depletion block and conduction block. As these may be implemented as different modulation types, certain teachings of US Pat. Pub. No. 20150202446 are incorporated below with respect to FIGS. 29-37M to describe depletion blocks. As the effect of nerves on muscles is relatively easy to visualize, the neuromuscular junction and the neurotransmitter acetylcholine (ACh) is used to illustrate the concept of depletion block. Also, an electromyography (EMG) monitor may be used to monitor muscular activity. Those of ordinary skill in the art will understand that the particular neurotransmitter will depend on the nerve (e.g. hepatic nerve) end organ (e.g. liver) that is being innervated.

Figure 29:
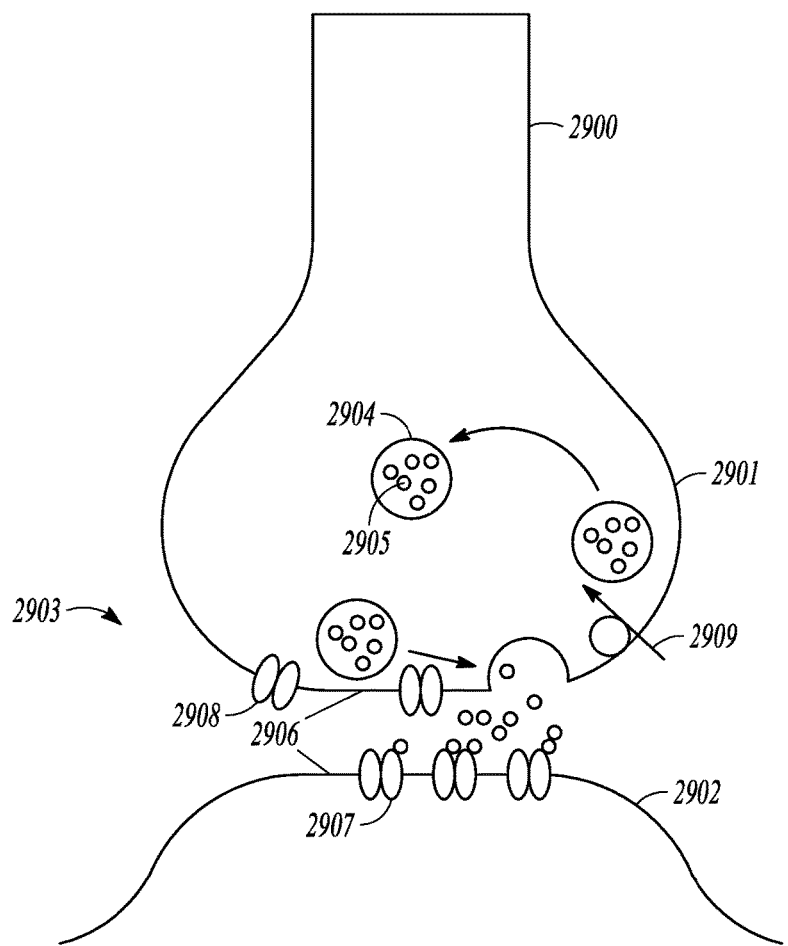
FIG. 29 illustrates neural activity at a synapse between a nerve and another membrane.

FIG. 29 illustrates neural activity at a synapse between a nerve and another membrane. An action potential propagates electrically down the nerve axon 2900 until it reaches a nerve ending, which may be referred to as a presynaptic terminal 2901. The presynaptic terminal communicates with a postsynaptic membrane 2902 of a target cell. The target cell may be another nerve or a muscle or gland. This membrane-to-membrane junction of the presynaptic terminal and the target cell is referred to as a synapse 2903. A type of synapse is an electrical synaptic junction where the presynaptic terminal electrically communicates with the postsynaptic membrane using ions or small molecules that pass through channels from one cell to the next. Another type of synapse is a chemical synaptic junction, where neurotransmitters are used to transmit between cells. The presynaptic area has a large number of synaptic vesicles 2904 that contain neurotransmitter chemicals 2905. Action potentials that propagate to the presynaptic terminal 2901 drive a chemical reaction in the presynaptic terminal that releases neurotransmitters from synaptic vesicles within the terminal into the extracellular space. This extracellular space may be referred to as a synaptic cleft 2906. The neurotransmitters cross the synaptic cleft between the presynaptic and postsynaptic terminals. The neurotransmitters start a chain of reaction in receptors 2907 of either the post-synaptic membrane 2902 (another neuronal cell) or the muscle cells (neuromuscular junction) that trigger either the firing of an action potential in the post-synaptic neuron or the muscular contraction if the synapse ends in a neuromuscular junction.

For example, where the target cell is a muscle and the synapse is a neuromuscular junction, ACh causes a rapid contraction of the target muscle cell. At a neuromuscular junction, the action potential travels to the neuromuscular synaptic junction, causing calcium ions to flow through voltage-gated calcium channels 2908 which release ACh from the presynaptic terminal into the extracellular space. Postsynaptic receptors in the membrane of the target muscle cell receive the ACh. The presynaptic terminal has a neurotransmitter re-uptake pump 2909 that replenishes the presynaptic terminal with synaptic vesicles of neurotransmitters.

Continual communication across this synaptic cleft 2906 appears to require a minimal amount of time between action potentials in the nerve, as post-synaptic receptors do not trigger action potentials if the pre-synaptic action potentials arrive close to each other. Higher stimulation frequencies will generate more stimulation pulses in a given period of time, and may generate more corresponding action potentials in the nerve during the period of time. For example, a neural stimulation signal may be within a range from about 0.25 Hz to 50 Hz, or may be within a range of about 2 Hz to about 20 Hz, or may be about 20 Hz. At higher frequencies (e.g. about 100 Hz to about 1 kHz), it may be observed that the presynaptic terminal was unable to communicate across the synaptic cleft even though action potentials continued to propagate through the axon. This inability of the presynaptic terminal to communicate may be referred to as a depletion block. The frequencies used to obtain this depletion block are lower than the high frequency (greater than 1 kHz) AC nerve block that would block action potentials from propagating down the nerve. At frequencies higher than 1 kHz, for example, the stimulation blocks the nerve from conducting the action potentials. In contrast, the depletion block is delivered at frequencies below 1 kHz and thus does not stop the action potentials from propagating down the nerve to the presynaptic terminal, but rather depletes the presynaptic terminal so it is no longer able to communicate across the synaptic cleft to receptors of another cell.

Figure 30:
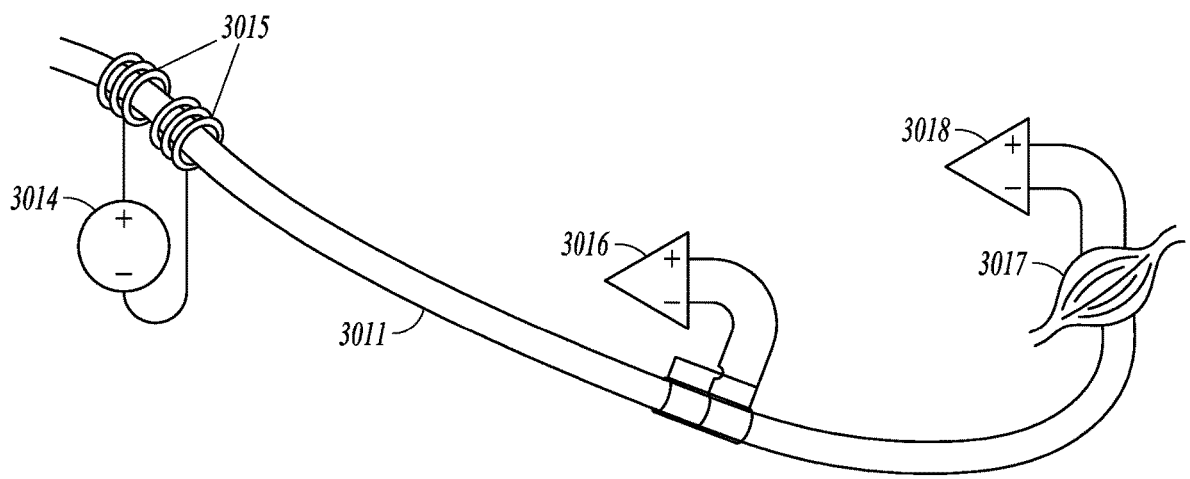
FIG. 30 illustrates a system that may be used to observe a presynaptic terminal depletion block delivered to a nerve.

FIG. 30 illustrates a system that may be used to observe a presynaptic terminal depletion block delivered to a nerve. Those or ordinary skill in the art will understand, upon reading and comprehending this disclosure, how depletion blocks may be delivered to neural targets that innervate the liver. The nerve 3011 may be stimulated using a current source 3014 and helical electrodes 3015 in a bipolar arrangement, to monitor neural using an electron urography (ENG) monitor 3016, and to monitor vibration of muscles 3017 using an electromyography (EMG) monitor 3018. Such a set-up may be used to observe that action potentials from depletion block stimulation were still sensed by the ENG, but muscle vibrations were not sensed by the EMG 3018. Thus, it could be concluded that the depletion block stimulation blocked the ability of the presynaptic terminal to communicate across the synaptic cleft.

Figure 31:
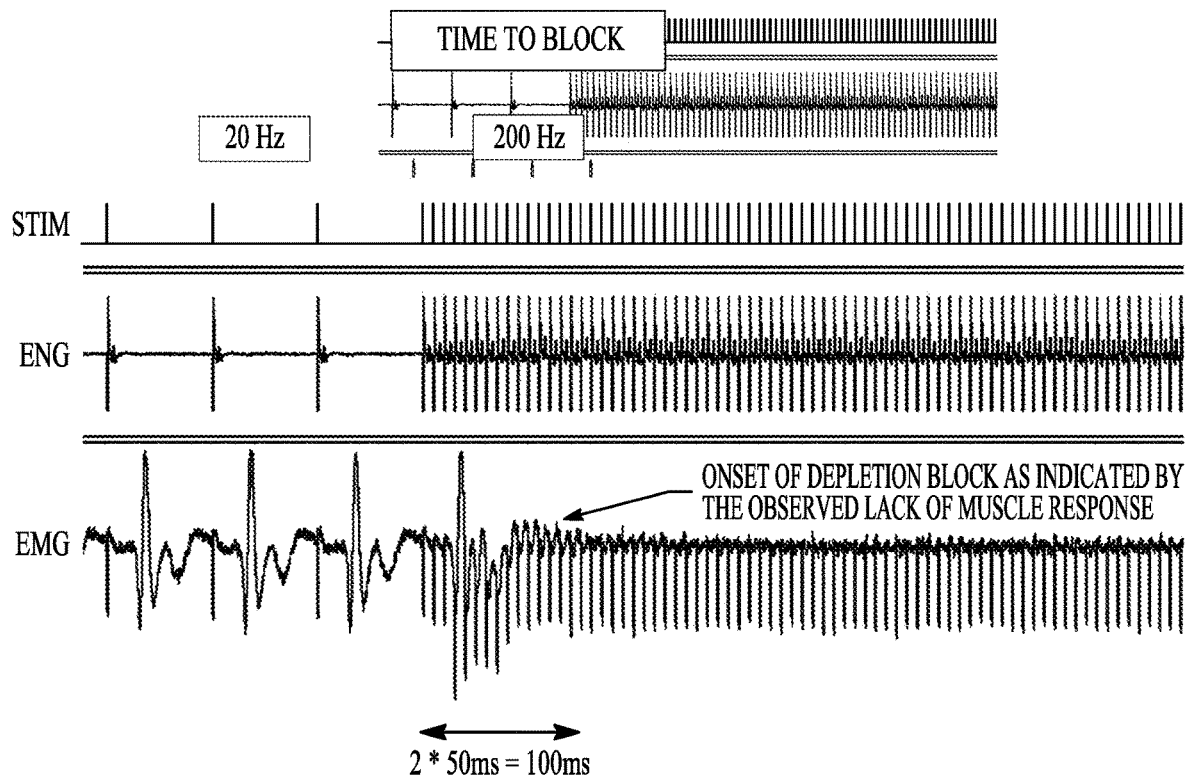
FIG. 31 illustrates the observed relationship between the stimulus signal and the recorded ENG and EMG signals when the stimulus changes from 20 Hz to 200 Hz, and also includes the observed time to deplete the presynaptic terminal and block the synaptic junction.

FIG. 31 illustrates the observed relationship between the stimulus signal and the recorded ENG and EMG signals when the stimulus changes from 20 Hz to 200 Hz, and also includes the observed time to deplete the presynaptic terminal and block the synaptic junction. During the 20 Hz stimulation, both the ENG and EMG signals follow the stimulus signal. The high peaks in both ENG and EMG signals reflect the stimulation artifact. However, during the 200 Hz stimulation, the ENG response is still present after the stimulus signal but the EMG signal quickly subsides after an onset response of about 100 ms. After a brief transitional period after the stimulus changes to 200 Hz, only the artifact from charge-balancing is seen in the EMG waveform. Thus, the axons in the nerve continue to be active by propagating action potentials, but the communication across the synaptic cleft is reduced or stopped after the presynaptic terminal has been depleted from its ability to communicate across the synaptic cleft. As illustrated, this synaptic junction block occurs very quickly (e.g. 50 to 100 ms after the 200 Hz signal is applied), as soon as the propagated pulses received at the presynaptic terminal deplete the presynaptic terminal from its ability to communicate. It does not appear that the physiological reuptake process that restores neurotransmitters and/or calcium in the presynaptic terminal can keep up with the transmission of the neurotransmitters from the 200 Hz stimulation.

Figure 32:
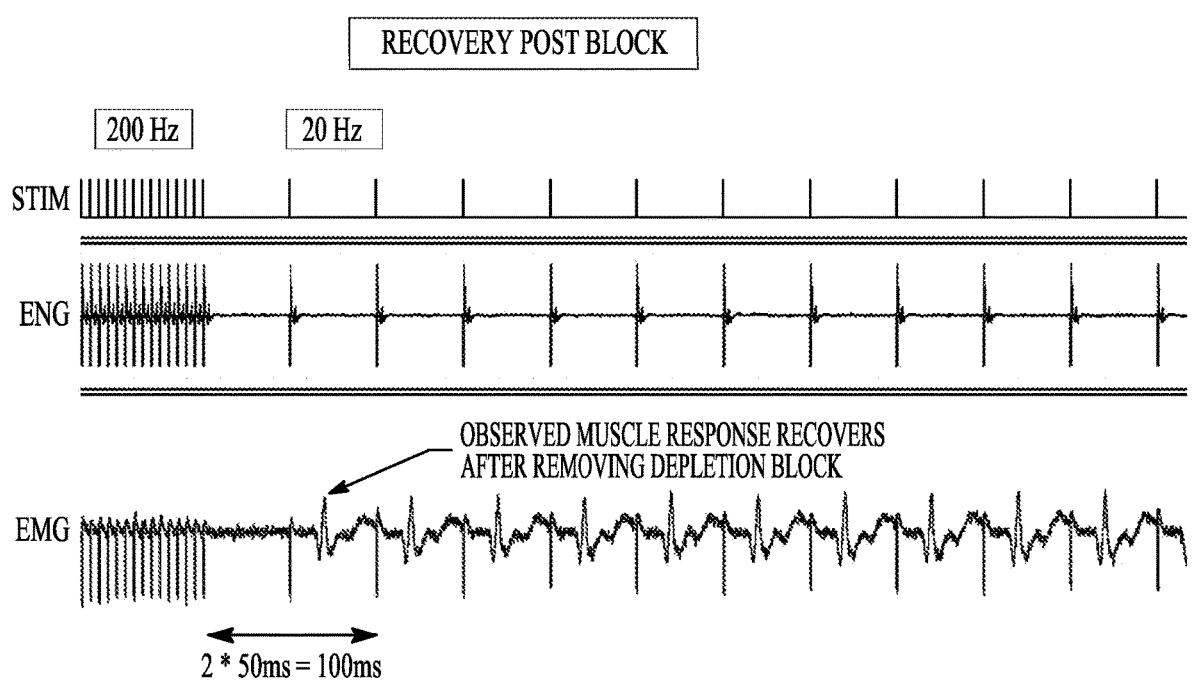
FIG. 32 illustrates the relationship between the stimulus signal and the recorded ENG and EMG signals when the stimulus changes from 200 Hz to 20 Hz.

FIG. 32 illustrates the relationship between the stimulus signal and the recorded ENG and EMG signals when the stimulus changes from 200 Hz to 20 Hz. The synaptic junction block occurs when the stimulus is delivered at 200 Hz. During this time, the ENG is still present following the stimulus artifact signal, but the EMG response is not present. This indicates that the stimulus is capturing the nerve and causing action potentials to propagate through the axon. Every pulse in the stimulation causes a respective action potential in the nerve fiber. However, the laryngeal muscle is not stimulated because of the presynaptic terminal depletion that causes the synaptic junction block. The 200 action potentials per second deplete the ability of the presynaptic terminal to communicate across the synaptic cleft. When the stimulus changes from 200 Hz to 20 Hz, however, the ENG response continues to be present following the stimulus pulse as every pulse in the stimulation causes a respective action potential in the nerve fiber. The EMG reappears right after the stimulus pulse just after a brief transitional period after the stimulation frequency changes to 20 Hz. The ability of the presynaptic terminal to communicate across the synaptic cleft is not depleted by 20 pulses per second. Thus, as illustrated, the synaptic junction block can be removed very quickly (e.g. 50 ms to 100 ms after the signal changes from 200 Hz to 20 Hz signal), which is believed to reflect the physiological response time for restoring neurotransmitters and/or calcium in the presynaptic terminal.

As illustrated in Table 4, Franke et al. indicated that certain frequencies turn the depletion block of the synaptic junction on/off more quickly than other frequencies, indicating that data suggest that frequencies greater than about 200 Hz provide a fast depletion block, whereas frequencies between about 100 to about 150 Hz provides slower depletion blocks. Frequencies below 100 Hz tend not be effective to provide the depletion block, as those frequencies do not exceed the ability of the presynaptic terminal to restore its ability to communicate from the presynaptic terminal across the synaptic cleft to the target cell. In a neural muscular junction, for example, frequencies less than about 100 Hz cause tetanic contraction; frequencies between about 100 to about 150 Hz causes a 90% depletion block in about 10 seconds to 4 seconds; a frequency between about 200 Hz to 1000 Hz causes a 90% depletion block; and a frequency is greater than 1 kHz starts to enter into nerve conduction block where the stimulation arrests the actions potentials from propagating down the nerve.

TABLE 4

| | Freq (Hz) | Time to 90% Block (sec) | | Percentage of unblocked EMG (%) | |
|---|---|---|---|---|---|
| | | mean | stdev | mean | stdev |
| Activation | 40[1] | — | — | 110 | 13.18 |
| | 70[1] | — | — | 39 | 8.42 |
| Slow Block | 100*,[2] | 10.74 | 2.2 | 8.2 | 3.77 |
| | 130[1] | 9.33 | 0.55 | 4.38 | 1.06 |
| | 150[2] | 4.43 | 2.59 | 3.88 | 1.13 |
| Fast Block | 200[2] | 0.53 | 0.16 | 2.25 | 1.04 |
| | 260[1] | 0.16 | 0.05 | 0.75 | 0.89 |
| | 300[2] | 0.13 | 0.05 | 1.13 | 1.13 |
| | 400[1] | 0.14 | 0.05 | 0.63 | 0.74 |

Randomized study; n = 8 (100 Hz: n = 5), data from 2 * N = 1
See Franke et al. (U.S. Pat. Pub. No. 20150202446).

Figure 33:
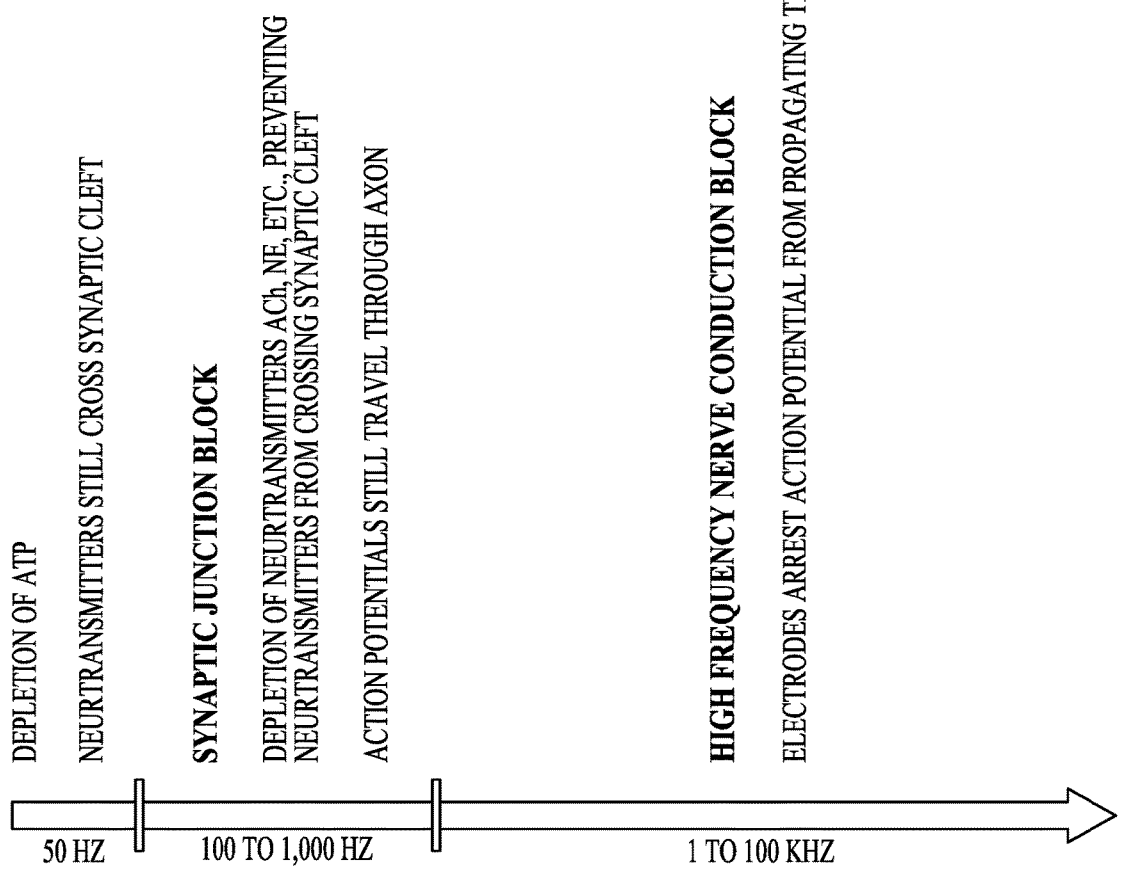
FIG. 33 illustrates the response of a neural muscular junction to different stimulation frequencies.

FIG. 33 illustrates the response of a neural muscular junction to different stimulation frequencies. Eventually, the muscle may fatigue and no longer respond to additional stimulation. The presynaptic terminal is depleted from its ability to communicate across the synaptic cleft at stimulation frequencies within a range from about 100 Hz to about 1 kHz. This frequency of the stimulation signal is outside of the ability of the physiological system to trigger the muscular contraction, as the frequency may cause the action potentials to arrive faster than the neurotransmitters and/or calcium can be replenished for subsequent action potentials in the stimulation. The observed block is attributable to a depletion of the junction but not fatigue of the muscle. Thus, a benefit of the depletion block applied to neural muscular junctions is that the depletion block does not cause muscle fatigue or tetanic contraction. The neuromuscular depletion block is quickly reversible by stopping stimulation.

FIG. 33 is a simple illustration of frequency ranges, and that these ranges may vary for different applications. For example, a kHz conduction block may be observed with a lower boundary of about 1 kHz to 5 kHz rather than the simply illustrated 1 kHz. Additionally, the upper boundary of a depletion block may be about 2 kHz rather than the simply illustrated 1 kHz. Further, the frequencies for which stimulation transitions from depletion to conduction depends on the nerve fibers and end organ. Therefore, although the frequency ranges that define the conduction, depletion block and conduction block for nerves that innervate the liver are expected to have some similarities into the nerves that innervate muscle, some differences are expected because of the differences in the fiber and end organ. Fast A-fibers have higher conduction and firing rates, so they will not necessarily block at 1 kHz, and slower fibers will block at lower frequencies (e.g. 600 Hz). Thus, there may be a nerve stimulation frequency band within which most fibers can be activated, a depletion block frequency band for which most fibers may be depleted, and a kHz conduction block frequency band for which most fibers have their action potentials blocked. By way of example and not limitation, the nerve stimulation frequency band may extend up to about 50 Hz, the depletion block frequency band may extend between about 100 Hz to about 700 Hz, and the kHz conduction block frequency band may extend from about 5 kHz to 100 kHz. There may be transition frequencies between the bands, such as a transition between about 50 Hz to about 100 Hz or between about 70 Hz to 130 Hz for example and another transition between about 700 Hz to about 5 kHz. The response of the nerve to the stimulation frequency appears to depend on the transmitter and the synaptic end organ. Thus, different types of fibers may react differently for frequencies within the transition frequencies. By way of example, one frequency may cause an activation or neural stimulation of some fibers, and cause a depletion block in other fibers. The stimulation may be limited to specific fibers by the diameter or origin of the fibers or the location of the electrodes. For example, a frequency of the depletion block stimulation may be found to discriminate between afferent and efferent nerve fibers, or to discriminate between different fibers that emit different types of neurotransmitters. Such a frequency capable of providing both depletion block and activation/stimulation may be found in a transition region, but also may be found in one of the frequency bands such as within the depletion block frequency band.

As illustrated in Table 4, the speed of the depletion block depends on the frequency of the stimulation, where higher frequencies within the range of about 100 Hz to about 1 kHz provide the neurotransmitter block more quickly than the lower frequencies within that range. According to some embodiments, the depletion block may be implemented by a process that initiates the depletion block at a relatively high frequency (e.g. about 200 Hz to 400 Hz) to achieve fast depletion (e.g. about 50 ms or less), and then subsequently lower the frequency of the depletion block stimulation to about 100 Hz to maintain the block. As the lower frequency stimulation delivers fewer pulses, the lower frequency depletion block is more energy efficient than the higher frequency depletion block. If the depletion block was started at about 100 Hz rather than 200 Hz, it would take longer to achieve the depletion block. Based on current observations, it is believed that the depletion block at 100 Hz will take about 5 seconds to 10 seconds. The use of two (or more) stages of frequencies can be used to obtain benefits of each frequency, such as inducing depletion block relatively quickly using one frequency and then maintaining depletion block relatively efficiently using another frequency.

Various embodiments may use a depletion block at the synaptic junction to provide selective fiber communication. A depletion block may be limited to specific fibers by diameter or origin or location to the electrode. The amplitude of the depletion block pulses can be controlled to be greater than only the stimulation threshold for only some of the nerve fibers. Thus, although all fibers may be captured with pulses that cause action potentials to propagate, the presynaptic terminal for some of the fibers are quickly depleted from their ability to communicate across the synaptic junction because the frequency of the stimulation causes the depletion block. Various stimulation waveforms may be used including non-sinusoidal or sinusoidal waveforms. Non-sinusoidal waveforms may include rectilinear pulses, charge balanced waveforms that may include biphasic rectangular pulses, quasi-trapezoidal for unidirectional applications, and pulsed triangular. Further, more complex, non-regular waveform shapes and/or non-regular waveform patterns, such as different pulse train patterns, may be used.

Neural stimulation that elicits nerve traffic and a desired physiological response as part of neural stimulation therapy may be referred to as a low frequency stimulation (e.g. about 20 Hz or within a range of about 0.25 Hz to about 50 Hz); whereas in comparison a depletion frequency may be referred to as high frequency (e.g. about 200 Hz or within a range of about 100 Hz to about 1 kHz). The stimulation at these lower frequencies that is effective in activating nerve fiber(s) to deliver a nerve stimulation therapy may be referred to herein simply as "nerve stimulation" or "neural stimulation;" whereas the stimulation at the higher "depletion" frequencies may be referred to herein simply as a "depletion block stimulation." A "high amplitude, low frequency" (HALF) stimulation signal may exceed a stimulation threshold and thus may be used to recruit both small and big fibers. As such, a HALF signal may be used to obtain the desired effect of the stimulation by capturing all the necessary A sensory and B efferent fibers. A "small amplitude, high frequency" (SAHF) stimulation signal may be set at an amplitude that it only exceeds a smaller stimulation threshold and thus only recruits some of the fibers with the lower stimulation threshold (e.g. bigger fibers or fibers closer to the stimulation electrode(s)), while leaving other fibers with a higher stimulation threshold (e.g. smaller fibers or fibers further away from the stimulation electrode(s)) still excitable with the HALF stimulation. The depletion block stimulation cancels the effectiveness of all signals that are evoked at lower frequencies (e.g. 20 Hz) with the same or lower amplitude. SAHF may be used to achieve the neurotransmitter depletion block of the large fibers which are the fibers with relatively low stimulation thresholds but not the smaller fibers which are the fibers with relatively high stimulation thresholds. In some embodiments, the higher frequency depletion block stimulation may be delivered using the same or approximately the same high amplitude as the low frequency stimulation to reduce or modulate the effect of the applied therapy using the low frequency stimulation.

The current amplitude and the pulse width control whether an axon is depolarized, and the frequency of the stimulation controls whether the neurotransmitters are depleted at the nerve ending. The current amplitude and pulse width may be controlled to select only larger fibers for the depletion block. For example, the current amplitude and pulse width may be controlled to deplete the A fibers and not the smaller fibers, or may be controlled with higher amplitudes and/or wider pulse widths to deplete both A and B fibers.

By way of example and not limitation, a full neurotransmitter block for intended fibers may be ensured by acquiring a recruitment curve. The recruitment curve may identify the activation threshold and saturation threshold for the neural target. The recruitment curve may be specific to an individual patient, may illustrate an increase in activity with increasing current amplitude, and may then illustrate a plateau where the activity does not significantly increase with increasing current amplitude. The activation threshold reflects where the nerve activity begins to increase with increasing current amplitude, and the saturation threshold reflects where the nerve activity does not significantly increase in response to further increases in current amplitude. The current amplitude for the depletion block stimulation may be determined based on the activation threshold, as it may be set at a margin higher than the activation threshold. The saturation threshold indicates a threshold where all or almost all of the nerve fibers propagate action potentials. The current amplitude for the depletion block stimulation may be higher than and based on the saturation threshold of the fibers that are intended to be blocked. By way of example, the amplitude of the depletion stimulation signal may be set at approximately the saturation threshold of the fibers that are intended to be blocked, or may be set at a margin higher than the saturation threshold of the fibers, or may be set at a margin lower than the saturation threshold to provide a partial block.

A procedure can be implemented to determine each individual patient's selective fiber stimulation therapy profile, as there may be patient variation or variations resulting from electrode spacing from nerves fibers. The particular procedure will depend on the particular neural target that is stimulated, as the nerve fibers in different neural targets innervate different portions of the body. Various embodiments for providing a depletion block may first find an activation threshold and saturation threshold for a neural target. The current amplitude may be selected to be above the saturation threshold of the neural target, and the frequency may be selected for a given application to be high enough (e.g. 200 Hz) to quickly deplete the presynaptic terminal of its ability to communicate across the synaptic cleft to provide an effective depletion block for that application. The procedure may transition the frequency of the stimulation while monitoring the physiological effects to transition between different types of block (e.g. transition between depletion block and kHz conduction block), or to improve efficiency, or to improve time constants (e.g. onset/ restoration), or to find a desired frequency and location that both activates some nerve fibers and also provides a depletion block for other nerve fibers.

Some embodiments may ramp up stimulation. Ramping up the stimulation may provide a graded block that may make the stimulation more tolerable. In a neural muscular junction depletion block, for example, the ramped stimulation may reduce the force of the one initial muscle activity at start of stimulation by creating an initial period of graded block. Some embodiments may change the frequency of stimulation signal during the block. Thus, higher frequency stimulations may be used to quickly obtain the block, and then lower frequency stimulation may be used to maintain the block that was previously obtained. For example, an initial frequency (e.g. 260 Hz) may be used to quickly achieve depletion block followed by a second frequency (e.g. 130 Hz) to maintain the depletion block. The frequency of stimulation is related to how long for complete or 90% depletion block. For example, frequencies within the range of about 100 to about 150 Hz provide a 90% depletion block in about 10 to 4 seconds, and frequencies within the range of about 200 to 1000 Hz provides a 90% depletion block less than one second (e.g. on the order of milliseconds). Frequencies greater than 1 kHz start to enter into nerve conduction block.

Figure 34:
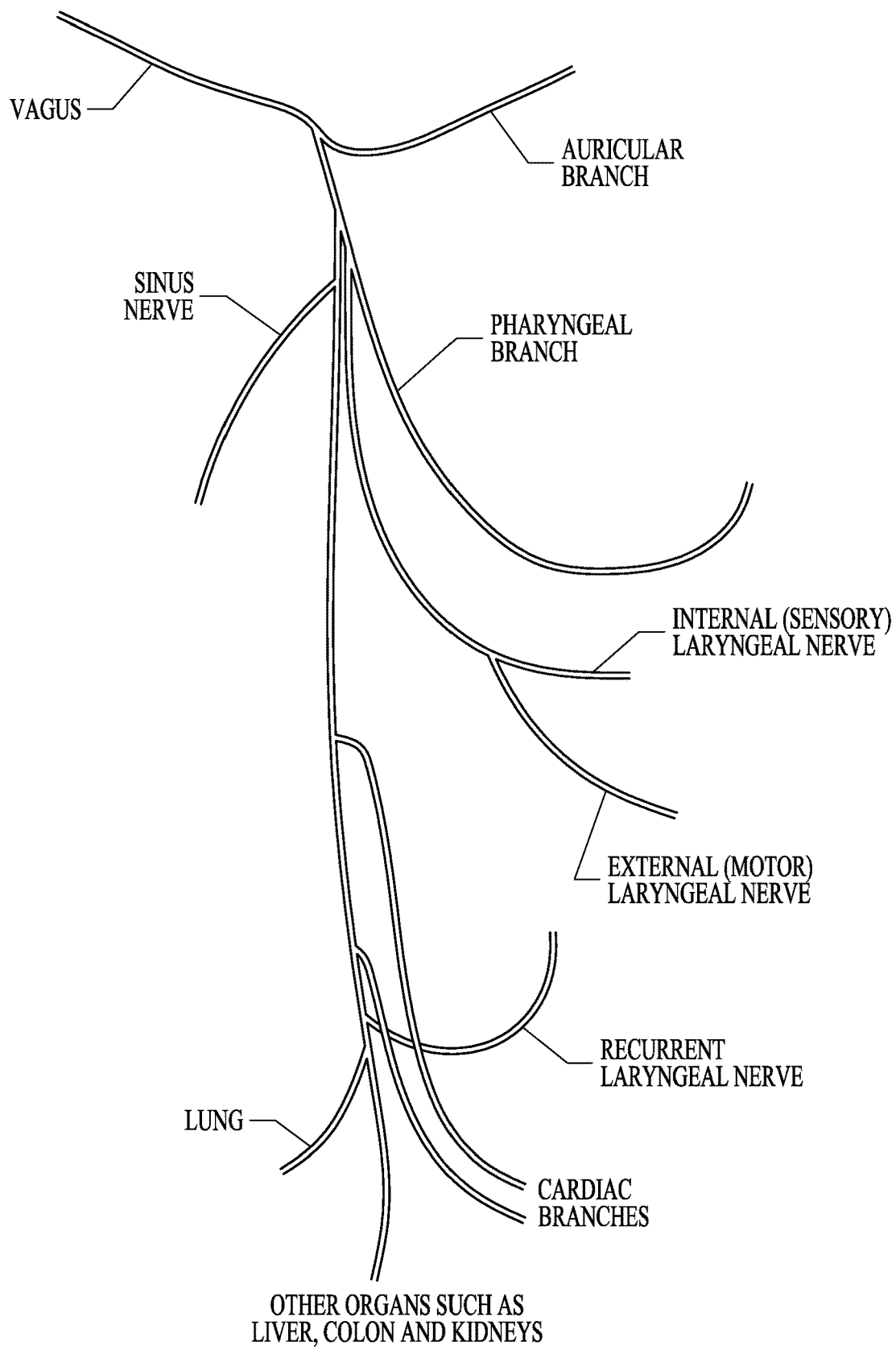
FIG. 34 illustrates some branches from the cervical vagus nerve.

FIG. 34 illustrates some branches from the cervical vagus nerve. The vagus nerve is discussed herein as an example of a complex nerve, and it is noted that the present subject matter may be used in applications that modulate the vagus nerve or other nerves. The vagus nerve 3419 is a combined nerve that separates into a number of branches, and continues to innervate other portions of the body including the liver, stomach, intestines, bladder and kidneys. It may desirable to modulate some fibers without modulating other fibers in a nerve such as the vagus nerve.

Figure 35A:
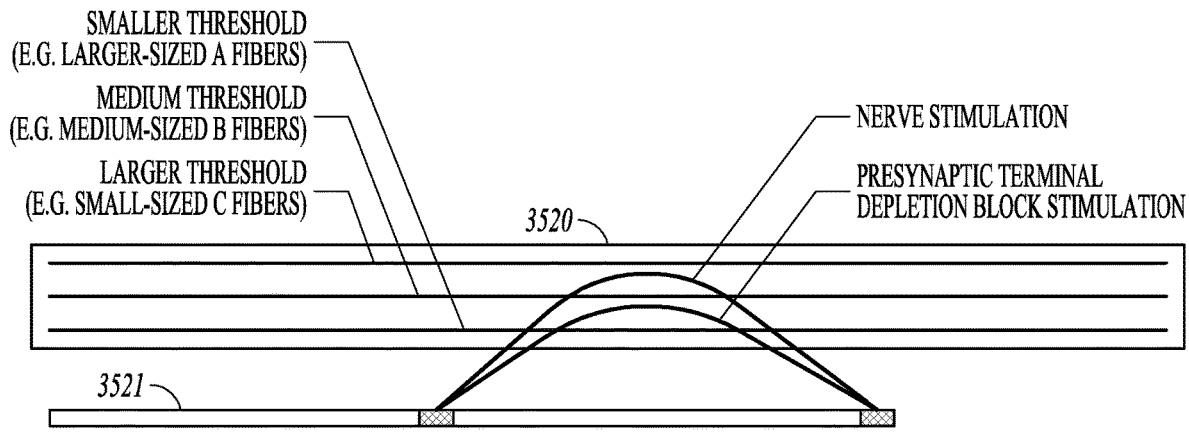
FIGS. 35A-35C illustrate selective stimulation using a simple illustration of different stimulation thresholds for different fiber types in a complex nerve, and further using different combinations of nerve stimulation and presynaptic terminal depletion block stimulation.
Figure 35B:
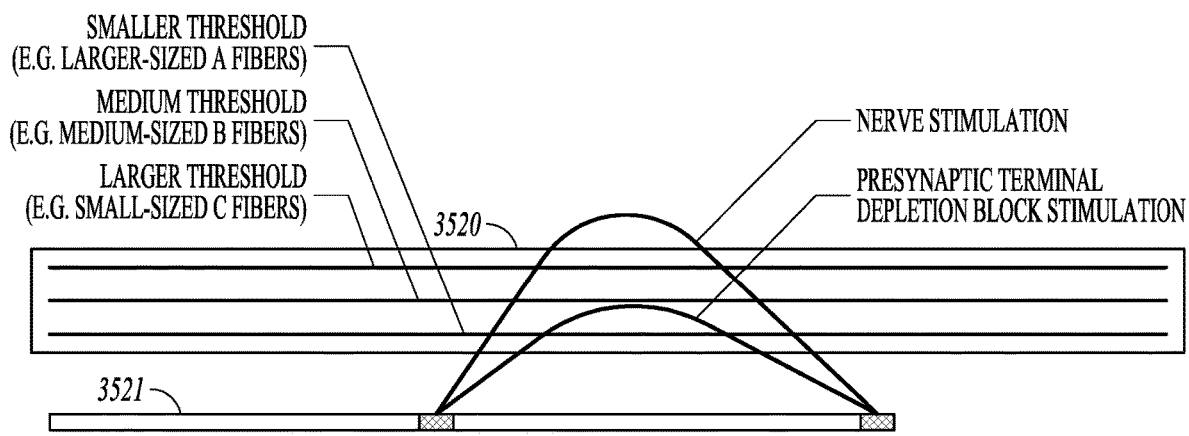
Figure 35C:
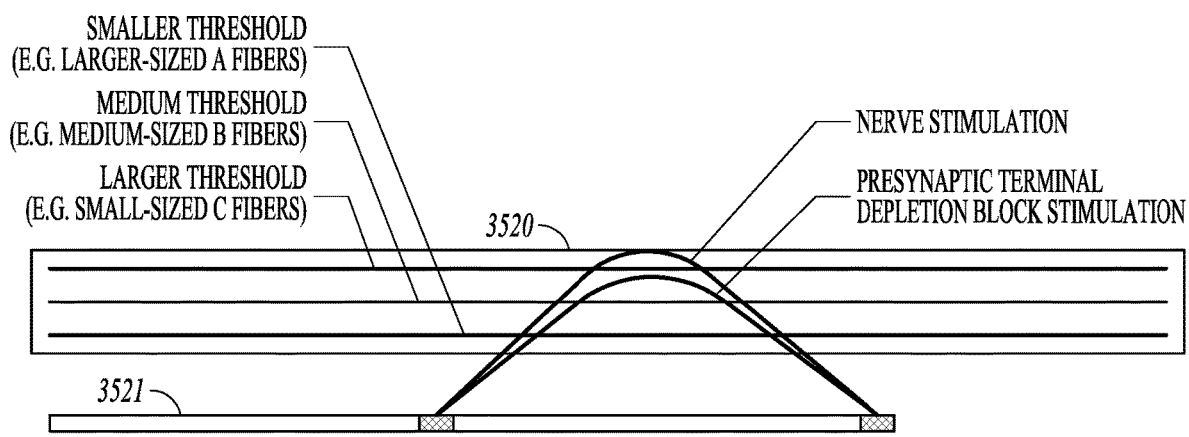

FIGS. 35A-35C illustrate selective stimulation using a simple illustration of different stimulation thresholds for different fiber types in a complex nerve 3520, and further using different combinations of nerve stimulation and presynaptic terminal depletion block stimulation (See Franke et al., US Pat. Pub. No. 20150202446). By way of example and not limitation, each of FIGS. 35A-35C include a bipolar stimulation lead 3521 configured to deliver both nerve stimulation and presynaptic terminal depletion block stimulation. The concept illustrated in these figures may apply to other types of stimulation such as unipolar stimulation and multipolar stimulation, including the fractionalized current contributions that may be implemented using multiple independent current sources. The figures provide a simple illustration of a nerve showing, by way of a simple example, three stimulation thresholds identified as a smaller threshold, a medium threshold and a larger threshold. The threshold for a given fiber is dependent on its fiber type as well as its location to the stimulation electrodes. However the concept may be simply illustrated based on fiber size. The simple illustration in FIGS. 35A-35C have larger-sized A type fibers with a smaller stimulation threshold, a medium-sized B type fibers with a medium stimulation threshold, and a smaller-sized C type fibers with a larger stimulation threshold. FIG. 35A illustrates selective stimulation of the medium-sized B type fibers with a medium stimulation threshold. The nerve stimulation has parameters to exceed the stimulation threshold of both the A and B fibers, and the depletion block has parameters to exceed the stimulation threshold of the A fibers. Thus, the combination of the nerve stimulation and the depletion block results in effectively stimulating only the B fibers as only the B fibers can communicate across their respective synaptic gap. FIG. 35B illustrates selective stimulation of the medium-sized B type fibers with a medium stimulation threshold and the smaller-sized C fibers with the smaller threshold. The nerve stimulation has parameters to exceed the stimulation threshold of the A, B and C fibers, and the depletion block has parameters to exceed the stimulation threshold of the A fibers. Thus, the combination of the nerve stimulation and the depletion block results in effectively stimulating only the B and C fibers as only the B and C fibers can communicate across their respective synaptic gap. FIG. 35C illustrates selective stimulation of the smaller-sized C fibers with the smaller threshold. The nerve stimulation has parameters to exceed the stimulation threshold of the A, B and C fibers, and the depletion block has parameters to exceed the stimulation threshold of the A and B fibers. Thus, the combination of the nerve stimulation and the depletion block results in effectively stimulating only the C fibers as only the C fibers can communicate across their respective synaptic gap. It is again noted that this concept may be applied to the same size of nerves, but where those nerves have different thresholds because of distance from the field or orientation to the field.

Figure 36:
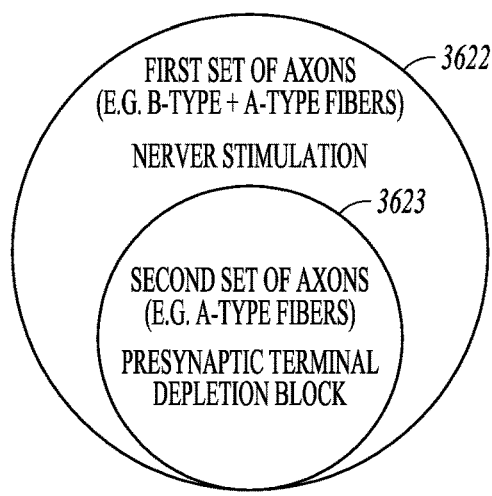
FIG. 36 illustrates a first set of axons in a nerve captured by nerve stimulation and a second set of axons captured by depletion block stimulation, wherein the second set of axons is a subset of the first set of axons.

FIG. 36 illustrates a first set of axons 3622 in a nerve captured by nerve stimulation and a second set of axons 3623 captured by depletion block stimulation, wherein the second set of axons is a subset of the first set of axons. The nerve stimulation is larger than a threshold for stimulation the first set of axons, and thus will cause action potentials to propagate in the larger, first set of axons. However, the depletion block will prevent the presynaptic terminals of the subset of axons from conducting across their respective synaptic cleft, and only the remainder of the first set of axons is effective in communicating across the synaptic cleft.

FIGS. 37A-37M illustrate some examples of electrode configurations that may be used to deliver the selective neural stimulation using depletion block stimulation. These examples are not intended to show all possible electrode configurations. The electrode configurations may be bipolar configurations, unipolar configurations, or multipole configurations. Furthermore, one or more target poles (also referred to as ideal or virtual poles") may be implemented by appropriately determining the fractionalized current contribution of multiple independent current sources. Thus, for example, one modulation field may be shaped and used to stimulate some neural targets, and another modulation field may be shaped and used to provide a depletion block to some neural targets. The spacing between electrodes may vary from that which is illustrated. Also, these examples are not intended to necessarily represent timing between the nerve stimulation and the depletion block stimulation. Some embodiments may interrupt the depletion block stimulation (e.g. 200 Hz) to provide windows of time within which a pulse of the nerve stimulation (e.g. 20 Hz) is delivered, thus avoiding simultaneous delivery of two signals using more than one cathode and/or more than one anode. The polarity of the signals may be switched. Some embodiments may share a cathode for both the nerve stimulation and the depletion block stimulation, and some embodiments may share an anode for both the nerve stimulation and the depletion block stimulation.

Figure 37A:
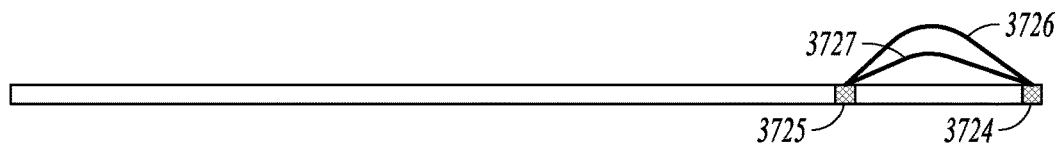
FIGS. 37A-37M illustrate some examples of electrode configurations that may be used to deliver the selective neural stimulation using depletion block stimulation.
Figure 37B:
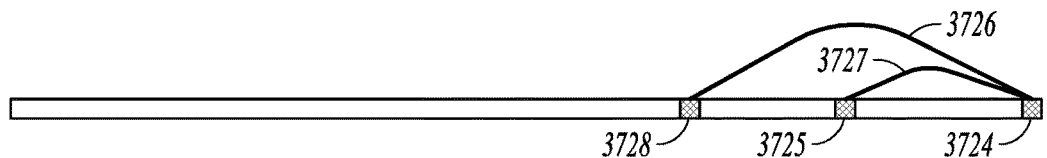
Figure 37C:
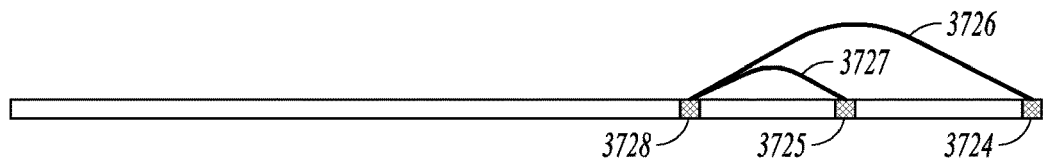
Figure 37D:
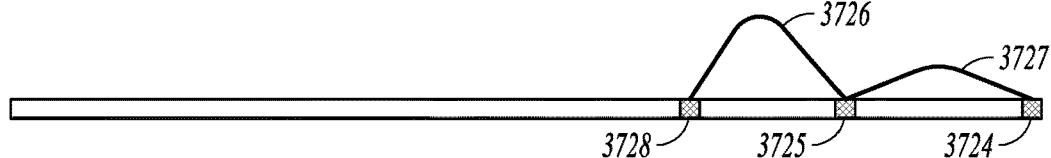
Figure 37E:
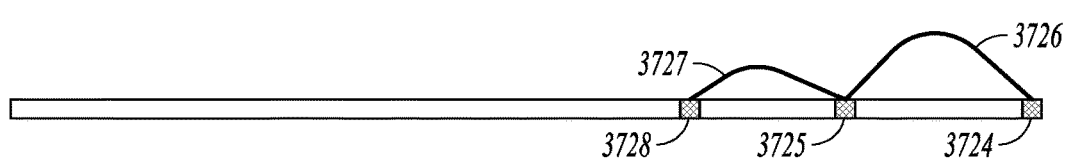
Figure 37F:
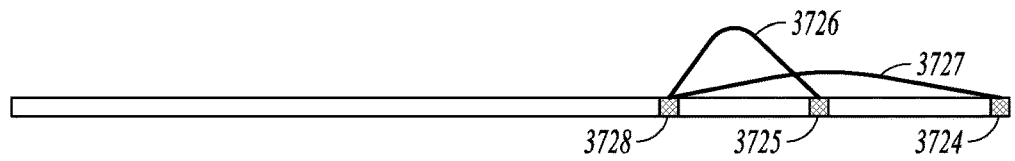
Figure 37G:
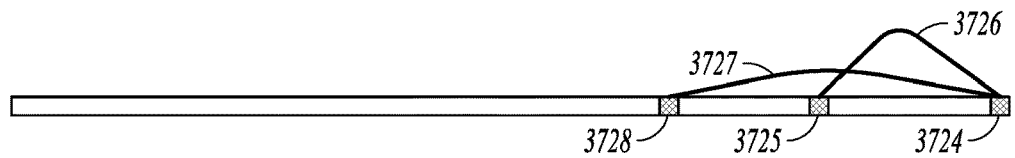
Figure 37H:
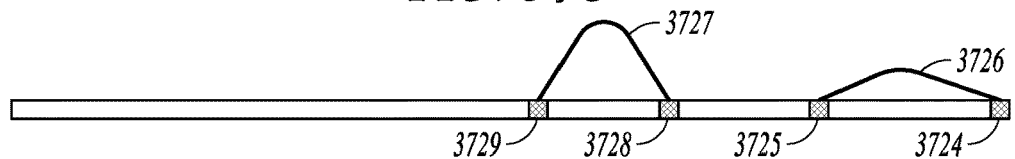
Figure 37I:
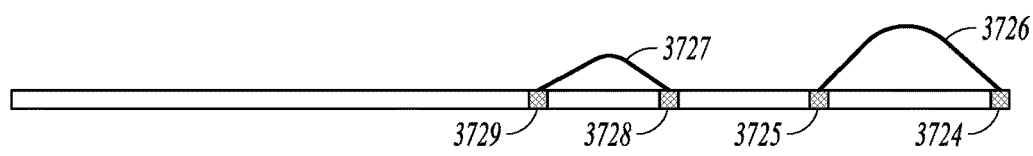
Figure 37J:
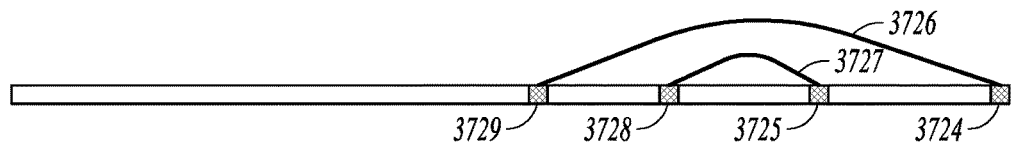
Figure 37K:
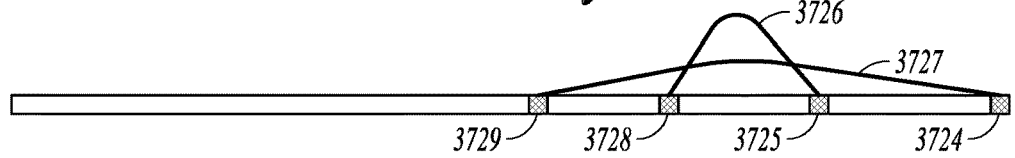
Figure 37L:
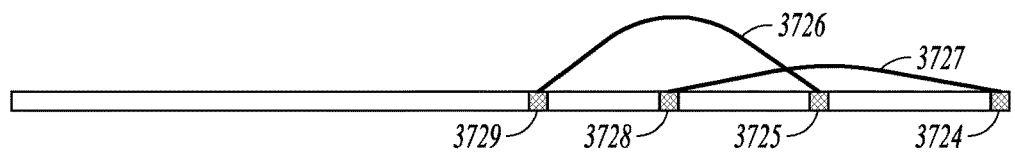
Figure 37M:
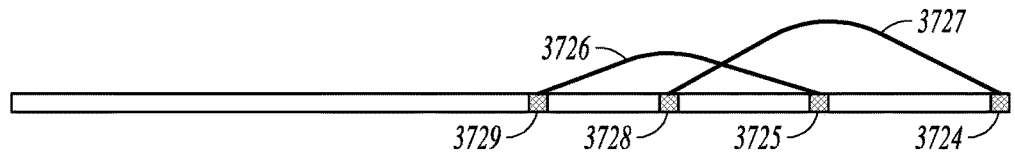

FIG. 37A illustrates an electrode configuration in which a first electrode 3724 and a second electrode 3725 are used to deliver the nerve stimulation 3726, and are used to also deliver the depletion block 3727. There may be some anatomical locations which are more amenable to stimulation using some other electrode arrangements than others. Some of these are illustrated below. Some embodiments may be configured to electronically switch the stimulation vectors among available electrodes on the lead. FIG. 37B illustrates an electrode configuration including a first electrode 3724, a second electrode 3725 and a third electrode 3728 in which the first electrode 3724 and the second electrode 3725 are used to deliver the depletion block 3727 and a first electrode 3724 and a third electrode 3728 are used to deliver the nerve stimulation 3726. FIG. 37C illustrates an electrode configuration including a first electrode 3724, a second electrode 3725 and a third electrode 3728 in which the first electrode 3724 and the third electrode 3728 are used to deliver the nerve stimulation 3726, and the second electrode 3725 and the third electrode 3728 are used to also deliver the depletion block 3727. FIG. 37D illustrates an electrode configuration including a first electrode 3724, a second electrode 3725 and a third electrode 3728 in which the first electrode 3724 and the second electrode 3725 are used to deliver the depletion block 3727, and the second electrode 3725 and the third electrode 3728 are used to deliver the nerve stimulation 3726. FIG. 37E illustrates an electrode configuration including a first electrode 3724, a second electrode 3725 and a third electrode 3728 in which the second electrode 3725 and the third electrode 3728 are used to deliver the depletion 3727, and the first electrode 3724 and the second electrode 3725 are used to deliver the nerve stimulation 3726. FIG. 37F illustrates an electrode configuration including a first electrode 3724, a second electrode 3725 and a third electrode 3728 in which the first electrode 3724 and the third electrode 3728 are used to provide the depletion block 3727 and the second electrode 3725 and the third electrode 3728 are used to provide the nerve stimulation 3726. FIG. 37G illustrates an electrode configuration including a first electrode 3724, a second electrode 3725 and a third electrode 3728 in which the first electrode 3724 and the second electrode 3725 are used to deliver the nerve stimulation 3726, and the first electrode 3724 and the third electrode 3728 are used to deliver the depletion block 3727. FIG. 37H illustrates an electrode configuration including a first electrode 3724, a second electrode 3725, a third electrode 3728, and a fourth electrode 3729 in which the first electrode 3724 and the second electrode 3725 are used to deliver the depletion block 3726 and the third electrode 3728 and the fourth electrode 3729 are used to deliver the nerve stimulation 3727. FIG. 37I illustrates an electrode configuration including a first electrode 3724, a second electrode 3725, a third electrode 3728, and a fourth electrode 3729 in which the first electrode 3724 and the second electrode 3725 are used to deliver the nerve stimulation 3726 and the third electrode 3728 and the fourth electrode 3729 are used to deliver the depletion block 3727. FIG. 37J illustrates an electrode configuration including a first electrode 3724, a second electrode 3725, a third electrode 3728, and a fourth electrode 3729 in which the first electrode 3724 and the fourth electrode 3729 are used to deliver the nerve stimulation 3726 and the second electrode 3725 and the third electrode 3728 are used to deliver the depletion block 3727. FIG. 37K illustrates an electrode configuration including a first electrode 3724, a second electrode 3725, a third electrode 3728, and a fourth electrode 3729 in which the first electrode 3724 and the fourth electrode 3729 are used to deliver the depletion block 3727 and the second electrode 3727 and the third electrode 3728 are used to deliver the nerve stimulation 3726. FIG. 37L illustrates an electrode configuration including a first electrode 3724, a second electrode 3725, a third electrode 3728, and a fourth electrode 3729 in which the first electrode 3724 and the third electrode 3728 are used to deliver the depletion block 3727 and the second electrode 3725 and the fourth electrode 3729 are used to deliver the nerve stimulation 3726. FIG. 37M illustrates an electrode configuration including a first electrode 3724, a second electrode 3725, a third electrode 3728, and a fourth electrode 3729 in which the first electrode 3724 and the third electrode 3728 are used to deliver the nerve stimulation 3727 and the second electrode 3725 and the fourth electrode 3729 are used to deliver the depletion block 3726.

The illustrated configurations in FIGS. 37A-37M show a one dimensional row of electrodes on a single lead. However, various lead embodiments disclosed herein refer to multi-electrode leads that may be arranged in various configurations such as an array of rows and columns. Furthermore, these multi-electrode configurations may be in 2 dimensional planes, or in a 3 dimensional volume when wrapped at least partially around targeted neural tissue and/or vessels. The relative positions between the depletion block and the stimulation may be applied to such 2 dimensional and 3 dimensional arrangements of electrodes. Furthermore, the concepts above may also be applied with respect to conduction block in addition to depletion block and nerve stimulation, or as an alternative to either depletion block or nerve stimulation.

Figure 38:
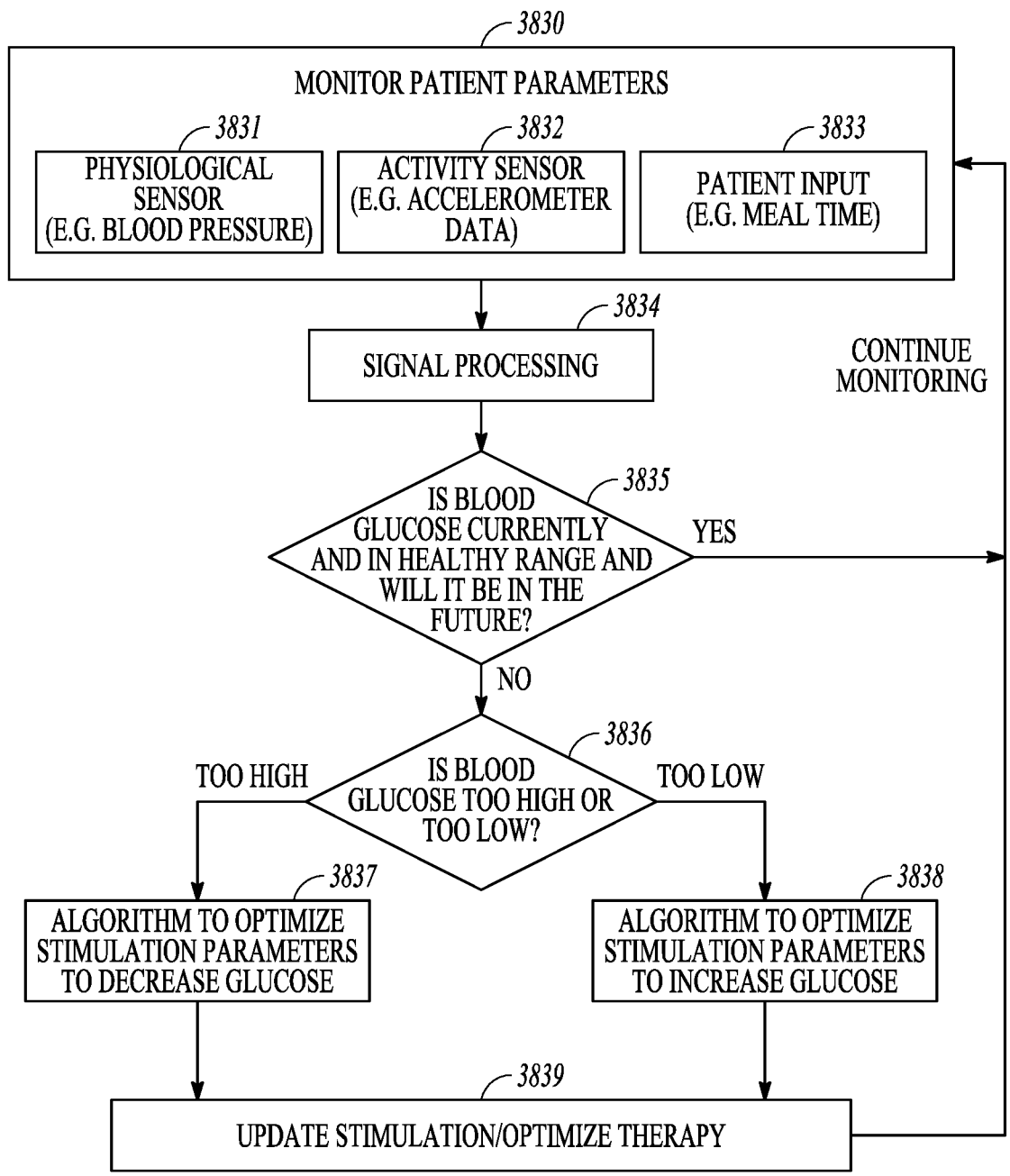
FIG. 38 illustrates a process for providing glycemic control.

FIG. 38 illustrates a process for providing glycemic control. By way of example, the illustrated process may be implemented using a system illustrated in FIG. 27. Patient parameters may be monitored at 3830. The monitoring of patient parameters may include monitoring glucose (e.g. blood glucoses using a physiological sensor 3831, monitoring activity using an activity sensor (e.g. accelerometer) 3832, and receiving patient input regarding diet at 3833. The signals resulting from the monitoring of the patient parameters may be processed at 3834 to make a determination, based on the monitored patient parameters, whether the blood glucose is current in a healthy range and whether it is expected to be in a healthy range in the future, as illustrated at 3835. If both the current and expected future glucose levels are determined to be in a healthy range, the process may return to 3830 to continue monitoring the patient parameters. Otherwise, the process may proceed to determine if the current or expected blood glucose level is too high or too low 3836. The stimulation parameters may be optimized to decrease glucose in response to determining that the current or expected blood glucose level is too high; 3837 and may be optimized to increase glucose in response to determining that the current or expected blood glucose level is too low 3838. The modulation parameters for the neuromodulation therapy may be updated to using the parameter(s) determined at 3837 or 3738. A benefit of the above process, which is able to both increase and decrease glucose levels, may be that the system may maintain tight glucose control by reducing glucose fluctuations before and after eating which may occur after eating fewer carbohydrates or more carbohydrates than expected.

Figure 39:
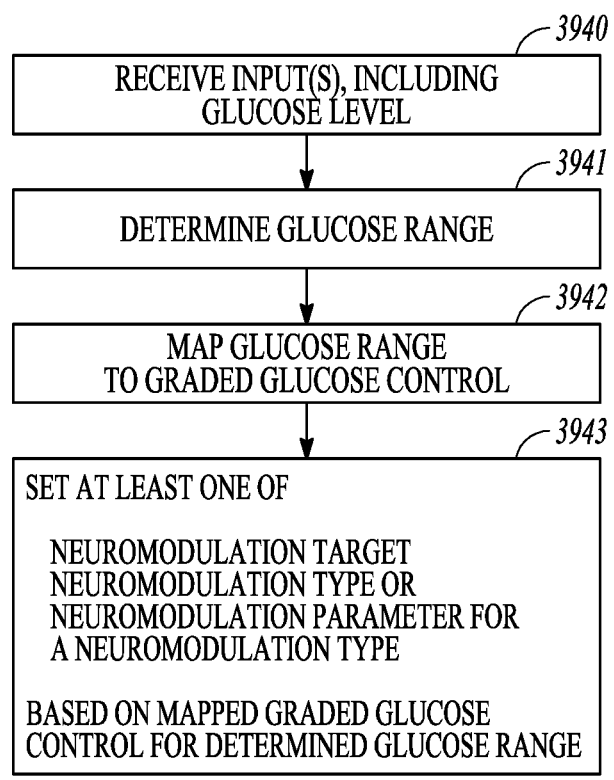
FIG. 39 illustrates a process for providing graded glucose control.

FIG. 39 illustrates a process for providing graded glucose control. By way of example, the illustrated process may be implemented using a system illustrated in FIG. 27. A controller or other processing system may receive patient input(s), including glucose level, as illustrated at 3940. The input(s) may be received via user input(s) and/or sensor(s). A 3941, the glucose range is determined from the received input(s). The determined glucose levels may be mapped to graded glucose control settings at 3942, as discussed with respect to FIGS. 27 and 28. As illustrated at 3943, the mapped glucose control settings, which are based on a determined glucose range, may be used to set at least one of a neuromodulation target, a neuromodulation type, or neuromodulation parameter(s) for a neuromodulation type.

Figure 40:
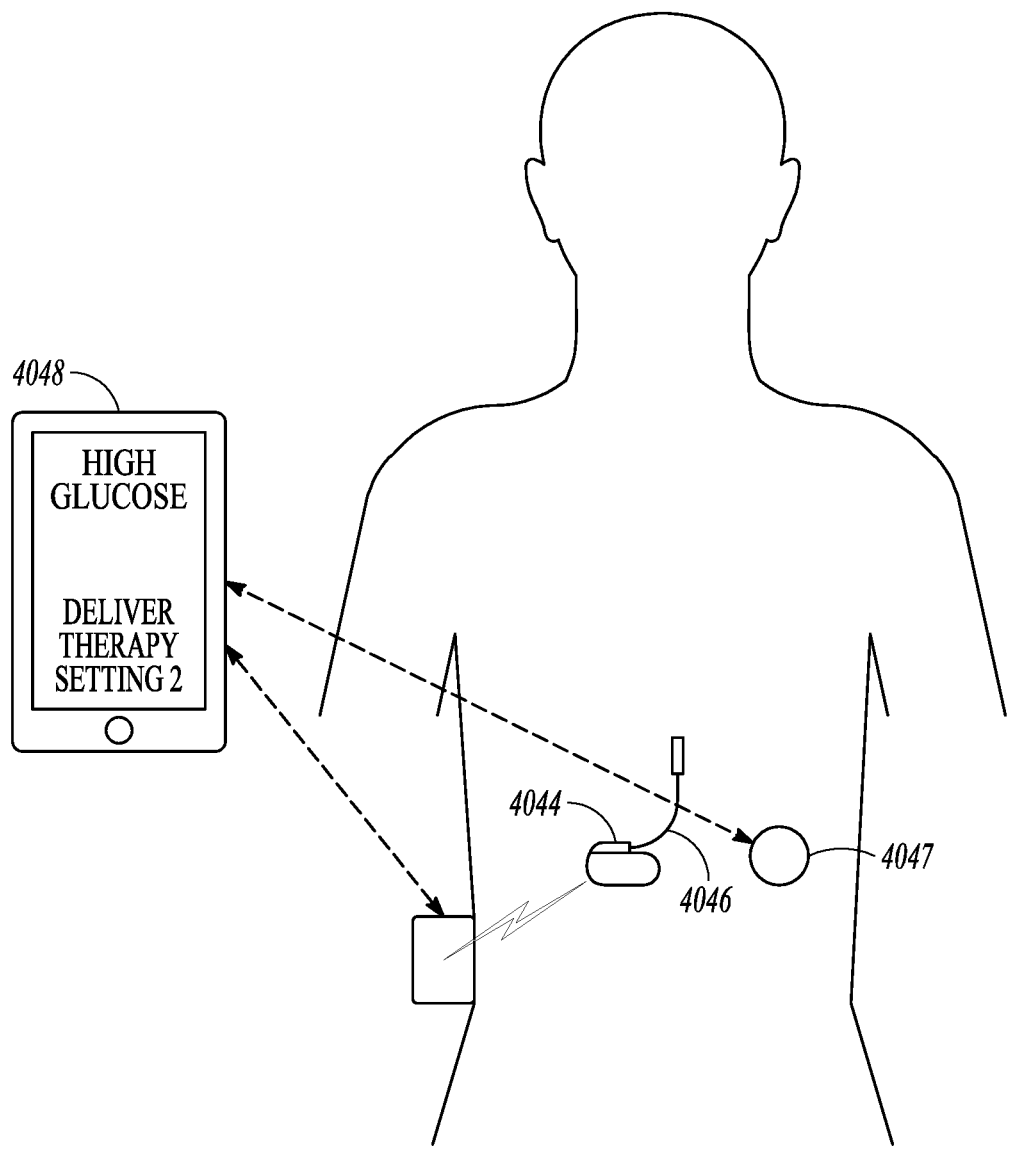
FIG. 40 illustrates system for providing glycemic control using an external therapy delivery device with a passive implanted device.

FIG. 40 illustrates system for providing glycemic control using an external therapy delivery device with a passive implanted device. The system may include a subdermal or subcutaneous passive receiver 4044 and an external device 4045 configured to deliver and control the therapy. The passive implanted device 4044 may include a lead 4046 with electrodes thereon for use to deliver the neuromodulation therapy, or may be a device integrated with the electrodes similar to as disclosed with respect to FIGS. 12-13. The system may further include a continuous glucose monitor 4047, which may be external or implantable, and an external patient device 4048 configured to communicate with the external device and the continuous glucose monitor. The passive implanted device may include a receiving coil tunneled to a location sub-dermal/sub-cutaneous in the patient's abdomen area. The neurostimulation energy may be delivered transcutaneously via the external device that is worn by the patient or used by the patient intermittently. A glucose monitoring system and a patient-facing application on an external device used by the patient may cooperate to provide alerts to the patient or send a signal to the wearable signal generator to activate/deactivate therapy. For example, the glucose monitor 4047 may send an alert to the mobile device 4048 and the patient may use that mobile device 4048 to manually control the external device 4045 to deliver therapy through the passive implanted device 4046. In some embodiments, the glucose monitor sends an alert to the patient's mobile device 4048 and the patient accepts the notice enabling the external device 4045 to initiate, terminate or adjust the therapy. It is noted that the functions provided by the external device 4045 and the mobile device 4048 may be integrated into a single device, or may be in separate devices as illustrated. Unlike an active implantable system, the passive implantable lead(s) use a power supply (e.g. battery) external to the patient. Therefore, the passive lead(s) may reduce repeat operations that may otherwise be needed for battery replacement. Those of ordinary skill in the art will understand that the passive implanted device may be implemented similar to how the implanted device is implemented in the discussions above.

Systems and methods, according to various embodiments, have been described. Some specific examples of therapies that may be implemented using the described system and methods are provided below.

Various embodiments may use a reversible block to down-regulate sympathetic activity and glucose levels via single sympathetic target. Some embodiments use an open-loop system to provide the reversible block. Other embodiments use a closed-loop system to provide the reversible block.

Some embodiments provide a method of modulating glucose levels for a medical condition in a patient, where the method includes implanting a medical device containing at least one electrode in proximity to one or more sympathetic nerves innervating the liver, and delivering non-thermal (e.g. electrical) energy to the at least one electrode in proximity to the one or more sympathetic nerves. The non-thermal energy may reversibly inhibit neural activity in the one or more sympathetic nerves, reducing glucose levels in the patient. Medical conditions that may be treated include diabetes, insulin resistance, genetic metabolic disease, hyperglycemia, obesity, hyperlipidemia, hypertension, endocrine disease and/or inflammatory disorders. The sympathetic nerves may include hepatic nerves.

The electrical energy may include alternating current delivered at a frequency between 100 Hz and 1 kHz such as may be used to provide a depletion block. The electrical energy may include alternating current delivered at a frequency between 1 kHz and 50 kHz such as may be used to provide a conduction block. The electrical energy may be delivered in pulse trains of any of the above. The electrical energy may be delivered at a frequency greater of between 100 kHz and 100 kHz, and may be delivered in brief pulse trains to minimize a thermal effect and producing glucose-reducing effects that last greater than 24 hours.

Various embodiments provide closed-loop neuromodulation of a sympathetic target to modulate glucose levels for a medical condition, in which a medical device is implanted to position at least one electrode in proximity to one or more sympathetic nerves innervating the liver, and at least one parameter from the patient indicative of a glucose level is sensed. Non-thermal energy may be delivered to the at least one electrode in proximity to the one or more sympathetic nerves in response to the at least one sensed parameter. The non-thermal energy may reversibly inhibit neural activity in the one or more sympathetic nerves to reduce glucose levels in the patient. The at least one sensed parameter may include at least one of a glucose metric, insulin level, glucose-regulating hormone level, or glucose-regulating enzyme level. The at least one of a plurality electrodes and therapy settings may be selected based on measured individual patient responses to electrical energy delivered to the sympathetic target. The individual patient response may include a sensed parameter of at least one of an intrinsic neural activity, evoked compound action potential, autonomic measure, glucose metric, insulin level, glucose-regulating hormone level, or glucose-regulating enzyme level.

According to some embodiments, electrical energy may be delivered at a frequency between 100 Hz and 1 kHz to down-regulate glucose levels when the level is measured to be above 140 mg/dL; electrical energy may be delivered at a frequency between 1 kHz and 50 kHz to down-regulate glucose levels when the level is measured to be above 170 mg/dL; electrical energy may be delivered at a frequency greater of between 100 kHz and 1000 kHz, and delivered in brief pulse trains to minimize a thermal effect, and producing glucose-reducing effects that last greater than 24 hours; and electrical energy may be delivered at a frequency of less than 50 Hz to up-regulate glucose levels when the level is measured to be less than 100 mg/dL.

Various embodiments provide closed-loop modulation of glucose levels by modulating two or more neural targets where the neural targets include sympathetic and/or parasympathetic targets. Various embodiments may modulate glucose levels for a medical condition in a patient by implanting a medical device containing at least one electrode in proximity to one or more nerves innervating the liver, sensing at least one parameter from the patient indicative of a glucose level, delivering non-thermal energy to the at least one electrode in response to the at least one sensed parameter, and increasing or decreasing neural activity in the at least one nerve innervating the liver to modulate glucose levels in response to the at least one sensed parameter. The targeted nerve(s) innervating the liver may include at least one of a sympathetic nerve around a portal vein, a sympathetic nerve around a hepatic artery, a parasympathetic nerve around a portal vein and/or a vagal parasympathetic nerve. Some embodiments may position at least one electrode in proximity to a sympathetic nerve innervating the liver and at least one electrode in proximity to a parasympathetic nerve innervating the liver. The at least one sensed parameter includes at least one of a glucose metric, insulin level, glucose-regulating hormone level, or glucose-regulating enzyme level. The at least one of a plurality electrodes and therapy settings may be selected based on measured individual patient responses to electrical energy delivered to parasympathetic and sympathetic targets. The individual patient response may include a sensed parameter indicative of at least one of an intrinsic neural activity, evoked compound action potential, autonomic measure, glucose metric, insulin level, glucose-regulating hormone level, or glucose-regulating enzyme level. The individual patient responses to parasympathetic and/or sympathetic modulation may be measured over a duration of time greater than 7 days. The system may have an ability for performing longer-term monitoring while continuing to adjust therapy using machine learning. The treated medical condition may include diabetes, insulin resistance, genetic metabolic disease, hyperglycemia, obesity, hyperlipidemia, hypertension, endocrine disease and/or inflammatory disorders.

In various embodiments, the electrical energy may be delivered to a sympathetic target at a frequency greater than 100 Hz to down-regulate glucose levels and/or at a frequency less than 50 Hz to down-regulate glucose levels. The electrical energy may be delivered to a parasympathetic target at a frequency greater than 100 Hz to up-regulate glucose levels and/or at a frequency less than 50 Hz to down-regulate glucose levels. The electrical energy delivered to the sympathetic target may be used to provide a depletion block of the sympathetic target, and may have a frequency between 100 Hz and 1 kHz. The electrical energy delivered to the sympathetic target may be used to provide a conduction block of the sympathetic target, and may have a frequency between 1 kHz and 50 kHz. The electrical energy delivered to the sympathetic target may be used to provide a pulsed RF block, and be delivered in pulse trains at a frequency of between 100 kHz and 1000 kHz. Various embodiments down-regulate glucose levels by delivering electrical energy at a frequency greater than 100 Hz to a sympathetic target concurrently with delivering energy at less than 50 Hz to a parasympathetic target. The parasympathetic modulation may cease before the sympathetic modulation ceases, which may be beneficial where the parasympathetic modulation has a quicker effect and where the sympathetic modulation has a stronger or more robust response. The system may be configured to down-regulate glucose levels when the level is measured to be above 140 mg/dL. The system may be configured to up-regulate glucose levels when electrical energy is delivered at a frequency of less than 50 Hz to a sympathetic target to stimulate action potentials in the sympathetic target, in some embodiments at a frequency of greater than 100 Hz to a parasympathetic target to inhibit action potentials in the parasympathetic target. The electrical energy may be delivered to up-regulate glucose levels when the level is measured to be below 100 mg/dL.

Various embodiments may control delivery of electrical energy using patient input such as dietary intake, mealtime, exercise or patient-activated therapy session. Various embodiments include an activity sensor for use to detect exercise levels, and automatically, semi-automatically or manually control therapy delivery using the detected exercise levels.

Various embodiments may determine an activation or neural block threshold for at least one of the plurality of electrodes in proximity to the sympathetic or parasympathetic nerves innervating the liver, and the energy delivered to the at least one electrode is above the determined threshold for full activation or block (e.g. for when full therapy is needed). An activation or neural block threshold may be determined for at least one of the plurality of electrodes in proximity to the sympathetic or parasympathetic nerves innervating the liver, and the energy may be delivered to the at least one electrode is below the determined threshold for a graded activation or block. The graded activation or block may be beneficial when the measured glucose level is not too far from the target glucose level. The electrical energy may be delivered to the target nerve with a duty cycle of between 10% and 95% to provide a form of graded therapy. The amount of graded activation or block may be determined by a patient's glucose level in addition to at least one of a patient input, time of day, activity level or dietary intake.

Various embodiments provide a closed-loop, fully-implanted system for modulating at least one of a sympathetic and parasympathetic nerve innervating the liver. The system may include an implantable lead, the lead including at least one electrode at a distal end. The lead may be communicatively coupled to an implantable pulse generator at a proximal end. A sensor may be configured to sense at least one parameter from the patient indicative of a glucose level. A processor may be configured to receive an input from the sensor and generate a recommended therapy setting. A controller may be configured to activate the implantable pulse generator to deliver electrical energy to the at least one electrode to modulate neural activity in at least one nerve innervating the liver to modulate glucose levels.

The sensor(s) may include at least one of an optical, electrochemical, biopotential, impedance, or electromagnetic sensor. The sensor may be an implantable sensor, or a partially invasive device such as an external sensor with microneedles penetrating the skin. The sensor may be a non-invasive sensor. The distal end of the implantable lead may be a cuff that wraps at least 180 degrees around the hepatic artery, and may have an inner diameter of between 2 and 20 mm. The distal end of the implantable lead may contain at least two electrodes. The implantable lead may be a percutaneous lead containing an expandable distal end for intravascular delivery and fixation. The system may include a patient interface that allows the patient to control therapy parameters, and may incorporate patient progress over time including at least one of a glucose metric trend, therapy usage trend, and activity level trend. Multiple independent current control may be used target specific sympathetic nerves located in distinct areas along the hepatic artery. For example, some embodiments may include at least eight electrodes to allow for 'mapping' and precise current delivery.)

Some embodiments may provide a system including a passive implanted lead including both a sensor providing input to a handheld patient controller (e.g. patient instruction to begin therapy) or providing input to a wearable pulse generator. The system may comprise an external pulse generator configured with a transmitter capable of transmitting waveform parameters and electrical energy across tissue to an implanted receiver, an implantable lead including at least one electrode at a distal end and a receiver at a proximal end capable of receiving the waveform parameters and electrical energy from the transmitter. The system may include a sensor configured to sense at least one parameter from the patient indicative of a glucose level, a processor configured to receive an input from the sensor and generate a recommended therapy setting, and a controller that may be activated by a patient to cause the external pulse generator to initiate, change or stop therapy to modulate glucose levels.

Some embodiments may include a patient interface. The patient interface may include a glucose measurement and a recommended therapy session. The patient interface may allow a patient to input dietary intake and mealtime, which may be used by the processor to calculate the recommended therapy session. Various embodiments may include a patient-facing or physician-facing interface that trends patient progress over time, including at least one of a glucose metric trend, therapy usage trend, and activity level trend.

Various embodiments disclosed above include a glucose monitor. Any direct or indirect measure of glucose may be used in our closed-loop system, either via a sensor communicatively coupled to a processor and controller within a pulse generator, or to a processor within a non-invasive device such as a handheld remote/patient interface. For examples of an indirect measures, enzymes can be measured, including glucose-6-phosphatase, glucose oxidase, pyruvate, fructose 1,6 biphosphate, phosphoenolpyruvate, glyceraldehyde 3-phosphate, phosphofructokinase, and glycated hemoglobin. By way of example, Vaddiraju et al., J Diabetes Sci Technol. 2010 November; 4(6): 1540-1562, refer to a number of continuous glucose monitoring technologies. Vaddiraju et al. is incorporated herein by reference, as these glucose monitoring technologies may be used in the present subject matter.

The above detailed description is intended to be illustrative, and not restrictive. The scope of the disclosure should, therefore, be determined with references to the appended claims, along with the full scope of equivalents to which such claims are entitled.

What is claimed is:

1. A method for providing a glucose control therapy using a lead with multiple electrodes operably positioned proximate to nerves that innervate and are proximate to an organ involved with glucose control, the method comprising:
   selecting one or more modulation electrodes from the multiple electrodes for use to deliver modulation energy and selecting one or more sense electrodes from the multiple electrodes for use to sense neural activity in the nerves;

delivering modulation energy using the selected one or more modulation electrodes;

sensing neural activity in the nerves using the selected one or more sense electrodes, and determining if the delivered modulation energy captures the nerves based on the sensed neural activity, wherein the lead includes at least one distal patch configured to wrap at least partially around tissue including the nerves, the multiple electrodes being on the at least one distal patch, and the lead is configured to be intravascularly fed into position proximate to the nerves, wherein delivering modulation energy includes using multiple independent current sources to independently deliver current to two or more of the modulation electrodes, and wherein each of the multiple independent current sources is configured to source or sink current, each of the multiple independent current sources including a PDAC configured for use to source current and an NDAC configured for use to sink current.

2. The method of claim 1, further comprising controlling current contributions of each of the modulation electrodes to form at least one target pole within a tissue region that includes the nerves, and implementing a mapping process that includes:

modifying the current contributions from each of the modulation electrodes to move the at least one target pole through different positions in the tissue region, sensing neural activity in the nerves using the one or more sensed electrodes when the at least one target pole is in each of the different positions, and determining if the delivered modulation energy using the at least one target pole at each of the different positions captures the nerves based on the sensed activity in the nerves.

3. The method of claim 1, wherein the mapping process further includes sensing a physiological response, and using the sensed physiological response to determine if the modulation energy is capturing a sympathetic nerve or a parasympathetic nerve.

4. The method of claim 1, wherein the mapping process further includes implementing a capture threshold detection process when the at least one target pole is in each of the different positions, the capture threshold detection process including testing different values for a modulation parameter and sensing neural activity for each of the different values to determine a threshold modulation parameter value for causing neural activity in the nerves.

5. The method of claim 4, further comprising using the threshold modulation parameter value to set a modulation parameter value for a graded neuromodulation therapy.

6. The method of claim 4, wherein the threshold modulation parameter value controls current contribution amplitudes of the modulation electrodes.

7. The method of claim 1, wherein the mapping process further includes:

sensing a physiological response, and using the sensed physiological response to determine if the modulation energy is capturing a sympathetic nerve or a parasympathetic nerve;

implementing a capture threshold detection process when the target pole is in each of the different positions, the capture threshold detection process including testing different values for a modulation parameter and sensing neural activity for each of the different values to determine a threshold modulation parameter value for causing neural activity in the nerves; and recording, for each of the different positions of the target pole, whether the modulation energy is capturing the sympathetic nerve or the parasympathetic nerve, and the threshold modulation parameter value.

8. The method of claim 1, wherein the nerves include a hepatic nerve that innervates and is proximate to a liver.

9. The method of claim 1, wherein the nerves include a pancreatic nerve that innervates and is proximate to a pancreas.

10. The method of claim 1, wherein the lead includes at least one distal patch configured to wrap at least partially around tissue including the nerves, the multiple electrodes being on the at least one distal patch.

11. The method of claim 10, further comprising wrapping the at least one distal patch around a hepatic vessel and hepatic nerves.

12. The method of claim 10, wherein the lead includes two or more patches.

13. The method of claim 10, wherein the multiple electrodes on the at least one patch are arranged in an electrode array of at least two rows of electrodes and at least two columns of electrodes.

14. The method of claim 10, wherein the lead is configured to be intravascularly fed into position proximate to the nerves.

15. The method of claim 14, wherein the lead is configured to be intravascularly fed through an aorta into a hepatic artery to position the lead proximate to a hepatic nerves.

16. The method of claim 14, wherein a distal portion of the intravascularly-fed lead is configured to puncture through the hepatic artery and at least partially wrap around the hepatic artery.

17. The method of claim 14, wherein a distal portion of the intravascularly-fed lead is configured to expand to abut against a wall of the hepatic artery.

18. The method of claim 14, further comprising laparoscopically, percutaneously, or surgically positioning the lead proximate to the nerve.

* * * * *